US012570643B2

(12) United States Patent
Wang et al.

(10) Patent No.: US 12,570,643 B2
(45) Date of Patent: Mar. 10, 2026

(54) 3-ARYLOXY-3-FIVE-MEMBERED HETEROARYL PROPYLAMINE COMPOUND, AND CRYSTAL FORM AND USE THEREOF

(71) Applicant: Shanghai Leado Pharmatech Co. Ltd., Shanghai (CN)

(72) Inventors: Youxin Wang, Shanghai (CN); Lingling Zhang, Shanghai (CN); Qiang Ding, Shanghai (CN)

(73) Assignee: SHANGHAI LEADO PHARMATECH CO. LTD., Shanghai (CN)

( * ) Notice: Subject to any disclaimer, the term of this patent is extended or adjusted under 35 U.S.C. 154(b) by 1104 days.

(21) Appl. No.: 17/611,539

(22) PCT Filed: May 14, 2020

(86) PCT No.: PCT/CN2020/090354
§ 371 (c)(1),
(2) Date: Nov. 15, 2021

(87) PCT Pub. No.: WO2020/228789
PCT Pub. Date: Nov. 19, 2020

(65) Prior Publication Data

US 2022/0213075 A1 Jul. 7, 2022

(30) Foreign Application Priority Data

May 16, 2019 (CN) ......................... 201910411311.X
Aug. 15, 2019 (WO) ................ PCT/CN2019/100846
Feb. 14, 2020 (CN) ......................... 202010093736.3

(51) Int. Cl.
*C07D 407/12* (2006.01)
*A61P 25/02* (2006.01)
*A61P 29/00* (2006.01)
*C07D 409/12* (2006.01)

(52) U.S. Cl.
CPC ............ *C07D 407/12* (2013.01); *A61P 29/00* (2018.01); *C07D 409/12* (2013.01); *C07B 2200/13* (2013.01)

(58) Field of Classification Search
CPC ..... C07D 407/12; C07D 409/12; A61P 29/00; A61P 25/02; A61K 31/381
See application file for complete search history.

(56) References Cited

U.S. PATENT DOCUMENTS 5,023,269 A 6/1991 Robertson et al.
7,037,932 B2 5/2006 Gallagher et al.
12,139,476 B2 * 11/2024 Wang ...................... A61P 29/00
2004/0176435 A1 * 9/2004 Gallagher ............ C07D 333/54 549/466
2011/0178127 A1 7/2011 Zhong et al.
2017/0369466 A1 12/2017 Guo et al.
2019/0175599 A1 6/2019 Khairatkar-Joshi et al.
2021/0332035 A1 10/2021 Wang et al.
2022/0119375 A1 4/2022 Wang et al.

FOREIGN PATENT DOCUMENTS

| | | | |
|---|---|---|---|
| CN | 101657438 | A | 2/2010 |
| CN | 105497019 | A | 4/2016 |
| CN | 105497020 | A | 4/2016 |
| CN | 107151241 | A | 9/2017 |
| CN | 107625762 | A | 1/2018 |
| CN | 107840845 | A | 3/2018 |
| CN | 108947989 | A | 12/2018 |
| CN | 109748914 | A | 5/2019 |
| CN | 111943943 | A | 11/2020 |
| EP | 0273658 | A1 | 7/1988 |
| EP | 2305669 | A1 | 4/2011 |
| EP | 3339304 | A1 | 6/2018 |
| JP | 2004534037 | A | 11/2004 |

(Continued)

OTHER PUBLICATIONS

Kilbourn, M. Nucl. Med. Biol. 1989, 16 (7), 681-686.*
Kremer et al. The Journal of Neuroscience 2018, 38 (46), 9934-9954.*
Depreux et al. J. Med. Chem. 1994, 37, 3231-3239.*
Co-pending U.S. Appl. No. 17/268,763 , filed Feb. 16, 2021.*
Co-pending U.S. Appl. No. 17/799,487, filed Aug. 12, 2022.*
Co-pending U.S. Appl. No. 18/907,976, filed Oct. 7, 2024.*
Office Action issued Feb. 24, 2025, in U.S. Appl. No. 17/268,763, by Wang et al.
Boot et al., "Benzothienyloxy phenylpropanamines, novel dual inhibitors of serotonin and norepinephrine reuptake," Bioorganic & Medicinal Chemistry Letters, vol. 14, pp. 5395-5399 (2004).

(Continued)

*Primary Examiner* — Irina Neagu
(74) *Attorney, Agent, or Firm* — Panitch Schwarze Belisario & Nadel LLP

(57) ABSTRACT

A 3-aryloxyl-3-five-membered heteroaryl propylamine compound, and crystal form and use thereof are provided. Specifically, a compound, or a pharmaceutically acceptable salt or a prodrug thereof, the compound having a structure of formula I is described. The compound, or pharmaceutically acceptable salt or prodrug thereof has an excellent inhibition function for a transient receptor potential channel protein (TPR), and has a good treatment function for diseases associated with the TPR.

I

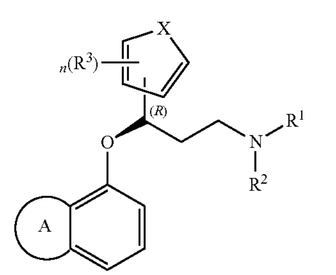

10 Claims, 5 Drawing Sheets

(56) References Cited

FOREIGN PATENT DOCUMENTS

| | | | |
|---|---|---|---|
| JP | 2011525497 | A | 9/2011 |
| WO | 02094262 | A1 | 11/2002 |
| WO | 2007005644 | A2 | 1/2007 |
| WO | 2010075353 | A1 | 7/2010 |
| WO | 2011060962 | A1 | 5/2011 |
| WO | 2011128370 | A1 | 10/2011 |
| WO | 2014096377 | A1 | 6/2014 |
| WO | 2018115064 | A1 | 6/2018 |
| WO | 2018115069 | A1 | 6/2018 |
| WO | 2020035040 | A1 | 2/2020 |
| WO | 2020035070 | A1 | 2/2020 |
| WO | 2020228789 | A1 | 11/2020 |
| WO | 2021160134 | A1 | 8/2021 |
| WO | 2023016249 | A1 | 2/2023 |

OTHER PUBLICATIONS

Cashman et al., "Inhibition of serotonin and norepinephrine reuptake and inhibition of phosphodiesterase by multi-target inhibitors as potential agents for depression," Bioorganic & Medicinal Chemistry, vol. 17, pp. 6890-6897 (2009).
Extended European Search Report issued Jan. 19, 2022 in EP Application No. 19849600.2.
Extended European Search Report issued Sep. 16, 2021 in EP Application No. 19849974.1.
International Search Report issued Jul. 20, 2020 in International Application No. PCT/CN2020/090354.
International Search Report issued Nov. 13, 2019 in International Application No. PCT/CN2019/100846.
International Search Report issued Nov. 19, 2019 in International Application No. PCT/CN2019/101197.
Office Action issued Apr. 14, 2022 in JP Application No. 2021532506 (English Translation Only).
Office Action issued Apr. 14, 2022 in JP Application No. 2021532507 (English Translation Only).
RN 1181660-13-8 (Sep. 2009).
Written Opinion issued Nov. 13, 2019 in International Application No. PCT/CN2019/100846.
Written Opinion issued Nov. 19, 2019 in International Application No. PCT/CN2019/101197.
Written Opinion issued Jul. 20, 2020 in International Application No. PCT/CN2020/090354.
Xue et al., "Pharmacokinetic profiles contribute to the differences in behavioral pharmacology of 071031B enantiomers as novel serotonin and norepinephrine reuptake inhibitors," Journal of Psychopharmacology, vol. 31, No. 3, pp. 377-386 (2017).
Zhang et al., "Design, Synthesis and Antidepressive Activity of Duloxetine Derivatives," Acta Pharmaceutica Sinica, vol. 45, No. 7, pp. 869-873 (2010) (English Abstract Only).
CAS Registry No. 1181972-55-3, which entered STN on Sep. 10, 2009 (Year: 2009).
Office Action issued Jul. 7, 2022 in U.S. Appl. No. 17/268,914, by Wang et al.
Office Action issued Aug. 22, 2023 in U.S. Appl. No. 17/268,914, by Wang et al.
Sheridan, R., "The Most Common Chemical Replacements in Drug-Like Compounds," J. Chem. Inf. Comput. Sci., vol. 42, pp. 103-108 (2002).
Wong et al., "Dual serotonin and noradrenaline uptake inhibitor class of antidepressants—Potential for greater efficacy or just hype?," Progress in Drug Research, vol. 58, pp. 169-222 (2002).
Xue et al., "Antidepressant-like effects of 071031B, a novel serotonin and norepinephrine reuptake inhibitor," European Neuropsychopharmacology, vol. 23, pp. 728-741 (2013).
Banker et al., "Modern Pharmaceutics, 3rd Edition, Revised and Expanded," Marcel Dekker, pp. 451 and 596 (1996).
Beaumont et al., "Design of Ester Prodrugs to Enhance Oral Absorption of Poorly Permeable Compounds: Challenges to the Discovery Scientist," Current Drug Metabolism, vol. 4, pp. 461-485 (2003).
Bymaster et al., "Duloxetine (CymbaltaTM), a Dual Inhibitor of Serotonin and Norepinephrine Reuptake," Bioorganic & Medicinal Chemistry Letters, vol. 13, pp. 4477-4480 (2003).
Ding et al., "TRPA1 channel mediates organophosphate-induced delayed neuropathy," Cell Discovery, vol. 3, Article No. 17024, pp. 1-15 (2017).
Gleeson et al., "Probing the links between in vitro potency, ADMET and physicochemical parameters," Nature Reviews, Drug Discovery, vol. 10, pp. 197-208 (2011).
Hang, "Analgesic effect and mechanisms of amoxetine as a novel potent serotonin and norepinephrine dual reuptake Inhibitor," China Academic Journal Electronic Publishing House, pp. 1-101 (partial English translation at pp. 9-12) (2016).
Malmborg et al., "Predicting human exposure of active drug after oral prodrug administration, using a joined in vitro/in silico-in vivo extrapolation and physiologically-based pharmacokinetic modeling approach," Journal of Pharmacological and Toxicological Methods, vol. 67, pp. 203-213 (2013).
Morrison, K., "Physical Science Level 3," Pearson Education, pp. 15-26 (2008).
Office Action issued May 11, 2022 in CN Application No. 201980052852.6.
Office Action issued Nov. 17, 2022 in JP Application No. 2021532507 (English Translation Only).
Office Action issued Dec. 19, 2022 in U.S. Appl. No. 17/268,914 by Wang et al.
Partial Supplementary Search Report issued Jul. 10, 2023 in EP Application No. 20806595.3.
Rautio et al., "Prodrugs: design and clinical applications," Nature Reviews Drug Discovery, vol. 7, pp. 255-270 (2008).
Science of Kampo Medicine Chinese Medicine, vol. 37, pp. 164-175 (2013).
Wolff, M., "Burger's Medicinal Chemistry and Drug Discovery, Fifth Edition, vol. 1: Principles and Practice, Part 1," John Wiley & Sons, pp. 975-977 (1995).

* cited by examiner

3-ARYLOXY-3-FIVE-MEMBERED HETEROARYL PROPYLAMINE COMPOUND, AND CRYSTAL FORM AND USE THEREOF

CROSS-REFERENCE TO RELATED APPLICATIONS

This application is a Section 371 of International Application No. PCT/CN2020/090354, filed May 14, 2020, which was published in the Chinese language on Nov. 19, 2020 under International Publication No. WO 2020/228789 A1, which claims priority under 35 U.S.C. § 119 (b) to Chinese Application No. 201910411311.X, filed on May 16, 2019, International Application No. PCT/CN2019/100846, filed Aug. 15, 2019, and Chinese Application No. 202010093736.3, filed Feb. 14, 2020, the disclosures of which are incorporated herein by reference in their entireties.

FIELD OF THE INVENTION

The invention relates to the field of pharmacochemistry and pharmacotherapeutics, in particular to a 3-aryloxy-3-five-membered heteroaryl-propylamine compounds and crystal form and use thereof.

BACKGROUND OF THE INVENTION

Pain is known as the fifth vital sign and is an alarming sign of damage to the body's tissues. Pain is one of the most common reasons for patients to seek medical treatment. According to its duration, pain can be divided into acute pain (acute onset, short duration or continuous state) and chronic pain (slow onset or transformed from acute pain, long duration, or intermittent onset, and many chronic pains can not find obvious damage). Acute pain is mostly nociceptive pain caused by tissue trauma, including postoperative pain, trauma, post-burn pain, childbirth pain, visceral pain such as angina pectoris, biliary colic and renal colic, etc, fracture pain, toothache and cancer pain. Postoperative and post-traumatic pain are the most common and urgent acute pain in clinic. Chronic pain mainly includes neuropathic pain, painful osteoarthritis, chronic back and low back pain and vascular pain, etc. Main types of neuropathic pain includes trigeminal neuralgia, diabetic pain, sciatica or postherpetic neuralgia. The global prevalence rate of neuropathic pain is about 10%, with a high incidence and a large number of patients. Chronic pain affects 10%-30% of the population in the United States, causing about $635 billion in annual social spending, more than the combination of cancer and heart disease. Chronic pain has complex etiology and is a refractory disease. Only less than 50% of patients can achieve effective analgesia through drug treatment. It is estimated that the total market size of neuralgia drugs in China will be close to 26 billion yuan in 2026, and the market size of ion channel neuralgia drugs will exceed 20 billion yuan.

Traditional analgesics mainly include opioids and non-steroidal anti-inflammatory drugs. Opioids have strong analgesic effect, but long-term use can easily lead to tolerance, dependence and addiction, and have adverse reactions such as respiratory depression and central sedation. Non-steroidal anti-inflammatory drugs have only moderate analgesic effect, and have adverse reactions such as gastrointestinal bleeding and cardiotoxicity.

Recently, the National Security Council of the United States released a report on preventable deaths, which shows that for the first time in American history, the proportion of deaths caused by opioid overdose exceeded that caused by car accidents. According to the commission's analysis of data on accidental deaths in 2017, one in 96 Americans died from an opioid overdose, compared with one in 103 deaths from car accidents. Opioid abuse has caused a serious social crisis sweeping across the United States, so the market needs analgesics having new mechanisms.

TRPA1 is a member of the TRP ion channel superfamily and the only member of the TRPA subfamily. TRPA1 is a non-selective cation channel and can permeate $Na^+$, $K^+$, $Ca^{2+}$ and $Mg^{2+}$. TRPA1 is mainly distributed in the primary sensory neurons of dorsal root nerve (DRG), trigeminal nerve (TG) and vagus nerve (VG). From the distribution of human system, TRPA1 is highly expressed in peripheral nervous system, respiratory system, gastrointestinal system and urinary system. When these organs and tissues are dysfunctional, the expression and function of TRPA1 channel are usually abnormal simultaneously. TRPA1 can transform cold stimulation, chemical stimulation and mechanical stimulation into inward current, which triggers a series of physiological functions and participates in the formation of various pain senses. Inflammatory pain is a common problem of some chronic diseases, and still lack of effective treatment in clinic. Animal studies have shown that TRPA1 participates in inflammatory reaction and plays an important role in inflammatory pain. By using TRPA1 specific blocker, inflammatory pain reaction in rats can obviously be alleviated. From the current research, TRPA1 plays an important role in the occurrence of asthma and cough, and the compounds that induce asthma and cough, whether endogenous or exogenous, can activate TRPA1. TRPA1 antagonists can alleviate asthma symptoms and block airway hyperresponsiveness. Through different animal models of visceral hypersensitivity, such as colitis, colorectal dilatation or stress, it is confirmed that TRPA1 is involved in the regulation of visceral hypersensitivity and plays an important role in visceral pain. Neurogenic pain is a pain syndrome caused by central or peripheral nervous system damage or disease, which is mainly manifested as hyperalgesia, abnormal hyperalgesia and spontaneous pain. In recent years, more and more studies have shown that TRPA1 channel plays an important role in different neurogenic pain, such as diabetic neuropathy and neuropathy caused by chemotherapy drugs. Recent studies have also shown that TRPA1 also plays a mediating role in toothache, migraine and other pain, and TRPA1 antagonist can obviously relieve the occurrence of pain symptoms.

TRPA1 is widely distributed and expressed in human system. In addition to the above physiological functions involved by TRPA1, the reported indications for TRPA1 inhibitors also involve inflammatory bowel disease, chronic obstructive pulmonary disease, antitussive, antipruritic, allergic rhinitis, ear diseases, anti-diabetes, urinary incontinence and so on. TRPA1 is a proven new target for the treatment of many diseases.

Therefore, considering that pain treatment is an unmet clinical demand at present, and many problems existing in existing therapeutic drugs, it is urgent to develop a therapeutic drug for TRP targets (especially TRPA1 targets) in the field, so as to improve the therapeutic effect of diseases.

SUMMARY OF THE INVENTION

The purpose of the present invention is to provide a compound with a novel structure that targets the TRP channel (especially the TRPA1 target), and crystal form and use thereof.

In the first aspect of the present invention, it provides a use of a compound, or a pharmaceutically acceptable salt thereof, or a prodrug thereof, for (a) preparing a transient receptor potential channel protein (TRPA1) inhibitor; (b) manufacturing a medicament for preventing and/or treating diseases related to transient receptor potential channel protein (TRPA1);

wherein the compound has a structure of formula Z:

Z

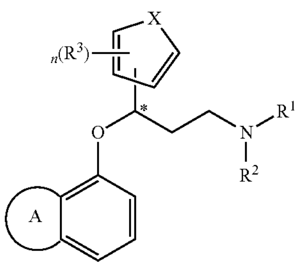

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

$R^3$ is hydrogen, halogen, substituted or unsubstituted $C_1$-$C_6$ alkyl, substituted or unsubstituted $C_3$-$C_7$ cycloalkyl;

n is 1, 2 or 3;

"*" represents that the configuration of the compound is racemic;

wherein, any one of the "substituted" means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the compound of formula Z has a structure of formula Z-1:

Z-1

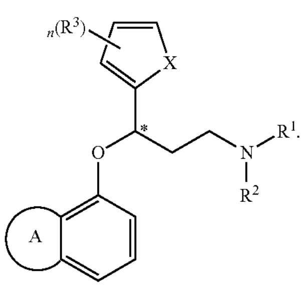

In another preferred embodiment, ring A is a substituted or unsubstituted 5-7 membered carbocyclic ring and a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, substituted or unsubstituted $C_1$-$C_6$ alkyl.

In another preferred embodiment, $R^3$ is hydrogen, halogen, substituted or unsubstituted $C_1$-$C_4$ alkyl.

In another preferred embodiment, the halogen is F, Cl, Br or I.

In another preferred embodiment, when n≥2, each $R^3$ is the same or different.

In another preferred embodiment, ring A is a substituted or unsubstituted 5-membered carbocyclic ring, a substituted or unsubstituted 6-membered carbocyclic ring, or a substituted or unsubstituted furan ring.

In another preferred embodiment, ring A is not a benzene ring.

In another preferred embodiment, ring A is

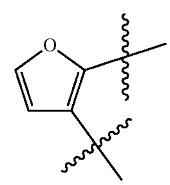

,

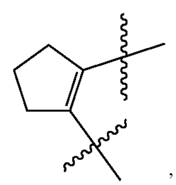

, or

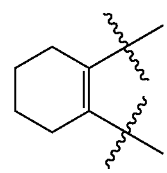

.

In another preferred embodiment, the connection structure between ring A and the adjacent benzene ring is:

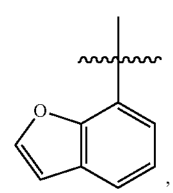

,

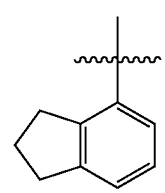

,

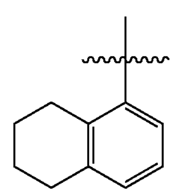

.

In another preferred embodiment, the structure of

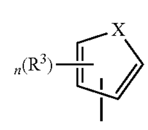

is:

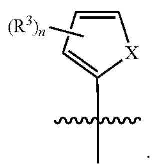

In another preferred embodiment, $R^1$ and $R^2$ are each independently hydrogen, methyl or ethyl.

In another preferred embodiment, $R^3$ is a hydrogen atom, a chlorine atom or a methyl.

In another preferred embodiment, n is 1.

In another preferred embodiment, A is a 5-membered carbocyclic ring, a 6-membered carbocyclic ring or a furan ring.

In another preferred embodiment, n is 1, 2 or 3.

In another preferred embodiment, X is S.

In another preferred embodiment, ring A is a furan ring.

In another preferred embodiment, the ring containing X is a thiophene ring.

In another preferred embodiment, the structure of the thiophene ring is

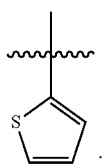 [SMILES: *c1cccs1]

In another preferred embodiment, the structure of the ring A acene ring is

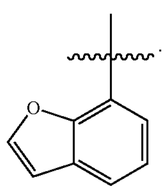 [SMILES: *c1cccc2ccoc12]

In the present invention, " 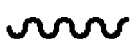 " is the linking site of the groups.

In another preferred embodiment, the compound of formula Z is selected from the group consisting of

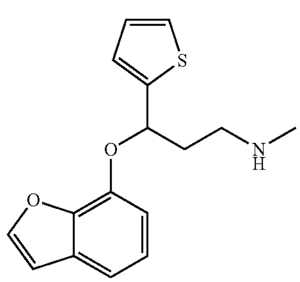

-continued

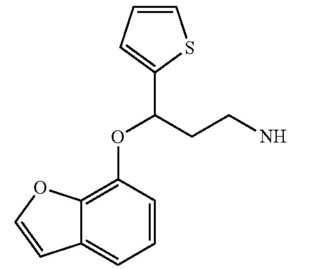

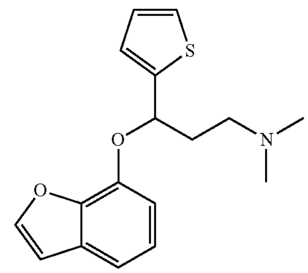

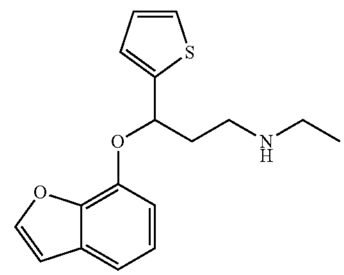

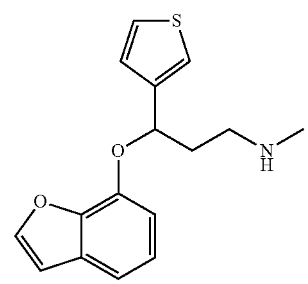

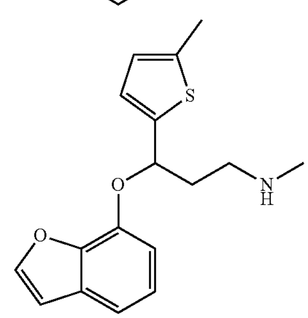

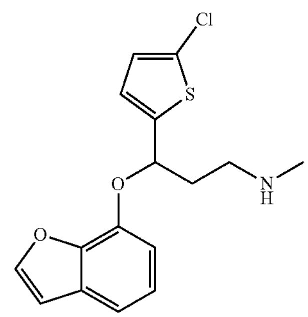

-continued

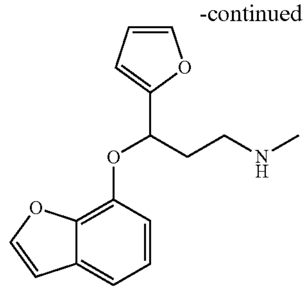

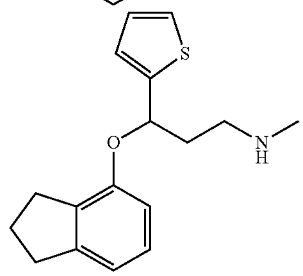

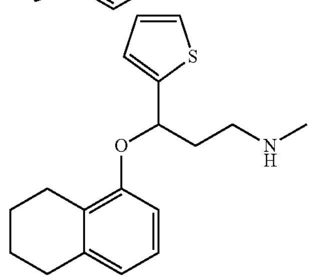

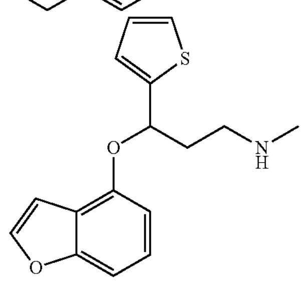

In another preferred embodiment, the disease related to transient receptor potential channel protein (TRPA1) is selected from the group consisting of pain, epilepsy, inflammation, respiratory disorder, pruritus, urinary tract disorder, inflammatory bowel disease, and combinations thereof. In another preferred embodiment, the pain is selected from the group consisting of acute pain, inflammatory pain, visceral pain, neurogenic pain, fibromyalgia, headache, nerve pain, mixed pain, cancer-induced pain, and combinations thereof.

In another preferred embodiment, the pain is postoperative pain.

In another preferred embodiment, the postoperative pain is postoperative pain following a surgical procedure.

In another preferred embodiment, the postoperative pain is post-operative wound pain.

In another preferred embodiment, the post-operative wound pain is selected from the group consisting of post-operative skin wound pain, post-operative muscle wound pain, and combinations thereof.

In another preferred embodiment, the post-operative wound pain is skin and muscle post-operative wound pain.

In another preferred embodiment, the acute pain is injury pain or postoperative pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscular tension pain.

In another preferred embodiment, the neuralgia is trigeminal neuralgia, diabetic pain, sciatica, or postherpetic neuralgia.

In another preferred embodiment, the acute pain is injury pain or postoperative pain.

In the second aspect of the present invention, it provides a use of a compound, or a pharmaceutically acceptable salt thereof, or a prodrug thereof, for (a) preparing a transient receptor potential channel protein (TRP) inhibitor; (b) manufacturing a medicament for preventing and/or treating diseases related to transient receptor potential channel protein (TRP);

wherein, the compound has the structure of formula I:

I

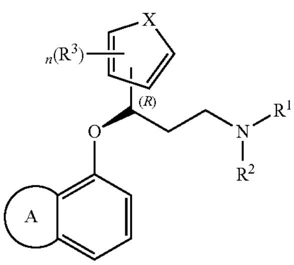

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

$R^3$ is hydrogen, halogen, substituted or unsubstituted $C_1$-$C_6$ alkyl, substituted or unsubstituted $C_3$-$C_7$ cycloalkyl;

n is 1, 2 or 3;

wherein, any one of the "substituted" means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the compound of formula I has a structure of formula I-1:

I-1

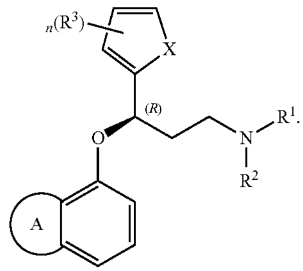

In another preferred embodiment, ring A is a substituted or unsubstituted 5-7 membered carbocyclic ring and a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, substituted or unsubstituted $C_1$-$C_6$ alkyl.

In another preferred embodiment, $R^3$ is hydrogen, halogen, substituted or unsubstituted $C_1$-$C_4$ alkyl.

In another preferred embodiment, the halogen is F, $C_1$, Br or I.

In another preferred embodiment, when n≥2, each $R^3$ is the same or different.

In another preferred embodiment, ring A is a substituted or unsubstituted 5-membered carbocyclic ring, a substituted or unsubstituted 6-membered carbocyclic ring, or a substituted or unsubstituted furan ring.

In another preferred embodiment, ring A is not a benzene ring.

In another preferred embodiment, ring A is

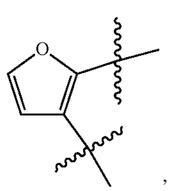

,

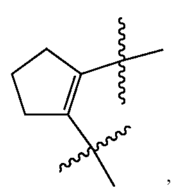

, or

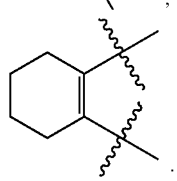

In another preferred embodiment, the connection structure between ring A and the adjacent benzene ring is:

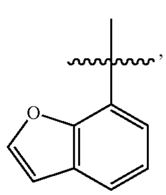

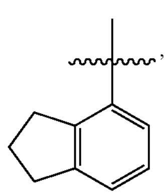

-continued

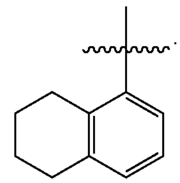

In another preferred embodiment, the structure of

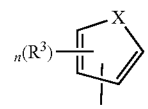

is:

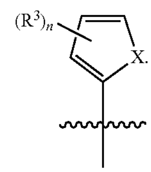

In another preferred embodiment, $R^1$ and $R^2$ are each independently hydrogen, methyl or ethyl.

In another preferred embodiment, $R^3$ is a hydrogen atom, a chlorine atom or a methyl.

In another preferred embodiment, n is 1.

In another preferred embodiment, A is a 5-membered carbocyclic ring, a 6-membered carbocyclic ring or a furan ring.

In another preferred embodiment, n is 1, 2 or 3.

In another preferred embodiment, X is S.

In another preferred embodiment, ring A is a furan ring.

In another preferred embodiment, the ring containing X is a thiophene ring.

In another preferred embodiment, the structure of the thiophene ring is

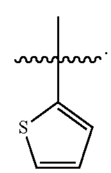 [SMILES: *c1cccs1]

In another preferred embodiment, the structure of the ring A acene ring is

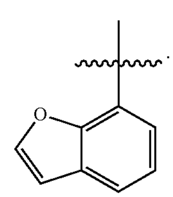 [SMILES: *c1cccc2ccoc12]

In another preferred embodiment, the compound is selected from the group consisting of:

I-1
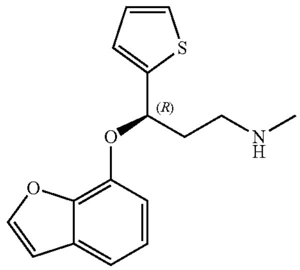
I-2
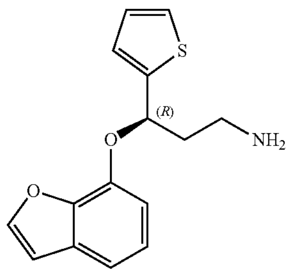
I-3
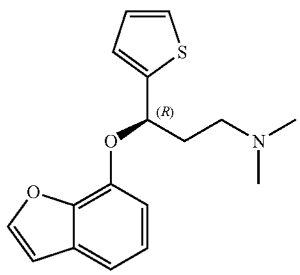
I-4
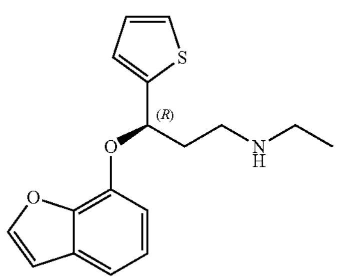
I-5
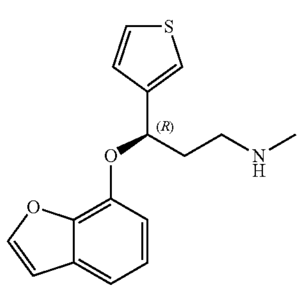
-continued
I-6
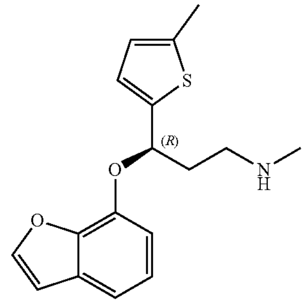
I-7
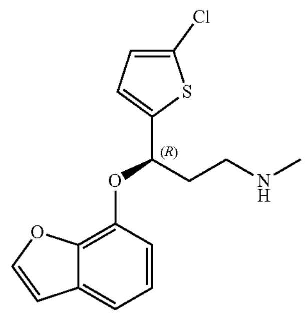
I-8
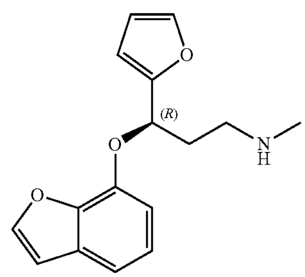
I-9
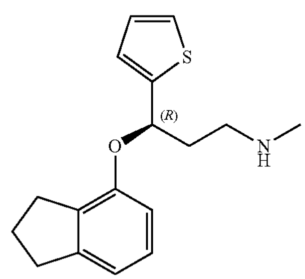
I-10
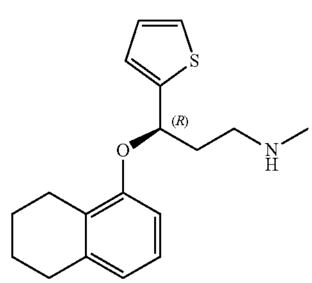

-continued

I-11

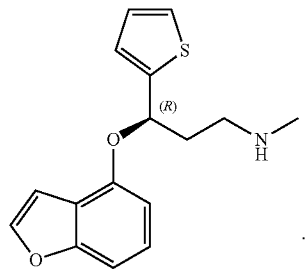

In another preferred embodiment, the transient receptor potential channel protein (TRP) is TRPA1.

In another preferred embodiment, the disease related to transient receptor potential channel protein (TRP) is selected from the group consisting of pain, epilepsy, inflammation, respiratory disorder, pruritus, urinary tract disorder, inflammatory bowel disease, and combinations thereof.

In another preferred embodiment, the pain is selected from the group consisting of acute pain, inflammatory pain, visceral pain, neurogenic pain, muscle fiber pain, headache, nerve pain, mixed pain, cancer-induced pain, and combinations thereof.

In another preferred embodiment, the acute pain is injury pain or postoperative pain.

In another preferred embodiment, the postoperative pain is postoperative pain following a surgical procedure.

In another preferred embodiment, the postoperative pain is post-operative wound pain.

In another preferred embodiment, the post-operative wound pain is selected from the group consisting of post-operative skin wound pain, post-operative muscle wound pain, and combinations thereof.

In another preferred embodiment, the post-operative wound pain is skin and muscle post-operative wound pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscular tension pain.

In another preferred embodiment, the neuralgia is trigeminal neuralgia, diabetic pain, sciatica, or postherpetic neuralgia.

In another preferred embodiment, the acute pain is injury pain or postoperative pain.

In the third aspect of the present invention, it provides a compound, or a pharmaceutically acceptable salt thereof, or a prodrug thereof, wherein the compound has a structure of formula Z:

Z

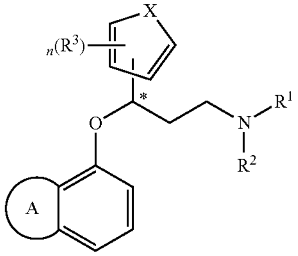

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

$R^3$ is hydrogen, halogen, substituted or unsubstituted $C_1$-$C_6$ alkyl, substituted or unsubstituted $C_3$-$C_7$ cycloalkyl;

n is 1, 2 or 3;

"*" represents that the configuration of the compound is racemic;

wherein, any one of the "substituted" means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the pharmaceutically acceptable salt of the compound of formula Z is a salt formed by the compound of formula Z and an acid selected from the group consisting of hydrochloric acid, mucic acid, D-glucuronic acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzyl sulfonic acid, benzenesulfonic acid, aspartic acid, glutamic acid, or combinations thereof.

In another preferred embodiment, the compound of formula Z has a structure of formula Z-1:

Z-1

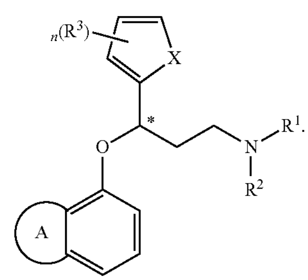

In another preferred embodiment, ring A is a substituted or unsubstituted 5-7 membered carbocyclic ring and a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, substituted or unsubstituted $C_1$-$C_6$ alkyl.

In another preferred embodiment, $R^3$ is hydrogen, halogen, substituted or unsubstituted $C_1$-$C_4$ alkyl.

In another preferred embodiment, the halogen is F, Cl, Br or I.

In another preferred embodiment, when n≥2, each $R^3$ is the same or different.

In another preferred embodiment, ring A is a substituted or unsubstituted 5-membered carbocyclic ring, a substituted or unsubstituted 6-membered carbocyclic ring, or a substituted or unsubstituted furan ring.

In another preferred embodiment, ring A is not a benzene ring.

In another preferred embodiment, ring A is

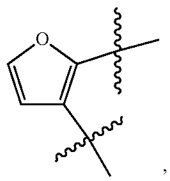
,
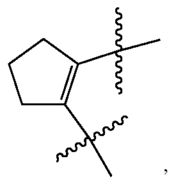
, or
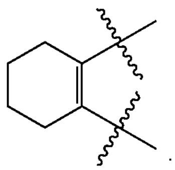

In another preferred embodiment, the connection structure between ring A and the adjacent benzene ring is:

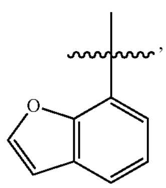
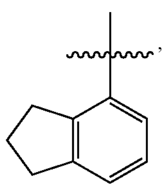
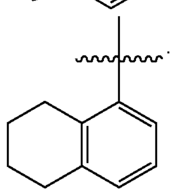

In another preferred embodiment, the structure of

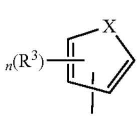

is:

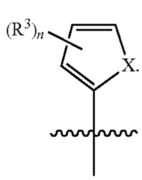

In another preferred embodiment, $R^1$ and $R^2$ are each independently hydrogen, methyl or ethyl.

In another preferred embodiment, $R^3$ is a hydrogen atom, a chlorine atom or a methyl.

In another preferred embodiment, n is 1.

In another preferred embodiment, A is a 5-membered carbocyclic ring, a 6-membered carbocyclic ring or a furan ring.

In another preferred embodiment, n is 1, 2 or 3.

In another preferred embodiment, X is S.

In another preferred embodiment, ring A is a furan ring.

In another preferred embodiment, the ring containing X is a thiophene ring.

In another preferred embodiment, the structure of the thiophene ring is

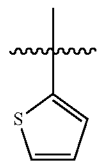

In another preferred embodiment, the structure of the ring A acene ring is

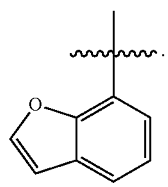 [SMILES: *c1cccc2ccoc12]

In the present invention, " 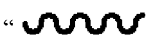 " is the linking site of the groups.

In another preferred embodiment, the compound is selected from the group consisting of:

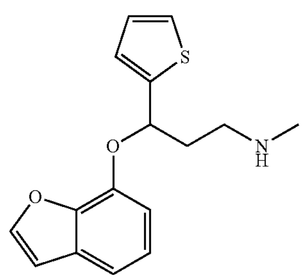
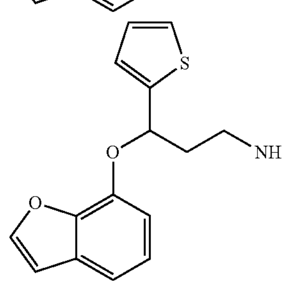

-continued

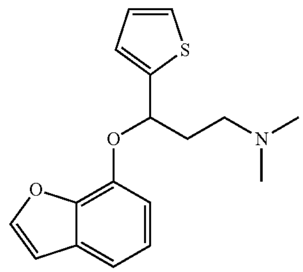

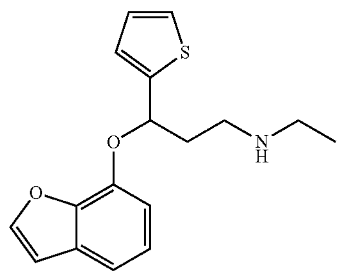

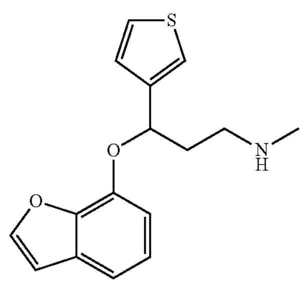

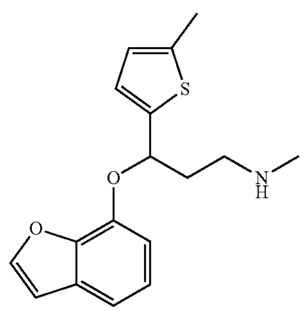

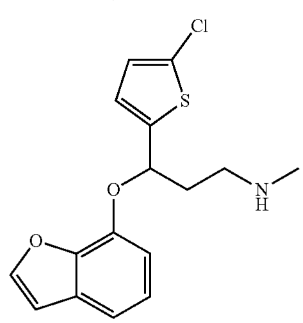

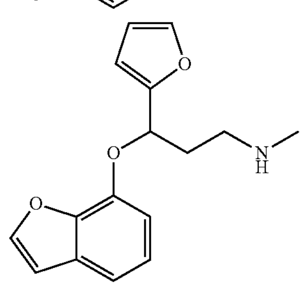

-continued

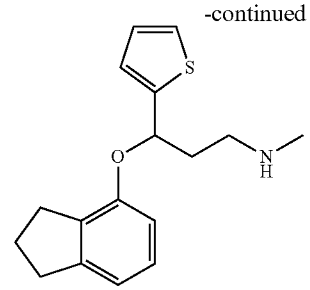

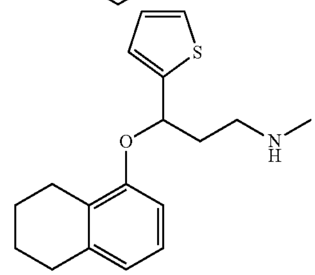

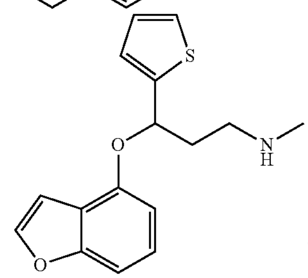

In the fourth aspect of the present invention, it provides a compound, or a pharmaceutically acceptable salt thereof, or a prodrug thereof, the compound has a structure of formula I:

I

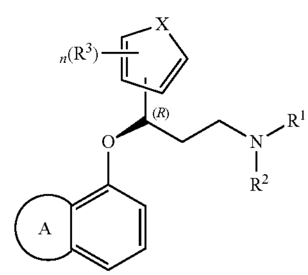

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

$R^3$ is hydrogen, halogen, substituted or unsubstituted $C_1$-$C_6$ alkyl, substituted or unsubstituted $C_3$-$C_7$ cycloalkyl;

n is 1, 2 or 3;

wherein, any one of the “substituted” means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the pharmaceutically acceptable salt of the compound of formula I is a salt formed by the compound of formula I and an acid selected from the group consisting of hydrochloric acid, mucic acid, D-glucuronic acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzyl sulfonic acid, benzenesulfonic acid, aspartic acid, glutamic acid, or combinations thereof.

In another preferred embodiment, the compound of formula I has a structure of formula I-1:

I-1

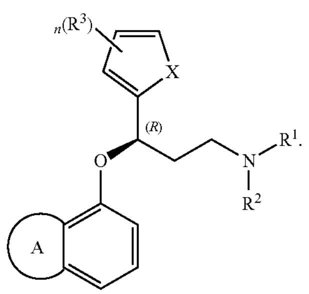

In another preferred embodiment, A is a substituted or unsubstituted 5-7 membered carbocyclic ring and a 5-7 membered heteroaromatic ring.

In another preferred embodiment, X is S or O.

In another preferred embodiment, $R^1$ and $R^2$ are each independently hydrogen or substituted or unsubstituted $C_1$-$C_3$ alkyl.

In another preferred embodiment, $R^3$ is hydrogen, halogen, substituted or unsubstituted $C_1$-$C_6$ alkyl.

In another preferred embodiment, $R^3$ is hydrogen, halogen, substituted or unsubstituted $C_1$-$C_4$ alkyl.

In another preferred embodiment, the halogen is F, Cl, Br or I.

In another preferred embodiment, when n≥2, each $R^3$ is the same or different.

In another preferred embodiment, A is a substituted or unsubstituted 5-membered carbocyclic ring, a substituted or unsubstituted 6-membered carbocyclic ring, or a substituted or unsubstituted furan ring.

In another preferred embodiment, ring A is not a benzene ring.

In another preferred embodiment, ring A is

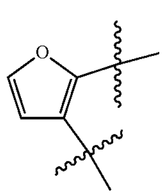
,
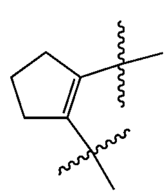
, or

-continued

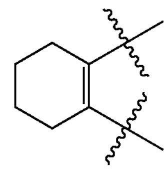
.

In another preferred embodiment, the connection structure between ring A and the adjacent benzene ring is:

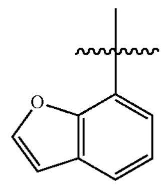
,
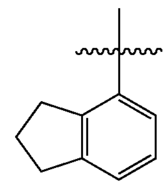
,
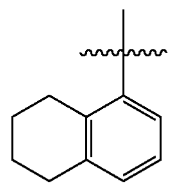
.

In another preferred embodiment, the structure of

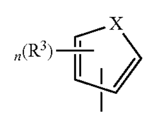

is:

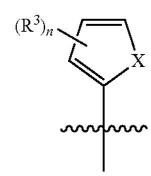
.

In another preferred embodiment, $R^1$ and $R^2$ are each independently hydrogen, methyl or ethyl.

In another preferred embodiment, $R^3$ is a hydrogen atom, a chlorine atom or a methyl.

In another preferred embodiment, n is 1.

In another preferred embodiment, A is a 5-membered carbocyclic ring, a 6-membered carbocyclic ring or a furan ring;

In another preferred embodiment, n is 1, 2 or 3.

In another preferred embodiment, X is S.

In another preferred embodiment, ring A is a furan ring.

In another preferred embodiment, the ring containing X is a thiophene ring.

In another preferred embodiment, the structure of the thiophene ring is

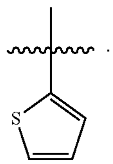 [SMILES: *c1cccs1]
In another preferred embodiment, the structure of the ring A acene ring is
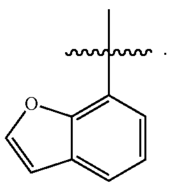
In the present invention, “ 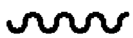 ” is the linking site of the groups.
In another preferred embodiment, the compound is selected from the group consisting of:
I-1
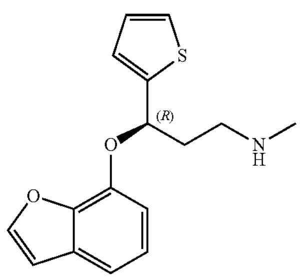
I-2
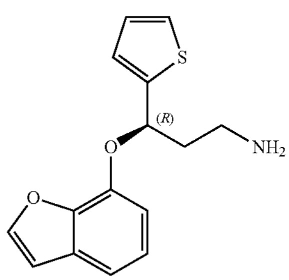
I-3
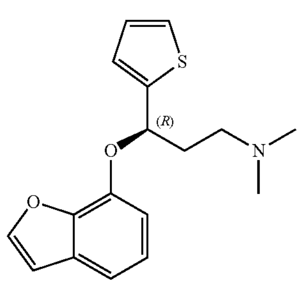
-continued
I-4
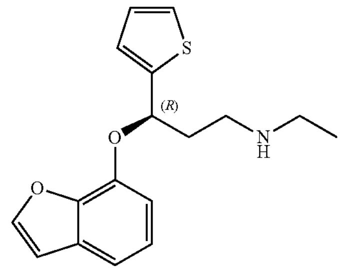
I-5
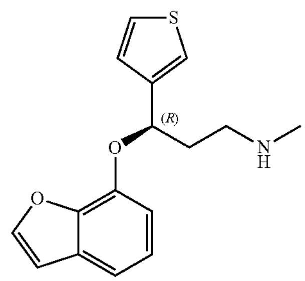
I-6
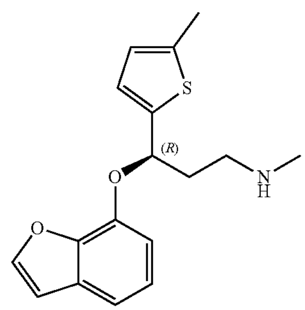
I-7
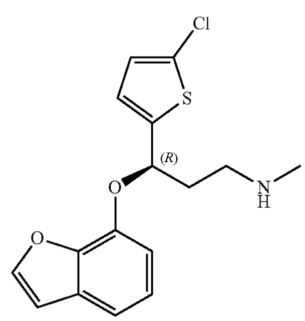
I-8
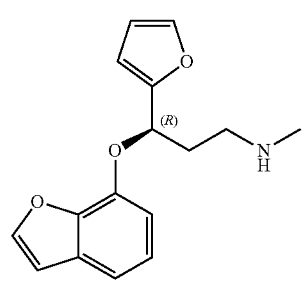

-continued

I-9

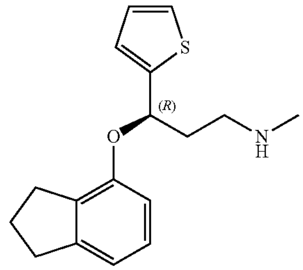

I-10

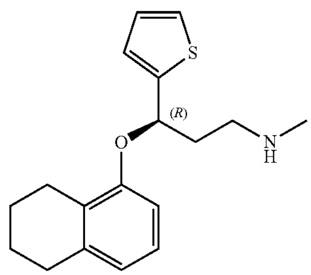

I-11

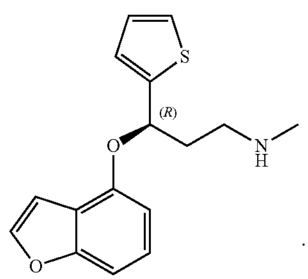

In the fifth aspect of the present invention, it provides a compound of formula A, or a pharmaceutically acceptable salt thereof, or a prodrug thereof,

A

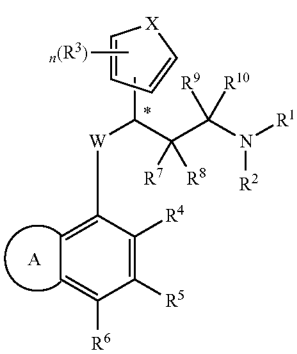

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

W is O or S;

$R^3$ is hydrogen, halogen, substituted or unsubstituted $C_1$-$C_6$ alkyl, substituted or unsubstituted $C_3$-$C_7$ cycloalkyl;

$R^4$, $R^5$, $R^6$, $R^7$, $R^8$, $R^9$ and $R^{10}$ are each independently hydrogen, substituted or unsubstituted $C_1$-$C_6$ alkyl, substituted or unsubstituted $C_3$-$C_7$ cycloalkyl;

n is 1, 2 or 3;

"*" represents that the configuration of the compound is racemic;

wherein, any one of the "substituted" means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the pharmaceutically acceptable salt of the compound of formula A is a salt formed by the compound of formula A and an acid selected from the group consisting of hydrochloric acid, mucic acid, D-glucuronic acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzyl sulfonic acid, benzenesulfonic acid, aspartic acid, glutamic acid, or combinations thereof.

In another preferred embodiment, in the compound of formula A, ring A, $R^1$, $R^2$, $R^3$, X, and n are each independently as described in the third aspect of the present invention.

In another preferred embodiment, W is O.

In another preferred embodiment, $R^4$, $R^5$, $R^6$, $R^7$, $R^8$, $R^9$ and $R^{10}$ are each independently hydrogen, substituted or unsubstituted $C_1$-$C_4$ alkyl, substituted or unsubstituted $C_3$-$C_6$ cycloalkyl.

In another preferred embodiment, $R^4$, $R^5$, $R^6$, $R^7$, $R^8$, $R^9$ and $R^{10}$ are each independently hydrogen.

In another preferred embodiment, the connection structure between ring A and the adjacent benzene ring is:

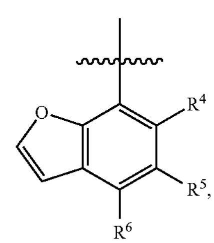

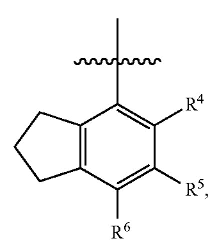

or

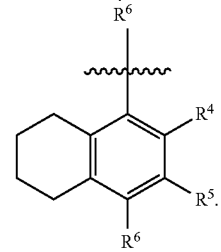

In another preferred embodiment, the compound of formula A is a compound of formula Z:

Z

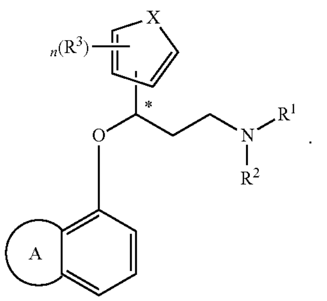

In another preferred embodiment, the compound of Formula Z is as described in the third aspect of the present invention.

In the sixth aspect of the present invention, it provides a compound of formula B, or a pharmaceutically acceptable salt thereof, or a prodrug thereof,

B

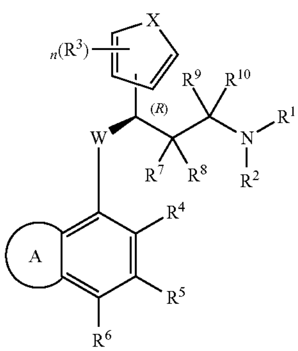

wherein:

ring A is a substituted or unsubstituted 5-7 membered carbocyclic ring, a substituted or unsubstituted 5-7 membered heterocyclic ring, a substituted or unsubstituted 5-7 membered heteroaromatic ring;

$R^1$ and $R^2$ are each independently hydrogen, substituted or unsubstituted $C_1$-$C_6$ alkyl, substituted or unsubstituted $C_3$-$C_7$ cycloalkyl;

X is an oxygen atom, a sulfur atom or a nitrogen atom;

W is O or S;

$R^3$ is hydrogen, halogen, substituted or unsubstituted $C_1$-$C_6$ alkyl, substituted or unsubstituted $C_3$-$C_7$ cycloalkyl;

$R^4$, $R^5$, $R^6$, $R^7$, $R^8$, $R^9$ and $R^{10}$ are each independently hydrogen, substituted or unsubstituted $C_1$-$C_6$ alkyl, substituted or unsubstituted $C_3$-$C_7$ cycloalkyl;

n is 1, 2 or 3;

"*" represents that the configuration of the compound is racemic;

wherein, any one of the "substituted" means that 1-4 hydrogen atoms (preferably 1, 2, 3, or 4) on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably a $C_5$ heteroaryl);

wherein, the heterocyclic ring, heteroaromatic ring and heteroaryl each independently have 1 to 3 (preferably 1, 2 or 3) heteroatoms selected from N, O and S.

In another preferred embodiment, the pharmaceutically acceptable salt of the compound of formula B is a salt formed by the compound of formula B and an acid selected from the group consisting of hydrochloric acid, mucic acid, D-glucuronic acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzyl sulfonic acid, benzenesulfonic acid, aspartic acid, glutamic acid, or combinations thereof.

In another preferred embodiment, in the compound of formula A, ring A, $R^1$, $R^2$, $R^3$, X, and n are each independently as described in the fourth aspect of the present invention.

In another preferred embodiment, W is O.

In another preferred embodiment, $R^4$, $R^5$, $R^6$, $R^7$, $R^8$, $R^9$ and $R^{10}$ are each independently hydrogen, substituted or unsubstituted $C_1$-$C_4$ alkyl, substituted or unsubstituted $C_3$-$C_6$ cycloalkyl.

In another preferred embodiment, $R^4$, $R^5$, $R^6$, $R^7$, $R^8$, $R^9$ and $R^{10}$ are each independently hydrogen.

In another preferred embodiment, the connection structure between ring A and the adjacent benzene ring is:

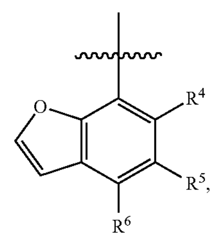

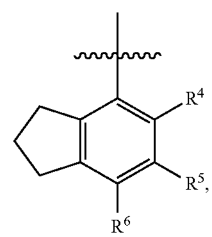

or

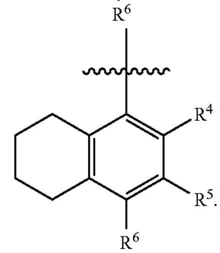

In another preferred embodiment, the compound of Formula B is a compound having a structural of Formula I:

I

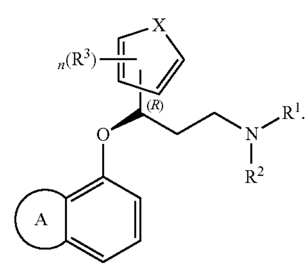

In another preferred embodiment, the compound of Formula I is as described in the fourth aspect of the present invention.

In the seventh aspect of the present invention, it provides a pharmaceutical composition comprising the compound as described in the third aspect of the present invention, or the pharmaceutically acceptable salt thereof, or the prodrug thereof, and/or the compound as described in the fourth aspect of the present invention, or the pharmaceutically acceptable salt thereof, or the prodrug thereof; and pharmaceutically acceptable carriers.

In the eighth aspect of the present invention, it provides a pharmaceutical composition comprising the compound as described in the fifth aspect of the present invention, or the pharmaceutically acceptable salt thereof, or the prodrug thereof, and/or the compound as described in the sixth aspect of the present invention, or the pharmaceutically acceptable salt thereof, or the prodrug thereof; and pharmaceutically acceptable carriers.

In the ninth aspect of the present invention, it provides a use of the compound of formula A as described in the fifth aspect of the present invention, or the pharmaceutically acceptable salt thereof, or the prodrug thereof, or the compound of formula B as described in the sixth aspect of the present invention, or the pharmaceutically acceptable salt thereof, or the prodrug thereof for (a) preparing a transient receptor potential channel protein (TRPA1) inhibitor; (b) manufacturing a medicament for preventing and/or treating diseases related to transient receptor potential channel protein (TRPA1). In another preferred embodiment, the transient receptor potential channel protein (TRP) is TRPA1.

In another preferred embodiment, the disease related to transient receptor potential channel protein (TRP) is as described in the second aspect of the present invention.

In the tenth aspect of the present invention, it provides a method for preparing the compound as described in the fourth aspect of the present invention, or the pharmaceutically acceptable salt thereof, or the prodrug thereof, wherein the method comprises the steps of: in an inert solvent, reacting intermediate II with the $R^1$—NH—$R^2$ compound to form the compound:

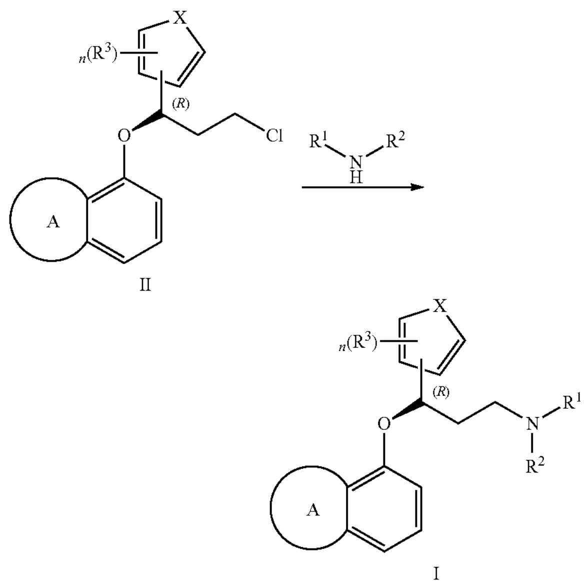

wherein X, A, $R^1$, $R^2$, $R^3$ and n are as described in the fourth aspect of the present invention.

In another preferred embodiment, the method comprises the steps of:

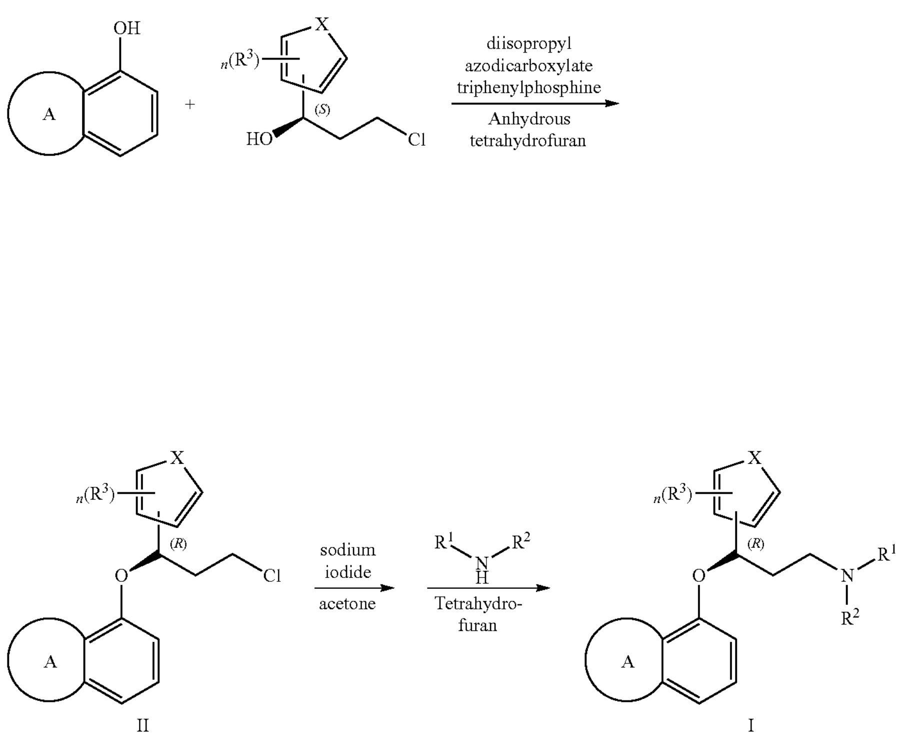

-continued

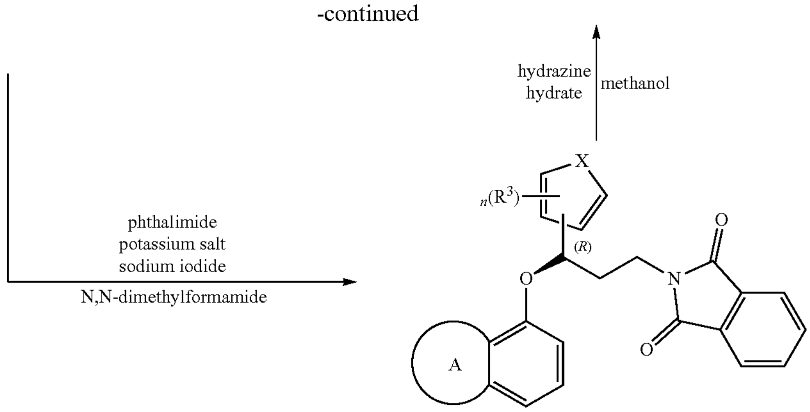

III wherein X, A, $R^1$, $R^2$, $R^3$ and n are as described in the fourth aspect of the present invention:

(a) reacting compound

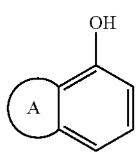

with (S)-1-($_n$($R^3$)-five-membered heteroaryl)-3-chloro-propanol in the presence of a condensation agent in an inert solvent to form Intermediate II;

(b) performing any reaction selected from the follows to form compound I:

(b-1) reacting intermediate II with $R^1$—NH—$R^2$ in an inert solvent to form compound I;

(b-2) in an inert solvent, the intermediate II is reacted with the potassium salt of phthalimide to form intermediate III, which undergoes hydrazinolysis to form compound I.

In the eleventh aspect of the present invention, it provides an intermediate, wherein the intermediate has the structure of formula II or formula III:

II

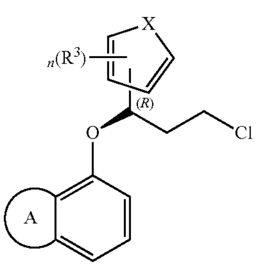

or

-continued

III

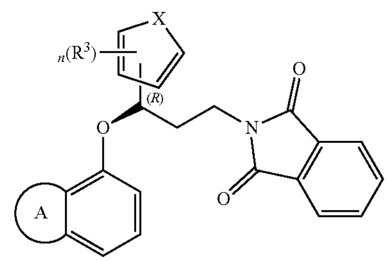

wherein X, A, $R^3$ and n are as described in the fourth aspect of the present invention.

In the twelfth aspect of the present invention, it provides a method for preparing the intermediate as described in the seventh aspect of the present invention,

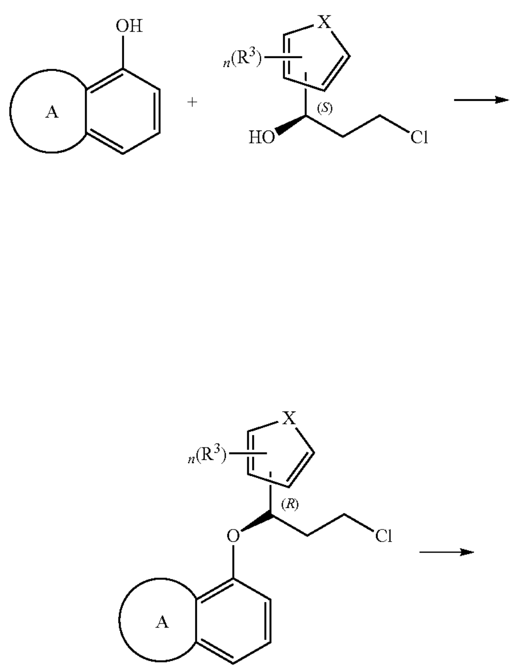

II

-continued

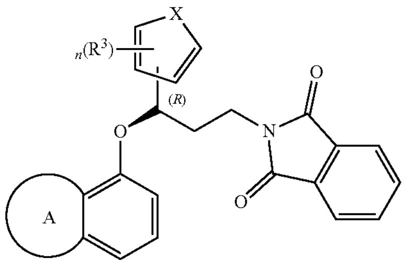

III wherein X, A, $R^3$ and n are as described in the fourth aspect of the present invention:

(1) the method comprises the steps of:

(i) reacting the compound

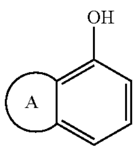

with (S)-1-($_n(R^3)$-five-membered heteroaryl)-3-chloropropanol in an inert solvent in the presence of a condensation agent to form Intermediate II;

or (2) the method comprises the steps of:

(i) reacting the compound

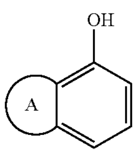

with (S)-1-($_n(R^3)$-five-membered heteroaryl)-3-chloropropanol in an inert solvent in the presence of a condensation agent to form Intermediate II; and (ii) reacting Intermediate II with the potassium salt of phthalimide in an inert solvent to form Intermediate III.

In another preferred embodiment, the intermediate is selected from the group consisting of:

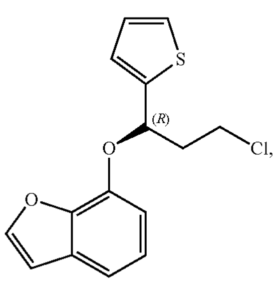

-continued

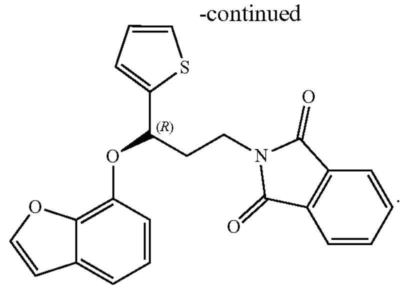

In the thirteenth aspect of the present invention, it provides a non-therapeutic and non-diagnostic in vitro method for inhibiting transient receptor potential channel protein activity, wherein the method comprises the steps of: in a culture system in vitro, contacting the transient receptor potential channel protein or the cell expressing the protein with the compound as described in the third, fourth, fifth and/or sixth aspect of the present invention, or the pharmaceutically acceptable salt thereof, or the prodrug thereof, thereby inhibiting the activity of the transient receptor potential channel protein.

In the fourteenth aspect of the present invention, it provides a method for inhibiting transient receptor potential channel protein or preventing and/or treating diseases related to transient receptor potential channel protein (TRP), wherein the method comprises the steps of: administrating the compound as described in the third, fourth, fifth and/or sixth aspect of the present invention, or the pharmaceutically acceptable salt thereof, or the prodrug thereof to a subject in need thereof.

In another preferred embodiment, the subject includes humans and non-human mammals (rodents, rabbits, monkeys, domestic animals, dogs, cats, etc.).

In the fifteenth aspect of the present invention, it provides a compound, or a pharmaceutically acceptable salt thereof, or a prodrug thereof, wherein the compound has a structure of formula G:

G

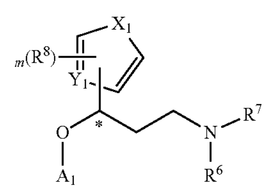

wherein:

$A_1$ is

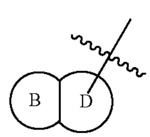

or

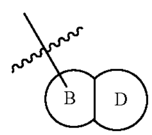

group; wherein, ring B is substituted or unsubstituted 5-7 membered carbocyclic ring, substituted or unsubstituted 5-7 membered heterocyclic ring, substituted or unsubstituted 5-7 membered heteroaryl, substituted or unsubstituted $C_6$-$C_{12}$ aryl; ring D is substituted or unsubstituted 5-7 membered heteroaryl, substituted or unsubstituted $C_6$-$C_{12}$ aryl; and when A1 is a substituted or unsubstituted aromatic structure, A1 contains 1-3 heteroatoms selected from N, O and S;

wherein the heterocyclic ring or heteroaryl contains 1-3 heteroatoms selected from N, O and S;

$R^6$ and $R^7$ are each independently hydrogen, substituted or unsubstituted $C_1$-$C_6$ alkyl, substituted or unsubstituted $C_3$-$C_7$ cycloalkyl, substituted or unsubstituted $C_2$-$C_4$ acyl, substituted or unsubstituted $C_2$-$C_6$ ester, or $R^6$, $R^7$ and their linking N atom form a substituted or unsubstituted $C_3$-$C_7$ heterocycloalkyl; wherein, the heterocycloalkyl contains 1-2 N atoms and 0-1 O or S atom;

$X_1$ is a carbon atom, an oxygen atom, a sulfur atom or a nitrogen atom;

$Y_1$ is a carbon atom or a nitrogen atom;

at least one of $X_1$ and $Y_1$ is a heteroatom;

$R^8$ is hydrogen, halogen, substituted or unsubstituted $C_1$-$C_6$ alkyl, substituted or unsubstituted $C_3$-$C_7$ cycloalkyl;

m is 1, 2, 3, 4 or 5;

"*" represents a chiral carbon atom, and the absolute configuration of the chiral carbon atom is R-type and S-type;

wherein, any one of the "substituted" means that one to four (preferably 1, 2, 3) hydrogen atoms on the group are substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxyl, $C_2$-$C_4$ ester, $C_2$-$C_4$ amide, $C_1$-$C_6$ alkoxy, $C_1$-$C_6$ haloalkyloxy, benzyl, five- or six-membered aryl or heteroaryl (preferably $C_6$ aryl or $C_5$ heteroaryl).

In the present invention, it should be understood that in the compound of formula G, "*" represents a chiral carbon atom, and the absolute configuration of the chiral carbon atom being R-type and S-type refers to the racemic form.

In another preferred embodiment, $A_1$ is

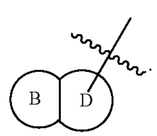

In another preferred embodiment, $A_1$ is not a naphthalene ring.

In another preferred embodiment, $A_1$ is a substituted or unsubstituted $C_6$-$C_{12}$ bicyclic heteroaryl, a substituted or unsubstituted 5-6 membered heterocycle phenyl, a substituted or unsubstituted 5-6 membered heterocycle5-6 membered heteroaryl, or substituted or unsubstituted $C_6$-$C_{12}$ benzoalicyclic group.

In another preferred embodiment, the $C_6$-$C_{12}$ bicyclic heteroaryl is quinolinyl, isoquinolinyl, phthalimidyl, benzofuranyl, benzothienyl, indolyl, benzooxazolyl, benzothiazolyl, quinoxalinyl, imidazopyridyl or benzimidazolone.

In another preferred embodiment, the $C_6$-$C_{12}$ benzoalicyclic group includes indanyl, tetrahydronaphthyl or dihydronaphthyl.

In another preferred embodiment, $A_1$ is substituted or unsubstituted benzofuranyl, benzothienyl, or indanyl.

In another preferred embodiment, at least one of $X_1$ and $Y_1$ is a heteroatom.

In another preferred embodiment, $X_1$ is S or O.

In another preferred embodiment, $X_1$ is S.

In another preferred embodiment, the heteroaryl contains 1-3 heteroatoms selected from N, O, or S.

In another preferred embodiment, the substituted refers to being substituted by one to four substituents (preferably 1, 2, or 3) selected from the group consisting of: $C_1$-$C_3$ alkyl, $C_3$-$C_7$ cycloalkyl, $C_1$-$C_3$ haloalkyl, halogen, nitro, cyano, hydroxyl, carboxy, $C_2$-$C_4$ ester, $C_2$-$C_4$ amide, $C_1$-$C_4$ alkoxy, $C_1$-$C_6$ haloalkoxy, benzyl, five-membered or six-membered aryl or heteroaryl (preferably $C_6$ aryl or $C_5$ heteroaryl).

In another preferred embodiment, $A_1$ is a substituted or unsubstituted $C_6$-$C_{12}$ bicyclic heteroaryl, a substituted or unsubstituted 5-6 membered heterocycle phenyl, a substituted or unsubstituted 5-6 membered heterocycle 5-6 membered heteroaryl, or substituted or unsubstituted $C_6$-$C_{12}$ benzoalicyclic group.

In another preferred embodiment, $R^6$ and $R^7$ are each independently a hydrogen atom, a $C_1$-$C_3$ alkyl, a $C_2$-$C_4$ acyl; or $R^6$, $R^7$ and their linking N atom form a tetrahydropyrrolyl substituted with carboxyl or a $C_2$-$C_4$ ester.

In another preferred embodiment, $R^8$ is a hydrogen atom, halogen, substituted or unsubstituted $C_1$-$C_3$ alkyl.

In another preferred embodiment, $A_1$ is quinolinyl, isoquinolinyl, phthalimidyl, benzofuranyl, benzothienyl, indolyl, benzoxazolyl, benzothiazolyl, quinoxalinyl, imidazopyridyl, benzimidazolone, indanyl, tetrahydronaphthyl or dihydronaphthyl.

In another preferred embodiment, $R^6$ and $R^7$ are each independently hydrogen atom, methyl, acetyl, or $R^6$, $R^7$ and their linking N atom form a proline group or a proline methyl ester group.

In another preferred embodiment, $R^8$ is a hydrogen atom, a chlorine atom, or a methyl.

In another preferred embodiment, the compound of formula G is selected from the group consisting of:

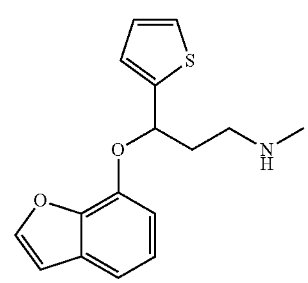

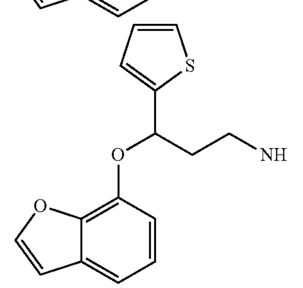

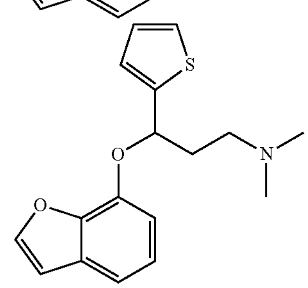

-continued

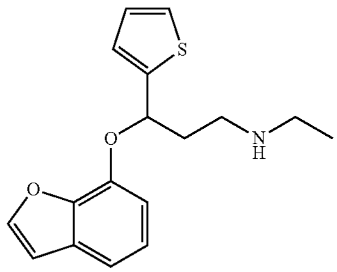

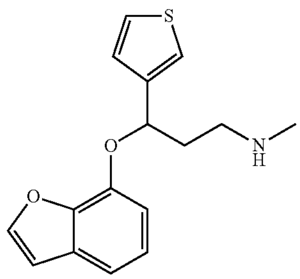

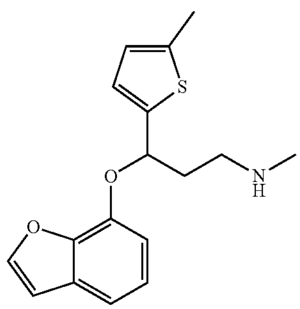

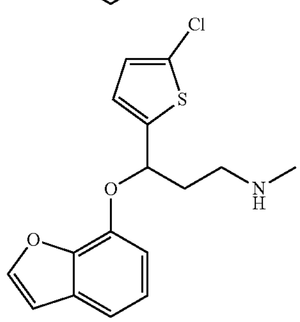

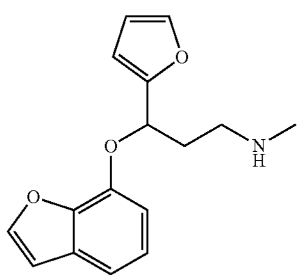

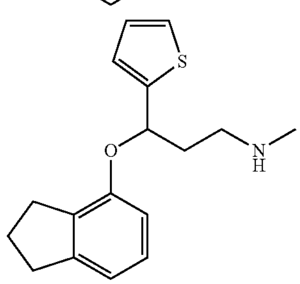

-continued

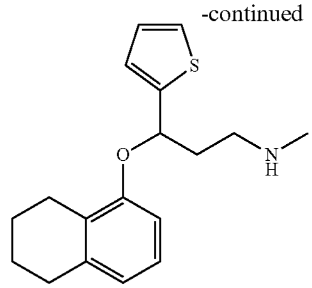

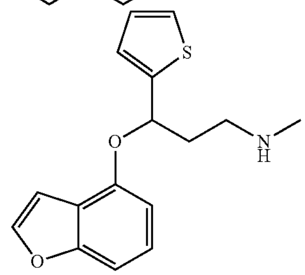

In the sixteenth aspect of the present invention, it provides a use of the compound of formula G as described in the fifteenth aspect of the present invention for (a) preparing a transient receptor potential channel protein (TRP) inhibitors; (b) manufacturing a medicament for preventing and/or treating diseases related to transient receptor potential channel protein (TRP).

In another preferred embodiment, the transient receptor potential channel protein (TRP) is TRPA1.

In another preferred embodiment, the disease related to transient receptor potential channel protein (TRP) is selected from the group consisting of pain, epilepsy, inflammation, respiratory disorder, pruritus, urinary tract disorder, or inflammatory bowel disease.

In another preferred embodiment, the pain includes acute inflammatory pain, chronic inflammatory pain, visceral pain, neurogenic pain, fibromyalgia, headache, neuralgia, or cancer-induced pain.

In another preferred embodiment, the disease related to transient receptor potential channel protein (TRP) is selected from the group consisting of pain, epilepsy, inflammation, respiratory disorder, pruritus, urinary tract disorder, inflammatory bowel disease, and combinations thereof.

In another preferred embodiment, the pain is selected from the group consisting of acute pain, inflammatory pain, visceral pain, neurogenic pain, fibromyalgia, headache, nerve pain, mixed pain, cancer-induced pain, and combinations thereof.

In another preferred embodiment, the acute pain is injury pain or postoperative pain.

In another preferred embodiment, the postoperative pain is postoperative pain following a surgical procedure.

In another preferred embodiment, the postoperative pain is post-operative wound pain. In another preferred embodiment, the post-operative wound pain is selected from the group consisting of post-operative skin wound pain, post-operative muscle wound pain, and combinations thereof.

In another preferred embodiment, the post-operative wound pain is skin and muscle post-operative wound pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscular tension pain.

In another preferred embodiment, the neuralgia is trigeminal neuralgia, diabetic pain, sciatica, or postherpetic neuralgia.

In the seventeenth aspect of the present invention, it provides a method for preparing a compound of formula G, or a pharmaceutically acceptable salt thereof, or a prodrug thereof as described in the fifteenth aspect of the present invention, wherein the method comprises the steps: in an inert solvent, reacting intermediate G-1 with $R^6$—NH—$R^7$ compound to form the compound:

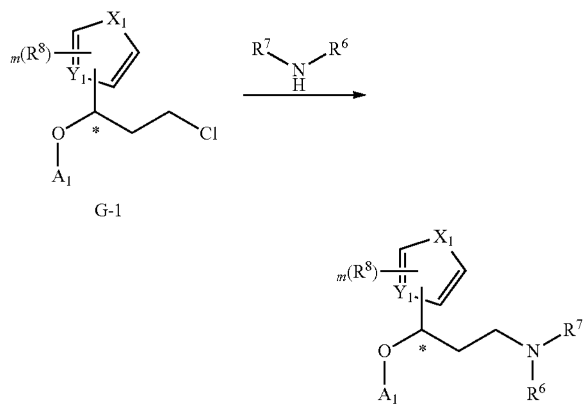

G-1

G wherein $X_1$, $Y_1$, $A_1$, $R^6$, $R^7$, $R^8$ and "*" are as described in the fifteenth aspect of the present invention.

In the eighteenth aspect of the present invention, it provides a hydrochloride of the compound of formula I-1 or a crystal form A thereof,

I-1

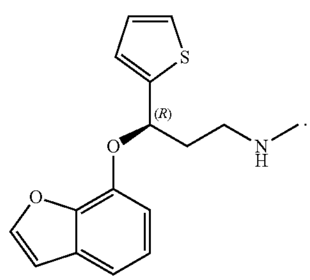

In another preferred embodiment, in the crystal form A of the hydrochloride of the compound I-1, the molecular molar ratio of the compound of Formula I-1 to hydrochloric acid is 4:1, 3:1, 2:1, 1:1, 1:2, 1:3 or 4:1.

In another preferred embodiment, the crystal form A of the hydrochloride of the compound of Formula I-1 is an anhydrous crystal form.

In another preferred embodiment, the X-ray powder diffraction pattern of the crystal form A of the hydrochloride of the compound of Formula I-1 has characteristic peaks at 20 angles of 18.173±0.2°, 22.084±0.2°, and 22.794±0.2°.

In another preferred embodiment, the crystal form A of the hydrochloride of the compound of Formula I-1 further has characteristic peaks at one or more 20 values selected from 16.734±0.2°, 21.156±0.2°, and 23.761±0.2°.

In another preferred embodiment, the crystal form A of the hydrochloride of the compound of Formula I-1 further has characteristic peaks at one or more 20 values selected from 17.092±0.2°, 21.649±0.2°, 25.298±0.2°, 28.099±0.2°.

In another preferred embodiment, the crystal form A of the hydrochloride of the compound of Formula I-1 further has characteristic peaks at one or more 20 values selected from 10.003±0.2°, 26.640±0.2°, 28.615±0.2°, 28.813±0.2°.

In another preferred embodiment, the crystal form A of the hydrochloride of the compound of Formula I-1 further has characteristic peaks at one or more 20 values selected from 10.003±0.2°, 16.734±0.2°, 17.092±0.2°, 18.173±0.2°, 21.156±0.2°, 21.649±0.2°, 22.084±0.2°, 26.640±0.2°.

In another preferred embodiment, the crystal form A of the hydrochloride of the compound of Formula I-1 further has characteristic peaks at one or more 20 values selected from 11.171±0.2°, 15.987±0.2°, 18.849±0.2°, 20.681±0.2°, 25.967±0.2°, 27.273±0.2°, 29.501±0.2°, 30.118±0.2°, 30.513±0.2°, 32.522±0.2°, 33.274±0.2°, 34.081±0.2°, 35.815±0.2°, 37.553±0.2°, 40.018±0.2°, 42.927±0.2°, 44.129±0.2.

In another preferred embodiment, the crystal form A of the hydrochloride of the compound of Formula I-1 further has characteristic peaks at one or more 20 values selected from 10.003±0.2°, 11.171±0.2°, 15.987±0.2°, 16.734±0.2°, 17.092±0.2°, 18.849±0.2°, 20.681±0.2°, 21.156±0.2°, 21.649±0.2°, 23.761±0.2°, 25.298±0.2°, 25.967±0.2°, 26.640±0.2°, 27.273±0.2°, 28.099±0.2°, 28.615±0.2°, 28.813±0.2°, 29.501±0.2°, 30.118±0.2°, 30.513±0.2°, 32.522±0.2°, 33.274±0.2°, 34.081±0.2°, 35.815±0.2°, 37.553±0.2°, 40.018±0.2°, 42.927±0.2°, 44.129±0.2.

In another preferred embodiment, the crystal form A of the hydrochloride of the compound of Formula I-1 has characteristic peaks at one or more 20 values selected from 10.003±0.2°, 11.171±0.2°, 15.987±0.2°, 16.734±0.2°, 17.092±0.2°, 18.173±0.2°, 18.849±0.2°, 20.681±0.2°, 21.156±0.2°, 21.649±0.2°, 22.084±0.2°, 22.794±0.2°, 23.761±0.2°, 25.298±0.2°, 25.967±0.2°, 26.640±0.2°, 27.273±0.2°, 28.099±0.2°, 28.615±0.2°, 28.813±0.2°, 29.501±0.2°, 30.118±0.2°, 30.513±0.2°, 32.522±0.2°, 33.274±0.2°, 34.081±0.2°, 35.815±0.2°, 37.553±0.2°, 40.018±0.2°, 42.927±0.2°, 44.129±0.2.

In another preferred embodiment, the X-ray powder diffraction pattern of the crystal form A of the hydrochloride has characteristic peaks and peak intensities at one or more 2θ values selected from the group consisting of:

| 2θ value | D value | Relative Intensity % |
|---|---|---|
| 10.003 | 8.8355 | 28.3 |
| 11.171 | 7.9137 | 12.8 |
| 15.987 | 5.5392 | 15.2 |
| 16.734 | 5.2936 | 51.9 |
| 17.092 | 5.1836 | 35.7 |
| 18.173 | 4.8774 | 100.0 |
| 18.849 | 4.7041 | 12.7 |
| 20.681 | 4.2913 | 13.6 |
| 21.156 | 4.1961 | 65.2 |
| 21.649 | 4.1017 | 35.3 |
| 22.084 | 4.0217 | 71.9 |
| 22.794 | 3.8981 | 91.8 |
| 23.761 | 3.7416 | 65.0 |
| 25.298 | 3.5177 | 46.3 |
| 25.967 | 3.4285 | 11.5 |
| 26.640 | 3.3433 | 29.2 |
| 27.273 | 3.2672 | 16.9 |
| 28.099 | 3.1730 | 35.7 |
| 28.615 | 3.1170 | 33.1 |

-continued

| 2θ value | D value | Relative Intensity % |
|---|---|---|
| 28.813 | 3.0959 | 25.2 |
| 29.501 | 3.0253 | 10.4 |
| 30.118 | 2.9647 | 12.1 |
| 30.513 | 2.9272 | 13.2 |
| 32.522 | 2.7508 | 18.4 |
| 33.274 | 2.6904 | 12.4 |
| 34.081 | 2.6285 | 13.2 |
| 35.815 | 2.5051 | 13.4 |
| 37.553 | 2.3931 | 9.6 |
| 40.018 | 2.2512 | 8.2 |
| 42.927 | 2.1051 | 10.6 |
| 44.129 | 2.0505 | 9.0. |

In another preferred embodiment, the crystal form A of the hydrochloride of the compound of Formula I-1 has X-ray powder diffraction characteristic peaks substantially as shown in FIG. 7.

In another preferred embodiment, the differential scanning calorimetry (DSC) pattern of the crystal form A of the hydrochloride of the compound of Formula I-1 begins to appear endothermic peaks upon being heated to 142.30° C. (preferably ±4° C., ±3° C., ±2° C. or ±1° C.).

In another preferred embodiment, the differential scanning calorimetry (DSC) pattern of the crystal form A of the hydrochloride of the compound of Formula I-1 is substantially as shown in FIG. 8.

In another preferred embodiment, the thermogravimetric analysis (TGA) pattern of the crystal form A of the hydrochloride of the compound of Formula I-1 has a weight loss of about 0.9827% (preferably ±0.1%, ±0.2%, ±0.3%, ±0.4%, or ±0.5%) upon being heated to 168.01° C.

In another preferred embodiment, the thermogravimetric analysis (TGA) pattern of the crystal form A of the hydrochloride is substantially as shown in FIG. 9.

In the nineteenth aspect of the present invention, it provides a method for preparing the crystal form A of the hydrochloride of the compound of Formula I-1 as described in the eighteenth aspect of the present invention, wherein the method comprises the steps of:

(a) after mixing the compound of formula I-1 with an organic solvent, adding hydrochloric acid dropwise at 5~15° C. to adjust the pH of the system to 6-8, a solid was precipitated during the reaction, and filtering to obtain the crystal form A of the hydrochloride of the compound of Formula I-1.

In another preferred embodiment, in step (a), the organic solvent comprises ethyl acetate.

In another preferred embodiment, in step (a), the hydrochloric acid is concentrated hydrochloric acid.

In another preferred embodiment, in step (a), the pH of the system is 6.5-7.5, preferably 7.0.

In another preferred embodiment, in step (a), the reaction time is 3-8 min, preferably 5 min.

In another preferred embodiment, in step (a), the reaction is reacted under stirring conditions.

In another preferred embodiment, in step (a), the hydrochloric acid is slowly added.

In another preferred embodiment, in step (a), the weight-volume ratio (kg:L) of the compound of Formula I-1 to the organic solvent is 0.2-2: 2-30, preferably 0.4-1.0:5-18, more preferably 0.5-0.9:8-15.

In another preferred embodiment, in step (a), after the solid was precipitated, the crystal form A of the hydrochloride of the compound of Formula I-1 was obtained by drying at 40-45° C.

In the twentieth aspect of the present invention, it provides a pharmaceutical composition comprising the crystal form A of the hydrochloride of the compound of Formula I-1 as described in the eighteenth aspect of the present invention; and pharmaceutically acceptable carriers.

In the twenty-first aspect of the present invention, it provides a use of the crystal form A of the hydrochloride of the compound of Formula I-1 as described in the eighteenth aspect of the present invention for (a) preparing transient receptor potential channel protein (TRP) inhibitors; (b) manufacturing a medicament for preventing and/or treating diseases related to transient receptor potential channel protein (TRP).

In another preferred embodiment, the transient receptor potential channel protein (TRP) is TRPA1.

In another preferred embodiment, the disease related to transient receptor potential channel protein (TRP) is selected from the group consisting of pain, epilepsy, inflammation, respiratory disorder, pruritus, urinary tract disorder, inflammatory bowel disease, and combinations thereof.

In another preferred embodiment, the pain is selected from the group consisting of acute pain, inflammatory pain, visceral pain, neurogenic pain, muscle fiber pain, headache, nerve pain, mixed pain, cancer-induced pain, and combinations thereof.

In another preferred embodiment, the acute pain is injury pain or postoperative pain.

In another preferred embodiment, the postoperative pain is postoperative pain following a surgical procedure.

In another preferred embodiment, the postoperative pain is post-operative wound pain. In another preferred embodiment, the post-operative wound pain is selected from the group consisting of post-operative skin wound pain, post-operative muscle wound pain, and combinations thereof.

In another preferred embodiment, the post-operative wound pain is skin and muscle post-operative wound pain.

In another preferred embodiment, the inflammatory pain is chronic inflammatory pain.

In another preferred embodiment, the inflammatory pain is osteoarthritis pain or rheumatoid arthritis pain.

In another preferred embodiment, the headache is migraine or muscular tension pain.

In another preferred embodiment, the neuralgia is trigeminal neuralgia, diabetic pain, sciatica, or postherpetic neuralgia.

In another preferred embodiment, the acute pain is injury pain or postoperative pain.

In the twenty-second aspect of the present invention, it provides a non-therapeutic and non-diagnostic in vitro method for inhibiting the activity of transient receptor potential channel proteins, which comprises the steps of: contacting the transient receptor potential channel proteins or cells expressing the proteins with the compound as described in the third aspect of the present invention, or the pharmaceutically acceptable salt thereof, or the prodrug thereof, the compound as described in the fourth aspect of the present invention, or the pharmaceutically acceptable salt thereof, or the prodrug thereof, the compound as described in the fifth aspect of the present invention, or the pharmaceutically acceptable salt thereof, or the prodrug thereof, the compound as described in the sixth aspect of the present invention, or the pharmaceutically acceptable salt thereof, or the prodrug thereof, or the crystal form A of the hydrochloride of the compound of Formula I-1 as described in the eighteenth aspect of the present invention, thereby inhibiting the activity of the transient receptor potential channel protein.

In the twenty-third aspect of the present invention, it provides a method for inhibiting transient receptor potential channel protein or preventing and/or treating diseases related to transient receptor potential channel protein (TRP), administering the compound as described in the third aspect of the present invention, or the pharmaceutically acceptable salt thereof, or the prodrug thereof, the compound as described in the fourth aspect of the present invention, or the pharmaceutically acceptable salt thereof, or the prodrug thereof, the compound as described in the fifth aspect of the present invention, or the pharmaceutically acceptable salt thereof, or the prodrug thereof, the compound as described in the sixth aspect of the present invention, or the pharmaceutically acceptable salt thereof, or the prodrug thereof, or the crystal form A of the hydrochloride of the compound of Formula I-1 as described in the eighteenth aspect of the present invention to a subject in need thereof.

It should be understood that within the scope of the present invention, the above-described technical features of the present invention and the technical features described in detail below (e.g., embodiments) may be combined with each other to constitute a new or preferred technical solution. Limited by space, it will not be repeated here.

DETAILED DESCRIPTION OF THE INVENTION

Figure 1:
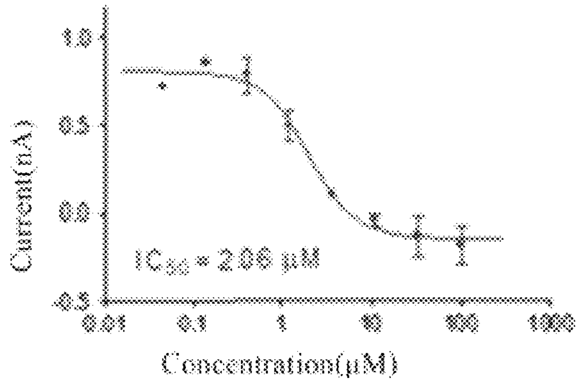
FIG. 1 shows the TRPA1 inhibitory activity $IC_{50}$ of compound I-1 tested by automatic patch clamp.

Through extensive and in-depth research, the present inventors have unexpectedly developed, for the first time, a compound, or a pharmaceutically acceptable salt thereof, or a prodrug thereof, the compound has a structure of Formula I, Formula Z, Formula G, Formula A or Formula B. Experiments have shown that the compounds of the present invention have a significant inhibitory effect on TRP channels. The compound of the present invention can effectively treat pain related to TRP (especially TRPA1) targets. In addition, the present invention also provided a crystal form A of the hydrochloride of the compound of Formula I-1 in solid form, the crystal form A of the hydrochloride of the compound of Formula I-1 is convenient for storage, transportation, and has strong druggability and strong stability (especially with excellent thermal stability and high humidity stability). The present invention has been completed on this basis.

Terms

As used herein, the terms “include,” “comprise” and “contain” are used interchangeably to include not only closed definitions, but also semi-closed, and open definitions. In other words, the term includes “consist of” and “substantially consist of”.

As use herein, “$R_1$”, “$R^1$” and “R1” have the same meaning and can be replaced with each other, and other similar definitions have the same meaning.

As use herein, the term “$C_1$-$C_6$ alkyl”, “$C_1$-$C_3$ alkyl” or “$C_1$-$C_4$ alkyl” refers to a linear or branched alkyl with 1 to 6, 1 to 3 or 1 to 4 carbon atoms, such as methyl, ethyl, propyl, isopropyl, butyl, isobutyl, sec-butyl, tert-butyl, or the like.

As use herein, the term “$C_1$-$C_6$ alkoxy” refers to a linear or branched alkoxy with 1-6 carbon atoms, such as methoxy, ethoxy, propoxy, isopropoxy, butoxy, isobutoxy, sec-butoxy, tert-butoxy, pentyloxy, hexyloxy, or the like.

As use herein, the term “$C_6$-$C_{12}$ benzo aliphatic ring” refers to a group with 6-12 carbon atoms, including indanyl, tetrahydronaphthyl or dihydronaphthyl and the like.

As use herein, the term “$C_1$-$C_6$ haloalkoxy” refers to a linear or branched alkoxy with 1-6 carbon atoms in which one or more hydrogen atoms are substituted by a halogen, such as chloromethoxy, chloroethoxy, or the like.

As use herein, the term “$C_3$-$C_7$ cycloalkyl”, “$C_3$-$C_6$ cycloalkyl” refers to a cycloalkyl (including monocyclic, dicyclic or polycyclic) with 3-7 or 3-6 carbon atoms, such as cyclopropyl, cyclobutyl, methylcyclobutyl, cyclopentyl, cycloheptyl, or the like.

As use herein, the term “$C_2$-$C_4$ ester” refers to a group having structure of $C_1$-$C_3$ alkyl-OC(O)— or —OC(O)—$C_1$-$C_5$ alkyl, in which the alkyl can be linear or branched, such as $CH_3COO$—, $C_2H_5COO$—, $C_3H_8COO$—, $(CH_3)$ $2CHCOO$—, —$COOCH_3$, —$COOC_2H_5$, —$COOC_3H_8$, or the like.

As use herein, the term “$C_2$-$C_4$ amide” refers to a group having structure of $C_1$-$C_3$alkyl-CO—NH— or —NH—CO—$C_1$-$C_3$ alkyl, in which the alkyl can be linear or branched, such as $CH_3$—CO—NH—, $C_2H_5$—CO—NH—, —$COOCH_3$, —CO—NH—$C_2H_5$, —CO—NH—$C_3$—$H_8$, or the like.

As use herein, the term “$C_2$-$C_4$ acyl” refers to a group having structure of $C_1$-$C_3$alkyl-CO—, in which the alkyl can be linear or branched, such as $CH_3$—CO—, $C_2H_5$—CO—, $C_3H_8$—CO—, or the like.

As use herein, the term “$C_3$-$C_7$ heterocycloalkyl” refers to a monocyclic or polycyclic heterocycles (preferably monocyclic heterocycles) having 3-7 ring carbon atoms and 1-3 heteroatoms (preferably contains 1 nitrogen atom, that is, the nitrogen atom adjacent to $R^1$ and $R^2$), such as piperidinyl, tetrahydropyrrolyl, or the like.

As used herein, the term “5-7-membered carbocyclic” refers to any stable 5, 6, or 7-membered monocyclic, bicyclic, or polycyclic ring, and the carbocyclic may be saturated, partially unsaturated, unsaturated, but cannot be aromatic. Examples of the carbocyclic rings include, but are not limited to, cyclopropyl rings, cyclobutyl rings, cyclobutene rings, cyclopentyl rings, cyclopentene rings, cyclohexyl rings, cyclohexene rings, cycloheptyl rings, cycloheptene rings, or the like.

As used herein, the term "5-7 membered heterocyclic" refers to any stable monocyclic, bicyclic or polycyclic ring containing one or more (preferably 1, 2 or 3) heteroatoms selected from N, O and S, and the number of ring atoms in the heterocyclic ring is 5-7, the heterocyclic ring can be a saturated, partially unsaturated, or unsaturated ring, but cannot be an aromatic ring. It should be understood that when there are multiple heteroatoms, the heteroatoms can be identical, partially identical, or completely different.

As used herein, the term "$C_1$-$C_3$ haloalkyl" refers to a linear or branched alkyl having 1 to 3 carbon atoms in which one or more hydrogen atoms are substituted by halogen groups, such as monochloromethyl, dichloroethyl, trichloropropyl, or the like.

As used herein, the term "$C_1$-$C_4$ carboxy" refers to a group having structure of $C_1$-$C_3$ alkyl-COOH, in which the alkyl can be linear or branched, such as $CH_3COOH$, $C_2H_5COOH$, $C_3H_8COOH$, $(CH_3)_2CHCOOH$, or the like.

As used herein, the term "$C_6$-$C_{12}$ aryl" refers to a monocyclic or bicyclic aromatic hydrocarbon group having 6 to 12 carbon atoms in the ring portion, such as phenyl, naphthyl, biphenyl, or the like.

As used herein, the term "5-7 membered heteroaromatic ring" refers to an aromatic heterocyclic ring system having one to more (preferably 1, 2, or 3) heteroatoms selected from N, O, and S, and having 5-7 ring atoms. It should be understood that when there are multiple heteroatoms, the heteroatoms can be identical, partially identical, or completely different. For example, examples of 5-membered heteroaromatic rings include (but are not limited to): pyrrole ring, furan ring, thiophene ring, imidazole ring, oxazole ring, thiazole ring, examples of 6-membered heteroaromatic ring include (but are not limited to) pyridine ring, pyrazine ring, pyridazine ring, pyrimidine ring, or the like.

As used herein, the term "five- or six-membered heteroaryl" refers to an aromatic group having one to more (preferably 1, 2, or 3) heteroatoms selected from N, O, and S, and having 5 or 6 ring atoms. It should be understood that when there are multiple heteroatoms, the heteroatoms can be identical, partially identical, or completely different. For example, examples of 5-membered heteroaryl include (but are not limited to): pyrrolyl, furyl, thienyl, imidazolyl, oxazolyl, thiazolyl, or the like.

As used herein, the term "six-membered aryl" refers to an aromatic group having 6 ring atoms, and the ring atoms are all carbon atoms, such as a phenyl, or the like.

As use herein, that term "halogen" refers to F, Cl, Br and I.

As used herein,

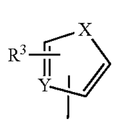

and

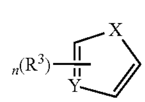

have the same meaning, and both represent a unsubstituted heteroaryl or a heteroaryl substituted with 1 to 5 (preferably 1 to 3) $R^3$ substituents.

As used herein, the term "substituted" means that the hydrogen atom on the group is substituted by a non-hydrogen atom group, but the valence requirements must be met and a chemically stable compound is generated by the substitution. In the specification, it should be construed that all substituents are unsubstituted, unless expressly described as "substituted" herein. In a preferred embodiment, any of the "substituted" means that 1-4 (preferably 1, 2, 3, or 4) hydrogen atoms on the group are each independently substituted by a substituent selected from the group consisting of: $C_1$-$C_6$ alkyl, $C_3$-$C_7$ cycloalkyl, $C_1$-$C_3$ haloalkyl, halogen, nitro, cyano, hydroxyl, $C_1$-$C_4$ carboxy, $C_2$-$C_4$ ester, $C_2$-$C_4$ amide, $C_1$-$C_6$ alkoxy, $C_1$-$C_6$ haloalkoxy, benzyl, six-membered aryl, five- or six-membered heteroaryl (preferably $C_5$ heteroaryl).

It should be understood that in the present invention, substituents can be connected to the parent group or substrate on any atom, unless the connection violates the valence requirement; the same or different substituents can be on the same atom or on different atoms.

Similarly, it should be understood that those ordinary skilled in the art can select the substituents and substitution on the compounds of the present invention to produce chemically stable compounds, which can be synthesized by techniques known in the art and method described below. If substituted by more than one substituent, it should be understood that the multiple groups may be on the same carbon or on different carbons, as long as a stable structure is produced.

In the present invention, the structures of R-duloxetine and S-duloxetine are as follows:

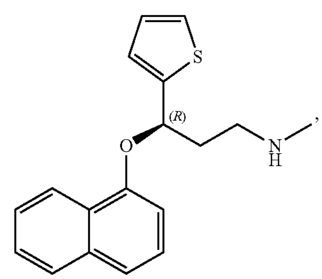

,

R-duloxetine

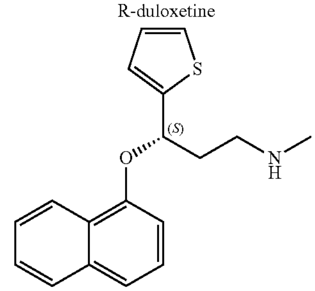

S-duloxetine

Active Ingredient

As used herein, the compound of formula I of the present invention refers to a compound having the structure of formula I, or a pharmaceutically acceptable salt thereof, or a prodrug thereof. It should be understood that the term also includes mixtures of the aforementioned components.

As used herein, the compound of formula Z of the present invention refers to a compound having the structure of formula Z, or a pharmaceutically acceptable salt thereof, or a prodrug thereof. It should be understood that the term also includes mixtures of the aforementioned components.

As used herein, the compound of formula G of the present invention refers to a compound having the structure of formula G, or a pharmaceutically acceptable salt thereof, or a prodrug thereof. It should be understood that the term also includes mixtures of the aforementioned components.

The compound of the present invention not only has an inhibitory effect on TRPA1, but also has a certain inhibitory effect on other members of the TRP family.

The term "pharmaceutically acceptable salt" refers to a salt formed by the compound of the present invention and an acid or a base suitable for use as a medicine. Pharmaceutically acceptable salts include inorganic salts and organic salts. A preferred type of salt is the salt formed by the compound of the present invention and an acid, acids suitable for salt formation include (but are not limited to): hydrochloric acid, hydrobromic acid, hydrofluoric acid, sulfuric acid, nitric acid, phosphoric acid and other inorganic acids, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid and other organic acids; and acidic amino acids such as aspartic acid and glutamic acid, etc. A preferred type of salt is a metal salt formed by the compound of the present invention and a base, suitable bases for salt formation include (but are not limited to): inorganic bases such as sodium hydroxide, potassium hydroxide, sodium carbonate, sodium bicarbonate, sodium phosphate, etc., organic bases such as ammonia, triethylamine, diethylamine, etc.

In the present invention, a preferred pharmaceutically acceptable salt of compound of formula Z, compound of formula I, compound of formula A or compound of formula B is a salt formed by compound of formula Z, compound of formula I, compound of formula A or compound of formula B and acids selected from the group consisting of: hydrochloric acid, mucic acid, D-glucuronic acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid, aspartic acid, glutamic acid, or combinations thereof.

Preferably, the pharmaceutically acceptable salt of compound of formula Z, compound of formula I, compound of formula A or compound of formula B is a salt formed by compound of formula Z, compound of formula I, compound of formula A or compound of formula B and acids selected from the group consisting of: hydrochloride, maleate, oxalate, mucate, fumarate, D-glucuronate, or combinations thereof.

Preferred compounds of the present invention include any one compound selected from Table 1 below:

TABLE 1

| Number | Name | Structural formula |
|---|---|---|
| Compound I-1 | (R)-3-(benzofuran-7-yloxy)-N-methyl-3-(thiophen-2-yl) propan-1-amine | 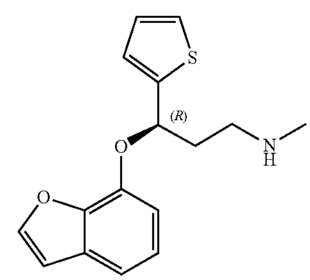 |
| Compound I-2 | (R)-3-(benzofuran-7-yloxy)-3-(thiophen-2-yl)propan-1-amine | 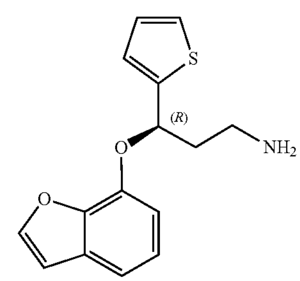 |
| Compound I-3 | (R)-3-(benzofuran-7-yloxy)-N,N-dimethyl-3-(thiophen-2-yl) propan-1-amine | 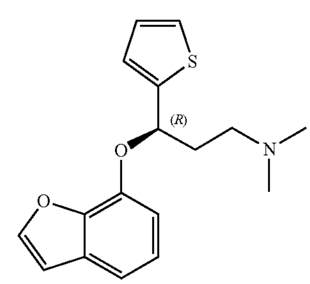 |

TABLE 1-continued

| Number | Name | Structural formula |
| --- | --- | --- |
| Compound I-4 | (R)-3-(benzofuran-7-yloxy)-N-ethyl-3-(thiophen-2-yl)propan-1-amine | 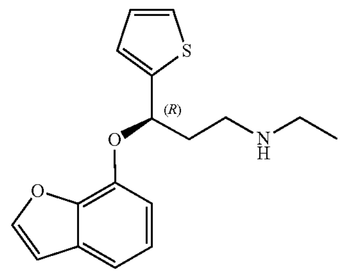 |
| Compound I-5 | (R)-3-(benzofuran-7-yloxy)-N-methyl-3-(thiophen-3-yl) propan-1-amine | 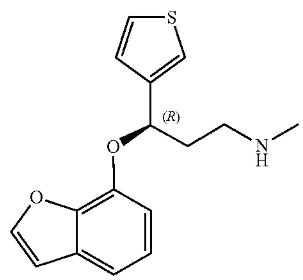 |
| Compound I-6 | (R)-3-(benzofuran-7-yloxy)-N-methyl-3-(5-methylthiophen-2-yl)propan-1-amine | 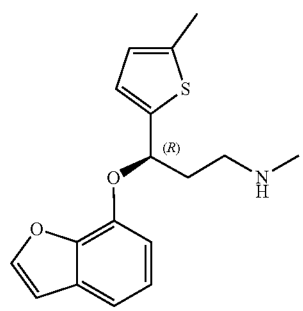 |
| Compound I-7 | (R)-3-(benzofuran-7-yloxy)-3-(5-chlorothiophen-2-yl)-N-methylpropan-1-amine | 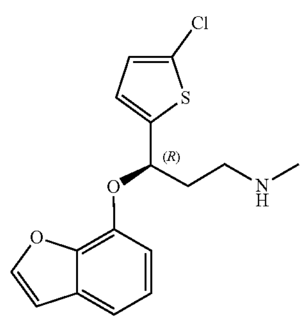 |
| Compound I-8 | (R)-3-(benzofuran-7-yloxy)-3-(furan-2-yl)-N-methylpropan-1-amine | 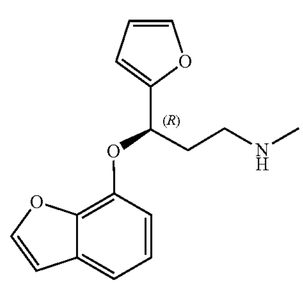 |

TABLE 1-continued

| Number | Name | Structural formula |
|---|---|---|
| Compound I-9 | (R)-3-((2,3-dihydro-1H-inden-4-yl)oxy)-N-methyl-3-(thiophen-2-yl)propan-1-amine | 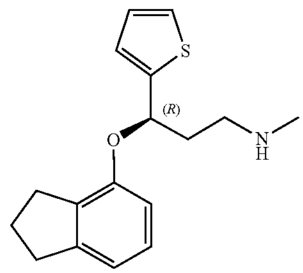 |
| Compound I-10 | (R)-N-methyl-3-((5,6,7,8-tetrahydronaphthalen-1-yl)oxy)-3-(thiophen-2-yl)propan-1-amine | 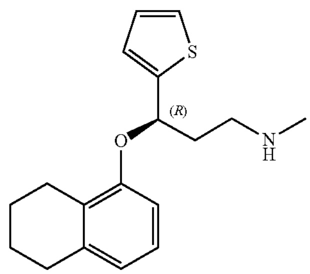 |
| Compound I-11 | (R)-3-(benzofuran-4-yloxy)-N-methyl-3-(thiophen-2-yl) propan-1-amine | 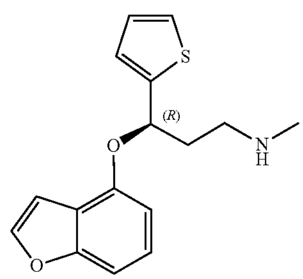 |

Preparation Method

The present invention also provided a preparation method of (R)-3-aryloxy-3-five-membered heteroaryl-propylamine compound represented by Formula I.

The present invention also provided a preparation method of intermediates II to III, which can be used for preparing the above-mentioned compounds.

The specific synthesis strategies are as follows:

Synthesis of the compound represented by formula I:

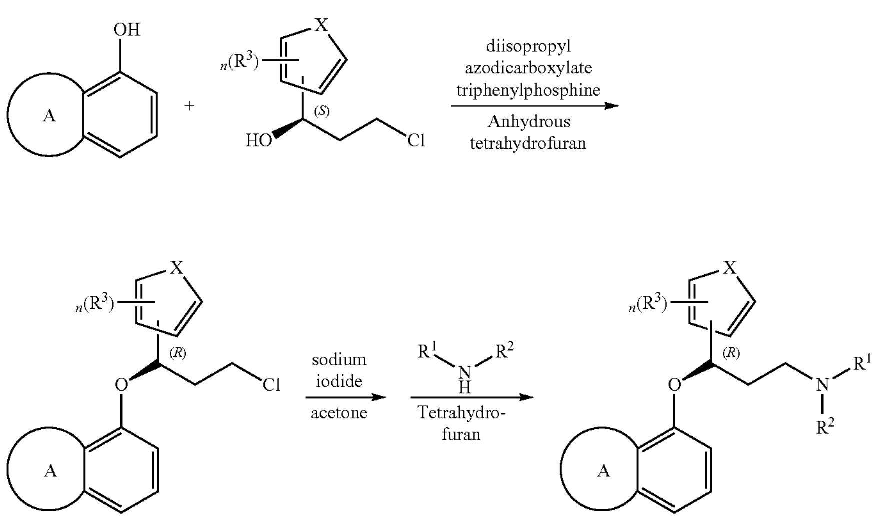

II I

-continued

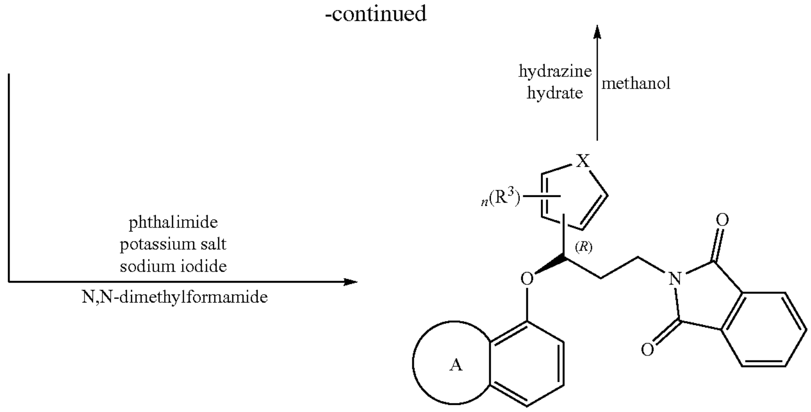

III wherein A, X, $R^1$, $R^2$, $R^3$ and n are as defined above.

1) dissolving a fused furan ring phenol or fused aliphatic ring phenol, (S)-1-($_n(R^3)$-five-membered heteroaryl)-3-chloro-propanol and triphenylphosphine into anhydrous tetrahydrofuran, slowly adding diisopropyl azodicarboxylate dropwise to the system under ice bath conditions, after the dropwise addition, transferring the system to 20-25° C. for overnight reaction. After completion of the reaction, spin-drying the system directly, and separating and purifying the residue by column chromatography to obtain the intermediate II.
2) dissolving the intermediate II into a saturated sodium iodide in acetone, and reacting overnight at a temperature of 50-70° C. After completion of the reaction, spin-drying the solvent, adding water into the system, extracting three times with ethyl acetate, washing with saturated brine, drying with anhydrous sodium sulfate, filtering, and concentrating; then dissolving the residue in tetrahydrofuran, and adding an aqueous solution or alcohol solution of amine, and reacting overnight at 20-25° C. After completion of the reaction, spin-drying the solvent, and adding a sodium hydroxide aqueous solution to the system, extracting with ethyl acetate for three times, washing with saturated brine, drying with anhydrous sodium sulfate, filtering, and concentrating, then separating the residue by column chromatography to obtain the compound I.
3) dissolving the intermediate II, phthalimide potassium salt and sodium iodide in N,N-dimethylformamide solution, and reacting overnight at 70-90° C. After completion of the reaction, adding water to the system, extracting with ethyl acetate for three times, washing with water, washing with saturated brine, drying with anhydrous sodium sulfate, filtering, and concentrating, then separating the residue by column chromatography to obtain the Intermediate III.
4) dissolving the Intermediate III in a methanol solution, adding hydrazine hydrate, and reacting overnight at 20-25° C. After completion of the reaction, spin-drying the solvent, and separating the residue by column chromatography to obtain the compound I.

Synthesis of Salts of Compound

The compounds as shown in Formula I, Formula Z, Formula G, Formula A or Formula B of the present invention can be converted into pharmaceutically acceptable salts by conventional methods, for example, the corresponding acid solution can be added into the solution of the above compounds, and the corresponding salts of the compounds of the present invention can be obtained by removing the solvent under reduced pressure after the salt formation is complete.

Transient Receptor Potential Channel Protein (TRP)

Transient receptor potential channel proteins are a protein superfamily consisted of important cation channels existing on the cell membrane. Transient receptor potential channel proteins include several subgroups, such as TRPA, TRPC, TRPM, TRPV, TRPML and TRPP subgroups.

TRPA1 is a member of TRPA subfamily, TRPA1 is also called as transient receptor potential anchor protein 1. Studies have found that TRPA1 channel protein is related to diseases such as pain, epilepsy, inflammation, respiratory disorders, pruritus, urinary tract disorders, inflammatory bowel disease and other diseases. TRPA1 is the target for treating pain, epilepsy, inflammation, respiratory disorders, pruritus, urinary tract disorders, inflammatory bowel disease and other diseases.

Typically, the disease related to transient receptor potential channel protein (TRP) is pain. The compound of Formula I, Formula Z, Formula G or the crystal form A of the hydrochloride of the compound of Formula I has an effective therapeutic effect on pain.

Typically, the pain includes (but is not limited to): acute pain, inflammatory pain, visceral pain, neurogenic pain, fibromyalgia, headache, nerve pain, mixed pain, cancer-induced pain, inflammation pain, and combinations thereof.

Typically, the acute pain is injury pain or postoperative pain.

As used herein, the terms "postoperative pain" and "post-surgical pain" are used interchangeably.

Typically, the postoperative pain is postoperative pain following a surgical procedure.

Typically, the postoperative pain is post-operative wound pain.

Typically, the post-operative wound pain is selected from the group consisting of post-operative skin wound pain, post-operative muscle wound pain, and combinations thereof.

Typically, the post-operative wound pain is skin and muscle post-operative wound pain.

Typically, the inflammatory pain is chronic inflammatory pain.

Typically, the inflammatory pain is osteoarthritic pain or rheumatoid arthritic pain.

Typically, the headache is migraine or muscle tension pain.

Typically, the neuralgia is trigeminal neuralgia, diabetic pain, sciatica, or postherpetic neuralgia.

In another preferred embodiment, the acute pain is injury pain or postoperative pain.

Use

The invention also provided a method of inhibiting transient receptor potential channel protein (TPR) and a method of treating diseases related to TPR.

The compound of Formula I, Formula Z, Formula G or the crystal form A of the hydrochloride of the compound of Formula I of the present invention can be used to inhibit the transient receptor potential channel protein, thereby preventing or treating diseases related to the transient receptor potential channel protein.

The invention provided a use of the compound of Formula Z, or the pharmaceutically acceptable salt thereof, or the prodrug thereof, the compound of Formula I, or the pharmaceutically acceptable salt thereof, or the prodrug thereof, the compound of Formula G, or the pharmaceutically acceptable salt thereof, or the prodrug thereof, or the crystal form A of the hydrochloride of the compound of Formula I-1 for (a) preparating a transient receptor potential channel protein (TRPA1) inhibitors; (b) manufacturing a medicament for the prevention and/or treatment of diseases associated with transient receptor potential channel protein (TRPA1).

In the present invention, the transient receptor potential channel protein (TPR) is TPR1.

In the present invention, examples of diseases related to transient receptor potential channel proteins include (but are not limited to): pain, epilepsy, inflammation, respiratory disorders, pruritus, urinary tract disorders, inflammatory bowel disease, or combinations thereof. Typically, the pain includes (but is not limited to): acute inflammatory pain, inflammatory pain (such as chronic inflammatory pain, osteoarthritis pain or rheumatoid arthritis pain), visceral pain, neurogenic pain, fibromyalgia, headache (such as migraine, muscular tension pain, etc.), nerve pain (such as trigeminal neuralgia, diabetic pain, postherpetic neuralgia, etc.), or cancer-induced pain.

In a preferred embodiment, the present invention provided a non-therapeutic and non-diagnostic in vitro method for inhibiting transient receptor potential channel protein activity, includes, for example, in a culture system in vitro, contacting a transient receptor potential channel protein or a cell expressing the protein with the compound of Formula I, Formula Z or Formula G, or the pharmaceutically acceptable salt thereof, or the prodrug thereof, or the crystal form A of the hydrochloride of the compound of Formula I-1 according to the present invention, thereby inhibiting the activity of the transient receptor potential channel protein.

In the present invention, the non-therapeutic and non-diagnostic in vitro method for inhibiting the activity of transient receptor potential channel proteins can be used for drug screening, quality control and other purposes. For example, in a culture system in vitro, by contacting the compound of formula I, formula Z, or formula G, or the pharmaceutically acceptable salt thereof, or the prodrug thereof, or the crystal form A of the hydrochloride of the compound of Formula I-1 of the present invention with transient receptor potential channel protein or cells expressing the protein, and the compounds that can inhibit transient receptor potential channel protein are selected as candidate drugs. Then, the therapeutic effect of the candidate compounds can be further studied through animal experiments and clinical trials on transient receptor potential channel protein and the related diseases.

The invention also provided a method for inhibiting transient receptor potential channel proteins, which may be therapeutic or non-therapeutic. Generally, the method comprises the steps of: administering the compound of formula I, formula Z, formula G, formula A, or formula B, or the pharmaceutically acceptable salt thereof, or the prodrug thereof, or the crystal form A of the hydrochloride of the compound of Formula I-1 of the present invention to a subject in need thereof.

Preferably, the subject includes humans and non-human mammals (rodents, rabbits, monkeys, domestic animals, dogs, cats, etc.).

Crystal Form

The present invention also provided a crystal form A of the hydrochloride of the compound of Formula I-1,

I-1

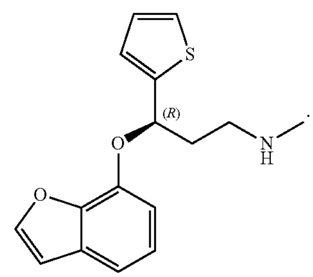

The crystal form A of the hydrochloride of the compound of Formula I-1 of the present invention is in solid form. Compared with the oily substance of the free compound of formula I-1, the solid form of the salt crystal form of the compound of formula I-1 is convenient for storage, transportation and has a strong druggability. The crystal form A of the hydrochloride of the compound of Formula I-1 as described herein also has excellent stability, especially excellent thermal stability and high humidity stability.

As used herein, the terms "crystal form A of the hydrochloride of the compound of Formula I-1", "crystal form A of the hydrochloride" and "crystal form A" can be used interchangeably.

The crystal form A of the hydrochloride of the compound of Formula I-1 as described herein has characteristic peaks at one or more 2θ values selected from the group consisting of 10.003±0.2°, 11.171±0.2°, 15.987±0.2°, 16.734±0.2°, 17.092±0.2°, 18.173±0.2°, 18.849±0.2°, 20.681±0.2°, 21.156±0.2°, 21.649±0.2°, 22.084±0.2°, 22.794±0.2°, 23.761±0.2°, 25.298±0.2°, 25.967±0.2°, 26.640±0.2°, 27.273±0.2°, 28.099±0.2°, 28.615±0.2°, 28.813±0.2°, 29.501±0.2°, 30.118±0.2°, 30.513±0.2°, 32.522±0.2°, 33.274±0.2°, 34.081±0.2°, 35.815±0.2°, 37.553±0.2°, 40.018±0.2°, 42.927±0.2°, 44.129±0.2.

Figure 7:
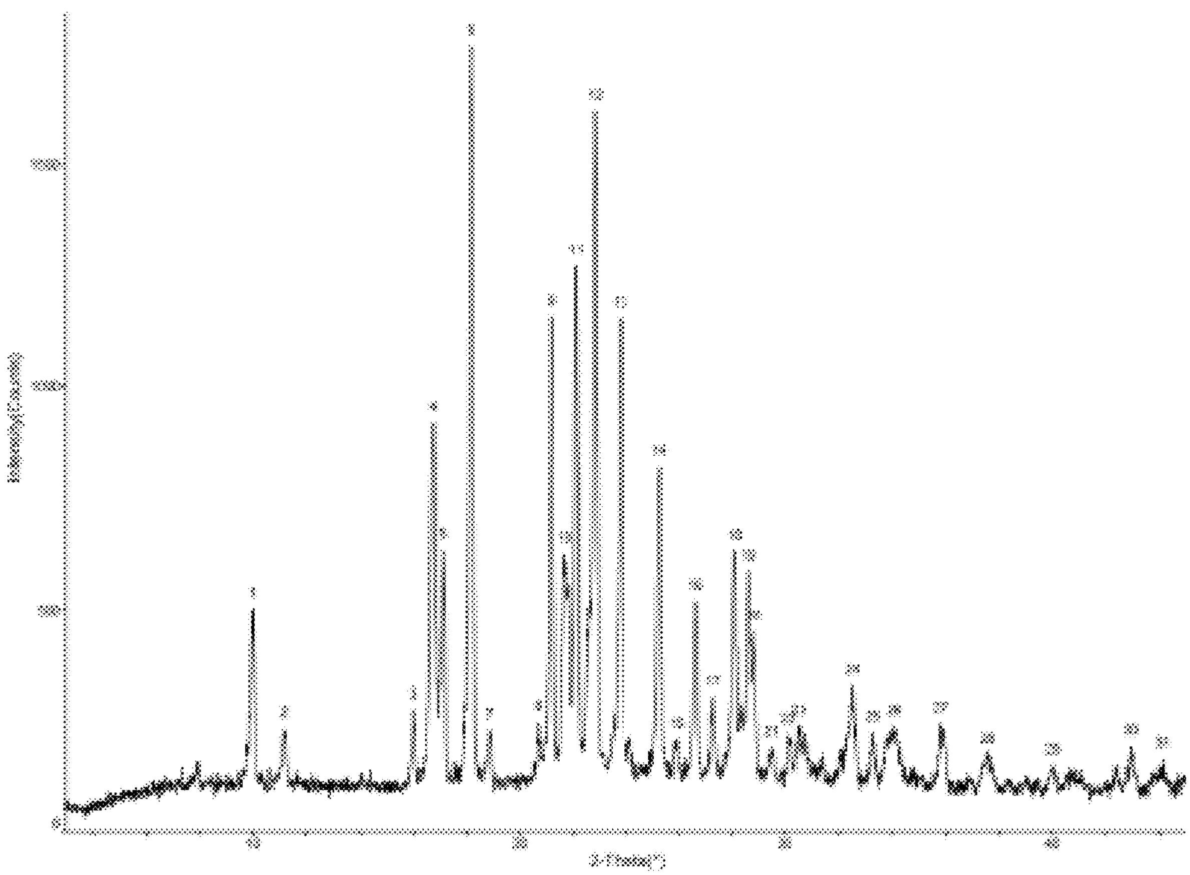
FIG. 7 is an X-ray powder diffraction pattern of the crystal form A of the hydrochloride of the compound I-1.

Typically, the crystal form A of the hydrochloride of the compound of Formula I-1 has X-ray powder diffraction characteristic peaks substantially as shown in FIG. 7.

In another preferred embodiment, the differential scanning calorimetry (DSC) pattern of the crystal form A of the hydrochloride of the compound of Formula I-1 begins to appear endothermic peaks upon being heated to 142.30° C. (preferably ±4° C., ±3° C., ±2° C. or ±1° C.).

Figure 8:
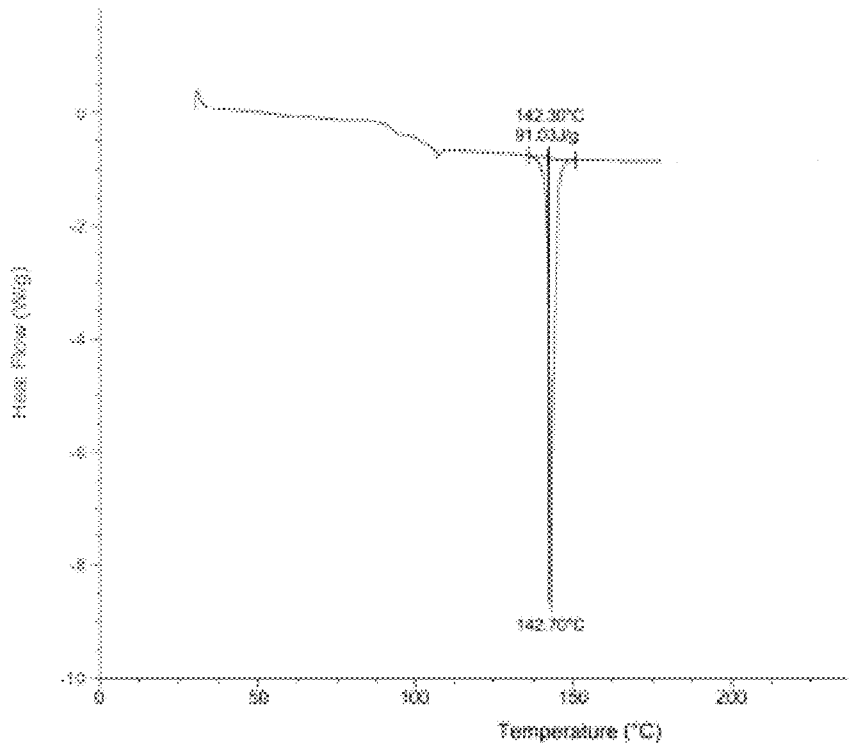
FIG. 8 is a differential scanning calorimetry (DSC) pattern of the crystal form A of the hydrochloride of the compound I-1.

Typically, the differential scanning calorimetry (DSC) pattern of the crystal form A of the hydrochloride of the compound of Formula I-1 is substantially as shown in FIG. 8.

In another preferred embodiment, the thermogravimetric analysis (TGA) pattern of the crystal form A of the hydrochloride of the compound of Formula I-1 has a weight loss of about 0.9827% (preferably ±0.1%, ±0.2%, ±0.3%, ±0.4%, or ±0.5%) upon being heated to 168.01° C.

Figure 9:
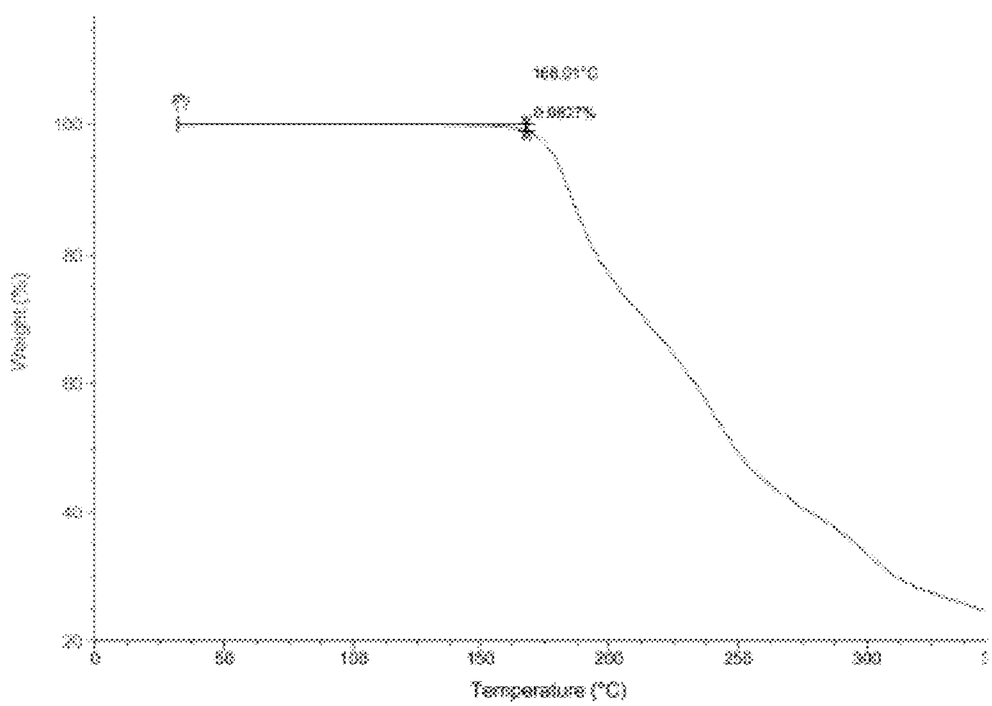
FIG. 9 is a thermogravimetric analysis (TGA) pattern of the crystal form A of the hydrochloride of the compound I-1.

Typically, the thermogravimetric analysis (TGA) pattern of the crystal form A of the hydrochloride of the compound of Formula I-1 is substantially as shown in FIG. 9.

Preferably, a method for preparing the crystal form A of the hydrochloride of the compound of Formula I-1 as described in the invention, comprising the steps of:

(a) after mixing the compound of formula I-1 with ethyl acetate, adding hydrochloric acid dropwise at 5~15° C. to adjust the pH of the system to 6-8, reacting and precipitating a solid, and filtering to obtain the crystal form A of the hydrochloride of the compound of Formula I-1.

In another preferred embodiment, in the step (a), the reaction time is 3-8 min, preferably 5 min.

In another preferred embodiment, in the step (a), the weight-volume ratio (kg:L) of the compound of Formula I-1 to the organic solvent is 0.2-2: 2-30, preferably 0.4-1.0:5-18, more preferably 0.5-0.9:8-15.

The crystal form A of the hydrochloride of the compound of Formula I-1 of the present invention can inhibit TRPA1.

Compositions and Methods of Administration

The invention provided a composition for inhibiting the activity of transient receptor potential channel proteins. The compositions include, but are not limited to, pharmaceutical compositions, food compositions, dietary supplements, beverage compositions, etc.

Typically, the composition is a pharmaceutical composition comprising the compound of Formula I, Formula Z, Formula G, Formula A or Formula B, or the crystal form A of the hydrochloride of the compound of Formula I-1 as described in the present invention; and pharmaceutically acceptable carriers.

In the present invention, the dosage forms of pharmaceutical compositions include (but are not limited to) oral preparations, injections and topical preparations.

Typically, the dosage forms comprise (but are not limited to): tablets, capsules, injections, infusions, ointments, gels, solutions, microspheres and films.

The term "pharmaceutically acceptable carrier" means one or more compatible fillers in solid, semi-solid, liquid or gel form, which is suitable for human or animal use and has sufficient purity and low enough toxicity. The "compatible" means the components and the active ingredient of a pharmaceutical composition can be blended with each other without significantly reducing the efficacy.

It should be understood that in the present invention the carrier is not particularly limited, and materials commonly used in the field can be selected, or it can be manufactured by conventional methods, or it is commercially available. Examples of pharmaceutically acceptable carriers include cellulose and its derivatives (such as methyl cellulose, ethyl cellulose, hydroxypropyl methyl cellulose, sodium carboxymethyl cellulose, etc.), gelatin, talc, and solid lubricants (such as stearic acid, magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween), wetting agents (such as sodium lauryl sulfate), buffering agents, chelating agents, thickening agents, pH adjusters, penetration enhancers, coloring agents, flavoring agents, stabilizers, antioxidants, preservatives, bacteriostatic agent, pyrogen-free water, etc.

Typically, in addition to the active pharmaceutical ingredients, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures thereof. In addition to these inert diluents, the composition may also contain auxiliaries such as wetting agents, emulsifiers, suspending agents, and the like.

Pharmaceutical preparations should match the mode of administration. The medicament of the present invention may also be used with other synergistic therapeutic agents (including before, during or after use). When a pharmaceutical composition or preparation is used, a safe and effective amount of the drug is administered to a subject in need (such as a human or non-human mammal). The specific dose should consider the route of administration, patient's health and other factors, which are within the skill range of skilled doctors.

The main advantages of the present invention include:

(a) The present invention provided a class of compounds of Formula I, Formula Z, Formula G, Formula A or Formula B with novel structures and excellent TRP channel (in particular TRPA1) inhibitory activity.

(b) The compounds of the present invention exhibit potent analgesic effects in variety of animal models.

(c) The compounds of the present invention have less toxicity and higher activity, and therefore have a larger safety window.

(d) The compounds of the present invention have good druggability.

(e) The compounds of the present invention have excellent pharmacokinetic properties.

(f) The compounds of the present invention are suitable for oral administration.

(g) The invention also provided a crystal form A of the hydrochloride of the compound of Formula I-1, which is in solid form, and the salt crystal form of the compound of Formula I-1 in solid form is convenient for storage, transportation, and has good druggability and stability (especially excellent thermal stability and high humidity stability) compared to the oil form of the free compound of Formula I-1.

The present invention will be further explained below in conjunction with specific embodiments. It should be understood that these embodiments are only used to illustrate the present invention and not to limit the scope of the present invention. In the following examples, the test methods without specific conditions are usually in accordance with conventional conditions or the conditions recommended by the manufacturer. Unless otherwise specified, percentages and parts are percentages by weight and parts by weight.

Example 1

(R)-7-(3-chloro-1-(thiophen-2-yl)propoxy)benzofuran (Intermediate II-1)

II-1

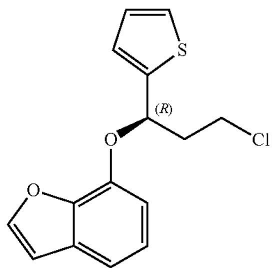

528 mg of (S)-3-chloro-1-(thiophen-2-yl)propan-1-ol, 400 mg of 7-hydroxybenzofuran and 862 mg of triphenylphosphine were dissolved in 30 ml of anhydrous tetrahydrofuran, and 667 mg of diisopropyl azodicarboxylate was added dropwise slowly to the system under ice bath, after the addition, then the reaction system was transferred to room temperature to react overnight. After completion of the reaction, the system was spin-dried directly, and the residue was separated and purified by column chromatography to obtain 685 mg Intermediate II-1 as a colorless oil, yield 78.46%.

$^1$H NMR (500 MHz, $CDCl_3$) δ 7.62 (t, J=3.2 Hz, 1H), 7.41 (dd, J=1.8, 0.6 Hz, 1H), 7.24 (dt, J=8.1, 1.8 Hz, 1H), 7.15-7.11 (m, 1H), 6.91 (d, J=7.7 Hz, 1H), 6.77 (dd, J=8.0, 2.2 Hz, 1H), 6.35 (d, J=3.3 Hz, 1H), 6.33 (dd, J=3.3, 1.9 Hz, 1H), 5.75 (dd, J=8.4, 5.1 Hz, 1H), 3.93 (dd, J=11.1, 8.2, 5.4 Hz, 1H), 3.77-3.70 (m, 1H), 2.85-2.74 (m, 1H), 2.54-2.48 (m, 1H). MS (ESI, m/z): 292.93 $(M+H)^+$.

Example 2

(R)-3-(benzofuran-7-yloxy)-N-methyl-3-(thiophen-2-yl)propan-1-amine (Compound I-1)

I-1

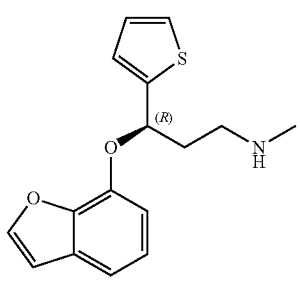

685 mg of Intermediate II-1 was dissolved in a saturated sodium iodide solution in acetone and refluxed overnight. After completion of the reaction, the solvent was spin-dried. Then water was added into the reaction system, extracted with ethyl acetate for three times, washed with saturated salt water, dried over anhydrous sodium sulfate, filtered, and concentrated. The residue was dissolved in 30 mL tetrahydrofuran, 3 mL 40% methylamine aqueous solution was added to react overnight. After completion of the reaction, the solvent was spin-dried, sodium hydroxide solution was added into the system, extracted with ethyl acetate for three times, washed with saturated salt water, dried over anhydrous sodium sulfate, filtered and concentrated. The residue was separated by column chromatography (methanol/dichloromethane=1:15) to obtain 336 mg Compound I-1 as a colorless oil, yield 49.97%.

1H NMR (500 MHz, DMSO) δ 7.97 (d, J=2.1 Hz, 1H), 7.49 (dd, J=5.0, 1.1 Hz, 1H), 7.25-7.18 (m, 2H), 7.08 (t, J=7.9 Hz, 1H), 6.99 (dd, J=5.0, 3.5 Hz, 1H), 6.96 (d, J=7.9 Hz, 1H), 6.94 (d, J=2.1 Hz, 1H), 6.05 (dd, J=7.9, 5.2 Hz, 1H), 3.15-2.96 (m, 2H), 2.57 (s, 3H), 2.49-2.43 (m, 1H), 2.33-2.25 (m, 1H). MS (ESI, m/z): 288.0 (M+H)+.

Example 3

(R)-2-(3-(benzofuran-7-yloxy)-3-(thiophen-2-yl)propyl)isoindoline-1,3-dione (Intermediate III)

III

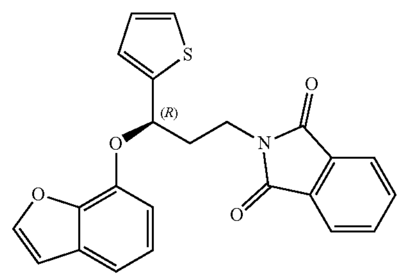

425 mg of intermediate II-1, 807 mg of phthalimide potassium salt and 100 mg of sodium iodide were dissolved in 15 ml of N,N-dimethylformamide, and reacted at 90° C. under nitrogen overnight. After completion of the reaction, water was added to the system, extracted with ethyl acetate for three times, washed with water, washed with saturated brine, dried over anhydrous sodium sulfate, filtered, and concentrated. The residue was separated by column chromatography (ethyl acetate/petroleum ether=1:5) to obtain Intermediate III, 412 mg of yellow solid, with a yield of 70.35%.

$^1$H NMR (500 MHz, $CDCl_3$) δ7.84-7.80 (m, 2H), 7.70 (dd, J=5.4, 3.1 Hz, 2H), 7.50 (d, J=2.0 Hz, 1H), 7.21 (dd, J=5.1, 1.4 Hz, 1H), 7.18 (dd, J=7.9, 0.9 Hz, 1H), 7.09 (d, J=3.1 Hz, 1H), 7.08-7.03 (m, 1H), 6.91 (dd, J=10.1, 5.1 Hz, 1H), 6.82 (d, J=7.3 Hz, 1H), 6.71 (d, J=2.2 Hz, 1H), 5.85 (dd, J=7.7, 5.4 Hz, 1H), 4.11-3.92 (m, 2H), 2.68 (dd, J=14.4, 7.3 Hz, 1H), 2.53-2.39 (m, 1H). MS (ESI, m/z): 403.99 $(M+H)^+$.

Example 4

(R)-3-(benzofuran-7-yloxy)-3-(thiophen-2-yl)propan-1-amine (Compound I-2)

I-2

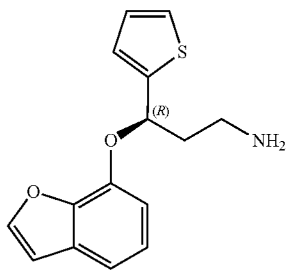

412 mg of Intermediate III and 270 mg of hydrazine hydrate were dissolved in 15 ml of methanol solution and reacted at room temperature overnight. After completion of the reaction, the solvent was spin-dried, and the residue was separated by column chromatography (methanol/dichloromethane=1:15) to obtain Compound 1-2, 124 mg of colorless oil, with a yield of 44.42%. 1H NMR (500 MHz, DMSO) δ 7.87 (d, J=2.3 Hz, 1H), 7.40 (dd, J=5.5, 1.6 Hz, 1H), 7.19-7.15 (m, 2H), 7.07 (t, J=7.9 Hz, 1H), 6.94 (dd, J=5.5, 3.8 Hz, 1H), 6.91 (d, J=7.7 Hz, 1H), 6.87 (d, J=2.4 Hz, 1H), 6.04 (m, 1H), 2.94-2.80 (m, 2H), 2.37-2.30 (m, 1H), 2.18 (dtd, J=11.8, 9.8, 5.1 Hz, 1H). MS (ESI, m/z): 273.98 $(M+H)^+$.

Example 5

(R)-3-(benzofuran-7-yloxy)-N,N-dimethyl-3-(thiophen-2-yl)propan-1-amine (Compound 1-3)

I-3

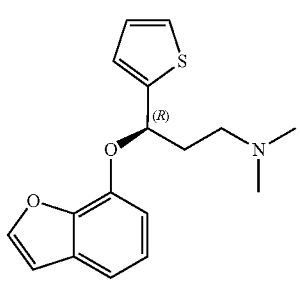

Except that the methylamine aqueous solution was replaced with dimethylamine, the other required raw materials, reagents and preparation methods were the same as those in Example 2, and 327 mg of colorless oily compound I-3 was obtained, with a yield of 44.76%.

1H NMR (500 MHz, $CDCl_3$) δ 7.74 (d, J=2.5 Hz, 1H), 7.31 (dt, J=12.8, 6.4 Hz, 1H), 7.19 (dd, J=7.8, 0.9 Hz, 1H), 7.05-7.01 (m, 2H), 6.91 (dd, J=5.0, 3.5 Hz, 1H), 6.83 (dd, J=6.8, 6.1 Hz, 1H), 6.73 (d, J=4.2 Hz, 1H), 5.85-5.77 (m, 1H), 2.53-2.48 (m, 2H), 2.48-2.40 (m, 1H), 2.26 (s, 6H), 2.16 (dt, J=10.1, 4.9 Hz, 1H).MS (ESI, m/z): 302.01 $(M+H)^+$.

Example 6

(R)-3-(benzofuran-7-yloxy)-N-ethyl-3-(thiophen-2-yl)propan-1-amine (Compound 1-4)

I-4

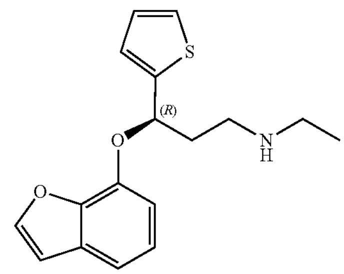

Except that the methylamine aqueous solution was replaced with ethylamine, the other required raw materials, reagents and preparation methods were the same as those in Example 2, and 478 mg of colorless oily compound I-4 was obtained, with a yield of 45.90%. 1H NMR (500 MHz, $CDCl_3$) δ 7.67 (d, J=2.4 Hz, 1H), 7.25 (t, J=7.6 Hz, 2H), 7.15-6.89 (m, 2H), 6.85 (dd, J=5.5, 3.9 Hz, 1H), 6.74 (d, J=8.4 Hz, 1H), 6.66 (d, J=1.8 Hz, 1H), 5.81 (dd, J=9.2, 6.4 Hz, 1H), 3.25 (t, J=8.7 Hz, 2H), 3.15 (q, J=7.3 Hz, 2H), 2.78-2.66 (m, 1H), 2.60-2.49 (m, 1H), 1.51 (t, J=7.3 Hz, 3H). MS (ESI, m/z): 302.10 $(M+H)^+$.

Example 7

(R)-3-(benzofuran-7-yloxy)-N-methyl-3-(thiophen-3-yl)propan-1-amine (Compound I-5)

I-5

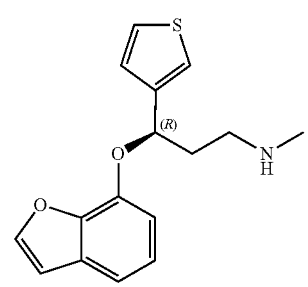

Except that the (S)-3-chloro-1-(thiophen-2-yl)propan-1-ol was replaced with (S)-3-chloro-1-(thiophen-3-yl)propan-1-ol, the other required raw materials, reagents and preparation methods were the same as those in Example 1-2, and 313 mg of compound I-5 was obtained as a colorless oil, with a yield of 32.71%.

1H NMR (500 MHz, $CDCl_3$) δ 7.63 (d, J=2.7 Hz, 1H), 7.31 (dd, J=5.5, 3.1 Hz, 1H), 7.27 (d, J=2.7 Hz, 1H), 7.20-7.14 (m, 2H), 7.07 (t, J=8.4 Hz, 1H), 6.76 (t, J=4.2 Hz, 1H), 6.73 (d, J=8.1 Hz, 1H), 5.66 (dd, J=7.7, 5.6 Hz, 1H), 2.95-2.83 (m, 2H), 2.50 (s, 3H), 2.44-2.33 (m, 1H), 2.26-2.14 (m, 1H). MS (ESI, m/z): 287.97 $(M+H)^+$.

Example 8

(R)-3-(benzofuran-7-yloxy)-N-methyl-3-(5-methylthiophen-2-yl)propan-1-amine (Compound I-6)

I-6

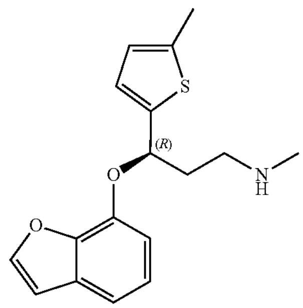

Except that the (S)-3-chloro-1-(thiophen-2-yl)propan-1-ol was replaced with (S)-3-chloro-1-(5-methylthiophen-2-yl)propan-1-ol, the other required raw materials, reagents and preparation methods were the same as those in Example 1-2, and 222 mg of compound I-6 was obtained as a colorless oil, with a yield of 26.42%.

1H NMR (500 MHz, $CDCl_3$) δ 7.61 (d, J=2.0 Hz, 1H), 7.16 (dt, J=10.7, 5.4 Hz, 1H), 7.09 (d, J=7.9 Hz, 1H), 6.87 (d, J=7.7 Hz, 1H), 6.81 (d, J=4.4 Hz, 1H), 6.77 (dd, J=7.0, 2.2 Hz, 1H), 6.60-6.53 (m, 1H), 5.74 (dd, J=7.7, 5.6 Hz, 1H), 2.94-2.80 (m, 2H), 2.55 (s, 3H), 2.46-2.37 (m, 4H), 2.26-2.17 (m, 1H). MS (ESI, m/z): 302.01 $(M+H)^+$.

Example 9

(R)-3-(benzofuran-7-yloxy)-3-(5-chlorothiophen-2-yl)-N-methylpropan-1-amine (Compound 1-7)

I-7

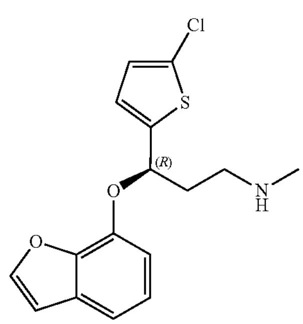

Except that the (S)-3-chloro-1-(thiophen-2-yl)propan-1-ol was replaced with (S)-3-chloro-1-(5-chlorothiophen-2-yl) propan-1-ol, the other required raw materials, reagents and preparation methods were the same as those in Example 1-2, and 275 mg of compound I-7 was obtained as a colorless oil, with a yield of 30.15%.

1H NMR (500 MHz, $CDCl_3$) δ 7.63 (d, J=2.1 Hz, 1H), 7.22 (d, J=8.1 Hz, 1H), 7.11 (d, J=7.7 Hz, 1H), 6.91 (dd, J=13.4, 6.4 Hz, 2H), 6.82 (d, J=4.2 Hz, 1H), 6.76 (d, J=4.3 Hz, 1H), 5.70 (dd, J=8.7, 6.0 Hz, 1H), 3.11-3.02 (m, 2H), 2.53 (s, 3H), 2.48 (dt, J=21.6, 7.2 Hz, 1H), 2.27 (ddd, J=13.7, 12.0, 6.7 Hz, 1H).MS (ESI, m/z): 321.96 $(M+H)^+$.

Example 10

(R)-3-(benzofuran-7-yloxy)-3-(furan-2-yl)-N-methylpropan-1-amine (Compound 1-8)

I-8

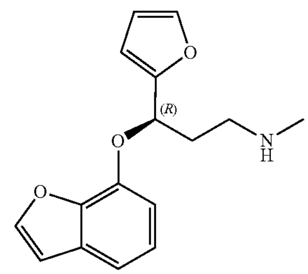

Except that the (S)-3-chloro-1-(thiophen-2-yl)propan-1-ol was replaced with (S)-3-chloro-1-(furan-2-yl)propan-1-ol, the other required raw materials, reagents and preparation methods were the same as those in Example 1-2, and 167 mg of compound I-8 was obtained as a colorless oil, with a yield of 15.55%.

1H NMR (500 MHz, $CDCl_3$) δ 7.56 (d, J=2.8 Hz, 1H), 7.33 (d, J=1.9 Hz, 1H), 7.17 (d, J=8.7 Hz, 1H), 7.01 (dd, J=11.5, 6.3 Hz, 1H), 6.74 (d, J=7.9 Hz, 1H), 6.67 (d, J=2.5 Hz, 1H), 6.26 (d, J=4.3 Hz, 1H), 6.15 (dd, J=4.2, 2.1 Hz, 1H), 5.56 (dd, J=8.4, 6.7 Hz, 1H), 3.11-2.96 (m, 2H), 2.64-2.55 (m, 4H), 2.40 (dd, J=12.4, 7.0 Hz, 1H). MS (ESI, m/z): 272.02 $(M+H)^+$.

Example 11

(R)-3-((2,3-dihydro-1H-inden-4-yl)oxy)-N-methyl-3-(thiophen-2-yl)propan-1-amine (Compound I-9)

I-9

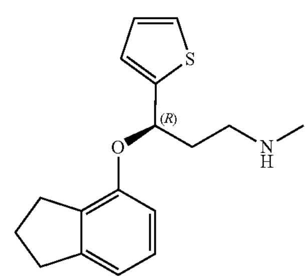

Except that 7-hydroxybenzofuran was replaced with 4-indanol, the other required raw materials, reagents and preparation methods were the same as those in Example 1-2, and 116 mg of compound I-9 was obtained as a colorless oil, with a yield of 20.75%. 1H NMR (500 MHz, CDCl3) δ 7.27 (dd, J=4.0, 2.1 Hz, 1H), 7.19-7.16 (m, 2H), 6.99 (t, J=8.4 Hz, 1H), 6.88 (d, J=7.7 Hz, 1H), 6.69 (d, J=8.5 Hz, 1H), 5.68 (dd, J=7.9, 4.8 Hz, 1H), 2.94 (dd, J=18.69, 9.1 Hz, 4H), 2.87 (ddd, J=10.0, 8.5 Hz, 4.0 Hz, 2H), 2.47 (s, 3H), 2.35-2.240 (m, 1H), 2.22-2.16 (m, 1H), 2.12-2.04 (m, 2H). MS (ESI, m/z): 288.03 $(M+H)^+$.

Example 12

(R)—N-methyl-3-((5,6,7,8-tetrahydronaphthalen-1-yl)oxy)-3-(thiophen-2-yl)propan-1-amine (Compound I-10)

I-10

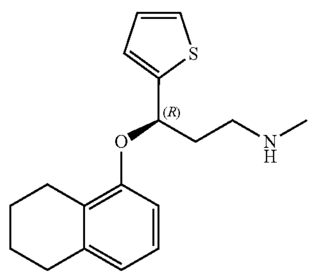

Except that the 7-hydroxybenzofuran was replaced with tetrahydronaphthol, the other required raw materials, reagents and preparation methods were the same as those in Example 1-2, and 103 mg of compound I-10 was obtained as a colorless oil, with a yield of 25.17%.

1H NMR (500 MHz, $CDCl_3$) δ 7.32 (d, J=2.2 Hz, 1H), 7.22-7.18 (m, 1H), 6.99-6.95 (m, 2H), 6.74 (d, J=8.5 Hz, 1H), 6.63 (d, J=8.8 Hz, 1H), 4.88 (dd, J=12.9, 4.4 Hz, 1H), 2.98-2.74 (m, 5H), 2.66-2.43 (m, 5H), 2.15-2.09 (m, 1H), 1.91-1.76 (m, 4H). MS (ESI, m/z): 302.0 $(M+H)^+$.

Example 13

(R)-3-(benzofuran-4-yloxy)-N-methyl-3-(thiophen-2-yl)propan-1-amine (Compound I-11)

I-11

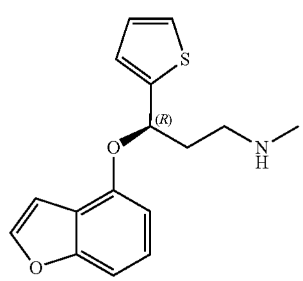

Except that the 7-hydroxybenzofuran was replaced with 4-hydroxybenzofuran, the other required raw materials, reagents and preparation methods were the same as those in Example 1-2, and 95 mg of compound I-11 was obtained as a colorless oil, with a yield of 14.06%.

1H NMR (500 MHz, $CDCl_3$) δ 7.49 (d, J=2.8 Hz, 1H), 7.16 (d, J=5.0, 1H), 7.11-7.04 (m, 3H), 6.89 (dd, J=5.2, 3.2 Hz, 2H), 6.74-6.65 (m, 1H), 5.81 (dd, J=7.5, 5.0 Hz, 1H), 3.16 (t, J=7.4 Hz, 2H), 2.76-2.67 (m, 1H), 2.65 (s, 3H), 2.62-2.51 (m, 1H). MS (ESI, m/z): 287.97 $(M+H)^+$.

Comparative Example 1

(S)-3-(benzofuran-7-yloxy)-N-methyl-3-(thiophen-2-yl)propan-1-amine (Compound C1)

C1

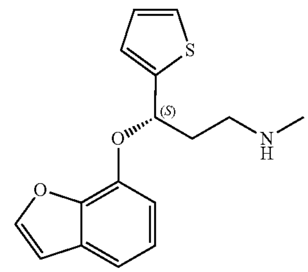

Except that the (S)-3-chloro-1-(thiophen-2-yl)propan-1-ol was replaced with (R)-3-chloro-1-(thiophen-2-yl)propan-1-ol, the other required raw materials, reagents and preparation methods were the same as those in Example 1-2, and 199 mg of compound C1 was obtained, with a yield of 39.96%.

$^1H$ NMR (400 MHz, $CDCl_3$) δ7.63 (d, J=2.0 Hz, 1H), 7.20 (t, J=6.6 Hz, 2H), 7.08-6.99 (m, 2H), 6.88 (dd, J=4.9, 3.6 Hz, 1H), 6.80 (d, J=7.9 Hz, 1H), 6.75 (d, J=2.0 Hz, 1H), 5.93 (dd, J=8.2, 4.4 Hz, 1H), 3.30 (t, J=7.0 Hz, 2H), 2.82-2.69 (m, 4H), 2.65-2.54 (m, 1H). MS (ESI, m/z): 287.87 $(M+H)^+$.

Comparative Example 2

(R)-3-(benzofuran-7-yloxy)-N-methyl-3-phenylpropan-1-amine (Compound C2)

C2

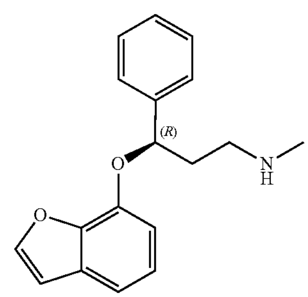

Except that the (S)-3-chloro-1-(thiophen-2-yl)propan-1-ol was replaced with (S)-3-chloro-1-phenylpropane-1-ol, the other required raw materials, reagents and preparation methods were the same as those in Example 1-2, and 147 mg of compound C2 was obtained, with a yield of 24.42%.

1H NMR (500 MHz, $CDCl_3$) δ 7.64 (d, J=2.1 Hz, 1H), 7.45-7.40 (m, 2H), 7.32 (dd, J=10.3, 4.8 Hz, 2H), 7.24 (dt, J=2.4, 1.6 Hz, 1H), 7.12 (dd, J=7.8, 0.8 Hz, 1H), 6.96 (dd, J=10.4, 5.3 Hz, 1H), 6.74 (d, J=2.1 Hz, 1H), 6.63 (d, J=7.7 Hz, 1H), 5.49 (dd, J=8.3, 4.8 Hz, 1H), 2.90-2.80 (m, 2H), 2.46 (s, 3H), 2.39-2.29 (m, 1H), 2.16-2.06 (m, 1H). MS (ESI, m/z): 282.26 (M+H)+.

Example 14

TRPA1 Inhibitory Activity Test

In this example, the compounds prepared in some examples of the present invention (shown in Table 1) were tested for their inhibitory activity on the transient receptor potential channel protein TRPA1. Wherein, compound of formula A (WO2010075353) was used as positive control:

Formula A

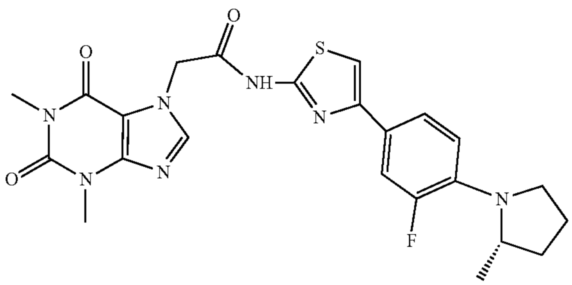

The method was as follows:

Test method by using IonWorks Barracuda (IWB) automatic patch clamp detection: HEK293 cells stably expressing TRPA1 were placed in a 37° C., 5% $CO_2$ incubator and incubated with DMEM medium containing 15 μg/mL Blasticidin S HCl, 200 μg/mL Hygromycin B and 10% FBS serum in a T175 culture flask. When the cell density grew to ~80%, the culture medium was removed, the cells were washed with calcium and magnesium free phosphate buffered saline (PBS), and 3 mL of Trypsin was added and digested for 2 minutes, and 7 mL of culture medium was added to terminate the digestion. The cells were collected into a 15 mL centrifuge tube and centrifuged at 800 r/min for 3 minutes, after removing the supernatant, the cells were added into the extracellular fluid with appropriate volume to re-suspend, so that the cell density was controlled at 2-3×$10^6$/mL for IWB experiments. Extracellular fluid formulation (in mM): 140 NaCl, 5 KCl, 1 $MgCl_2$, 10 HEPES, 0.5 EGTA, 10 Glucose (pH 7.4); Intracellular fluid formulation (in mM): 140 CsCl, 10 HEPES, 5 EGTA, 0.1 $CaCl_2$, 1 $MgCl_2$ (pH 7.2). Amphotericin B was freshly prepared with DMSO to 28 mg/mL on the day of the experiment, and then formulated into a final concentration of 0.1 mg/mL with the intracellular fluid.

The IWB experiment used a population patch clamp (PPC) plate, and the entire detection process was automatically completed by the instrument, that is, extracellular fluid was added into the 384 wells of the PPC plate, and the intracellular fluid was added into the plenum which was under the PPC plate, and then 6 L of cell fluid was added for sealing test, and finally the intracellular fluid in plenum was replaced with amphotericin B-containing intracellular fluid, so that the sealed cells were perforated to form a whole-cell recording mode. The sampling frequency for recording the TPRA1 current was 10 kHz, the cell was clamped at 0 mV, and the voltage stimulation command (channel protocol) was a ramp voltage from −100 mV to +100 mV for 300 ms, the voltage stimulation was given every 10 s, and the mTRPA1 current was induced via 300 M AITC.

Data recording and current amplitude measurement and export were completed by IWB Software (version 2.5.3, Molecular Devices Corporation, Union City, CA). The statistics of the well with a sealing impedance lower than 20 MΩ were not recorded. The original current data was corrected by software, the TRPA1 current amplitude was measured in +100 mV. Every PPC plate of the experiment would have one HC030031 dose-effect data as positive control, for example, when $IC_{50}$ value of a HC030031 was higher than 3 times of the average of that obtained on each preceding plate, a retest would be carried out. The dose-effect curve and $IC_{50}$ of compounds were fitted and calculated by GraphPad Prism 5.02 (GraphPad Software, San Diego, CA).

Experimental Results

A part of the compounds prepared in the examples of the present invention were tested for $IC_{50}$ inhibitory activity by the test method of IonWorks Barracuda (IWB) automatic patch clamp detection. The activity data was shown in Table 2.

??TABLE 2

Inhibitory activity data ($IC_{50}$, μM) of part of compounds of the present invention against TRPA1 in automatic patch clamp detection

| Number | $IC_{50}$(μM) |
|---|---|
| Compound I-1 | +++++ |
| Compound I-2 | ++++ |
| Compound I-3 | +++++ |
| Compound I-4 | +++++ |
| Compound I-5 | +++++ |
| Compound I-6 | ++++ |
| Compound I-8 | +++++ |
| Compound I-9 | ++++ |
| Compound I-11 | ++++ |
| Compound C2 (Comparative Example 2) | +++ |
| Formula A | + |
| Compound R-Duloxetine | ++ |

In which, the activity: $IC_{50}$(μM):
51-100: +
21-50: ++
11-20: +++
6-10: ++++
1-5: +++++

The results showed that the compounds of the present invention showed a strong inhibitory activity against TRPA1. Among them, 5 compounds have a half effective inhibitory concentration $IC_{50}$ against TRPA1 between 1-5 μM, and 4 compounds have a half effective inhibitory concentration $IC_{50}$ against TRPA1 between 6-10 μM. As shown in FIG. 1, the compound I-1 of the present invention has an inhibitory activity $IC_{50}$ of 2.06 μM against TRPA1. Therefore, it can be concluded that the compound of formula I-1 of the present invention has a strong inhibitory activity against TRPA1.

In addition, the activity ratio of compound I-1 (containing heteroaryl) and comparative compound C2 (containing phenyl) ($IC_{50}$ of compound C2/$IC_{50}$ of compound I-1) is about 6.3, which shows that the compound containing heteroaryl of the present invention (such as I-1) has higher inhibitory activity against TRPA1.

Compared with compounds in which the A group is a benzene ring (such as R-duloxetine), $IC_{50}$ value of compound I-1, compound I-3, compound I-4, compound I-5, compound I-8 and compound I-9 are significantly lower. The ratio of the $IC_{50}$ of R-duloxetine to the $IC_{50}$ of any one of compound I-1, compound I-3, compound I-4, compound I-5, compound I-8 and compound I-9 is about 9.3-23.5. This indicates that the compounds of the present invention in which the A group is an alicyclic or heteroaryl have higher inhibitory activity against TRPA1.

Figure 2:
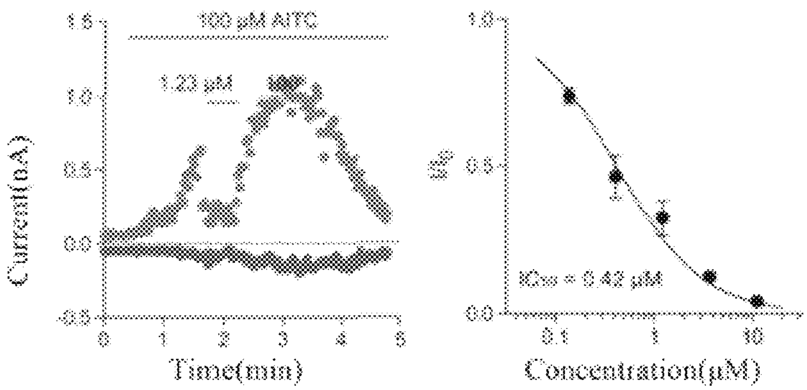
FIG. 2 shows the TRPA1 inhibitory activity $IC_{50}$ of compound I-1 tested by manual patch clamp.

The inventors measured the TRPA1 inhibitory activity of compound I-1 via the manual patch clamp detection method, as shown in FIG. 2, which is similar to the results of the automatic patch clamp detection method. In the manual patch clamp detection method, the $IC_{50}$ of compound I-1 is 0.42 μM, which shows a strong inhibitory activity against TRPA1.

Example 15

Cytotoxicity Test

In this example, the hepatocyte toxicity and neurocytotoxicity of compound I-1 and S-duloxetine were tested.

1. Hepatocyte Toxicity and Neurocytotoxicity of Compound I-1.

HepG-2 and SH-SY5Y cells were prepared and placed in 10 cm dish and incubated at 37° C., 5% $CO_2$ in a cell incubator; the cells were digested with trypsinize, resuspended and then counted. Based on a system of 100 μl/well, 8000 cells were transferred to a 96-well plate. The cells were incubated in a 37° C., 5% $CO_2$ cell incubator for 24 hours; a gradient concentration system of compound I-1 (prepared in Example 2) was prepared, 2 times diluted, the system was 100 μl/well. The supernatant in the 96-well plate cell culture system on the first day was removed, and a fresh prepared drug concentration system was added to the corresponding culture plate wells culturing cells (set up duplicate wells). The cells were cultured in 5% $CO_2$ incubator at 37° C. for 72 hours. After completion of the culture, the supernatant was removed from the cell culture system of the 96-well plate, 100 μl of detection solution (medium containing 10% CCK-8) was add to each well, and incubated in a cell incubator at 37° C. and 5% $CO_2$ for 1 hour, then taken it out and measured the absorbance at 450 nm with a microplate reader. Data were processed, cytotoxicity was calculated, and $IC_{50}$ was calculated by GraphPad Prism. The equation for calculating cytotoxicity is as follows: cytotoxicity (%)=[A (0 dosing)−A (dosing)]/[A (0 dosing)−A (blank)]×100

A (dosing): absorbance of the well having cells, CCK-8 solution and drug solution A (blank): absorbance of the well having medium and CCK-8 solution, without cells.

A (0 dosing): absorbance of the well having cells and CCK-8 solution, without drug solution 2. Hepatocyte Toxicity and Neurocytotoxicity of S-duloxetine.

The test method was similar to the above hepatocyte toxicity and neurocytotoxicity of the compound I-1, except that compound I-1 was replaced with S-duloxetine.

Results

The results of the hepatotoxicity (HepG2 cells) and neurocytotoxicity (SH-SY5Y) of compound I-1 are as follows:

The hepatotoxicity and neurocytotoxicity ($IC_{50}$, μM) of S-duloxetine are 33.33 μM and 28.59 μM, respectively, while the hepatotoxicity and neurotoxicity ($IC_{50}$, μM) of compound I-1 of the present invention are about 113.80 μM and 100.70 μM, indicating that the compounds of the present invention have a significantly lower toxic effect and excellent safety.

Example 16

The therapeutic effect of compound I-1 on acute pain and inflammatory pain were investigated through formalin pain model in mice

Experimental Method

150 C57BL/6 mice (male, 9 weeks) were randomly divided into 15 groups with 10 mice for each group, and were used for the analgesic activity test of 3 compounds in the formalin pain model in mice: the compound I-1 group (compound I-1 prepared in Example 2, its hydrochloride was used in the experiment), the S-duloxetine group (its hydrochloride was used in the experiment) and the compound C1 group (compound C1 prepared in Comparative Example 1, its hydrochloride was used in the experiment), respectively. Before the start of the experiment, the mice were allowed to adapt to the experimental environment for 72 hours, during which there was no need to fast for food or water. The tested drugs were administrated by intraperitoneal injection, and the doses were as follows:

The compound I-1 group: blank Vehicle (blank normal saline control), 0.1 mg/kg, 0.5 mg/kg, 1 mg/kg, 5 mg/kg and 10 mg/kg;

The S-duloxetine group: blank Vehicle (blank normal saline control), 1 mg/kg, 5 mg/kg, 10 mg/kg and 20 mg/kg;

The Compound C1 group: blank Vehicle (blank normal saline control), 0.1 mg/kg, 0.5 mg/kg, 1 mg/kg, 5 mg/kg and 10 mg/kg.

After the administration, the mice were placed in a transparent, ventilated plexiglass cylinder, and 1 hour later, 20 μl of 4% formalin solution was injected into the left hind foot plantar of each group of mice with a micro-injector, and foot pain response in mice were recorded in real time with a miniature camera. The length of time of licking the left foot was used as an indicator of pain response, the licking time were observed and recorded during two periods of 0-10 min (phase I) and 10-60 min (phase II) respectively, for statistical analysis, and the half effective dose ($ED_{50}$) of the 3 compounds were calculated: $ED_{50}$ refers to the drug dose that reduces the licking time by half compared with the blank control group. The smaller the $ED_{50}$ value is, the lower the effective analgesic dose of the compound is and the better its analgesic effect is.

Results

Figure 3:
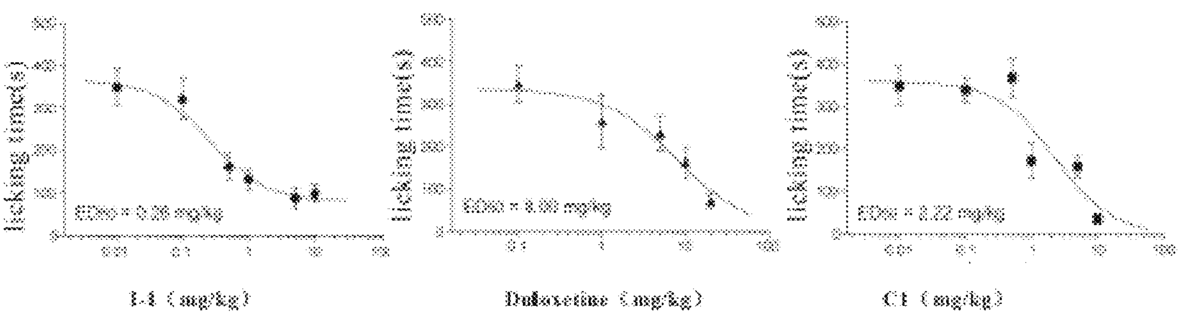
FIG. 3 shows the $ED_{50}$ results of compound I-1 of the present invention, S-duloxetine and comparative compound C1 in the formalin pain model in mice.

The test results of formalin pain model in mice are shown in Table 3 and FIG. 3. As can be seen in Table 3 and FIG. 3, the analgesic activity of all three compounds showed a dose dependence. The compound I-1 of the present invention had a phase II (10-60 min) licking time that was already reduced by more than 50% compared to the blank Vehicle at an administered dose of 0.5 mg/kg, with an analgesic potency $ED_{50}$ of 0.26 mg/kg in phase II pain. The $ED_{50}$ of S-duloxetine in phase II pain was 8.00 mg/kg, and the $ED_{50}$ of comparative compound C1 in phase II pain was 2.22 mg/kg. From the above data, it can be seen that the compound I-1 of the present invention exhibits extremely strong analgesic activity in the formalin pain model in mice, and its $ED_{50}$ is 30.8 times stronger than that of S-duloxetine, and 8.5 times stronger than that of C1 compound. The formalin model in mice is a classic model for evaluating the efficacy of drugs for acute pain and inflammatory pain, and therefore the compound I-1 of the present invention has excellent therapeutic effects on acute pain and inflammatory pain.

TABLE 3 statistical results of the licking time of the compound I-1 of the present invention, S-duloxetine and comparative compound C1 in the formalin model in mice at different doses in phase II (10-60 min)

| | statistics of the licking time (s) | | |
|---|---|---|---|
| Dose | Compound I-1 | S-duloxetine | Compound C1 |
| Blank Vehicle | 349.55 ± 43.09 | 349.55 ± 43.09 | 349.55 ± 43.09 |
| 0.1 mg/kg | 321.55 ± 47.75 | — | 339.35 ± 27.90 |
| 0.5 mg/kg | 161.25 ± 30.83 | — | 368.16 ± 44.46 |
| 1 mg/kg | 131.28 ± 23.99 | 259.97 ± 64.44 | 171.57 ± 39.69 |
| 5 mg/kg | 87.85 ± 25.15 | 230.49 ± 41.31 | 158.02 ± 25.18 |
| 10 mg/kg | 99.08 ± 19.73 | 162.83 ± 36.27 | 35.68 ± 11.77 |
| 20 mg/kg | — | 72.27 ± 17.29 | — |

Example 17

The therapeutic effect of compounds I-1 on acute pain was investigated through hot plate induced pain model in rat Experimental Method Male, mature and unmated healthy Sprague-Dawley rats were selected, and the temperature of the cold/hot plate (product model: PE34, US IITC) was adjusted to a constant temperature of 53±0.1° C., and rats with painful response such as foot licking, foot shaking or slight jumping within 5-10 s were screened (abandoned those who evaded and jumped). The 50 animals screened were weighed and randomly divided into 5 groups (10 rats in each group): normal saline control group (Vehicle, blank control), S-duloxetine group (its hydrochloride salt was used in the experiment), gabapentin group, comparative compound C1 group (compound C1 prepared in Comparative Example 1, and its hydrochloride salt was used in the experiment) and compound I-1 group (compound I-1 prepared in Example 2, and its hydrochloride salt was used in the experiment). The tested compound was freshly formulated on the day of administration. A 0.9% NaCl normal saline solution was prepared as a vehicle, an appropriate amount of the test compound was added to the required volume of normal saline, and the mixture was fully suspended to prepare the drug at a concentration of 1 mg/ml. The standard of dose in volume to rats was 10 ml/kg via intraperitoneal administration, animals did not need to fast food or water before administration. The dose of S-duloxetine, compound C1 and compound I-1 were 30 mg/kg, and the dose of gabapentin was 100 mg/kg. The latency of thermal pain was measured at 0.5 h, 1 h and 2 h after drug administration. To avoid scalding the animals on the hot plate, the maximum latency was set to 30 s. The analgesic effect of each compound was evaluated using the maximum possible effect (MPE), i.e. MPE %=[(Post drug latency-baseline latency)/(30−baseline latency)]×100. Statistics of MPE % at different time points. The higher the value of MPE % is, the more potent the analgesic efficacy of the compound is.

Results

Figure 4:
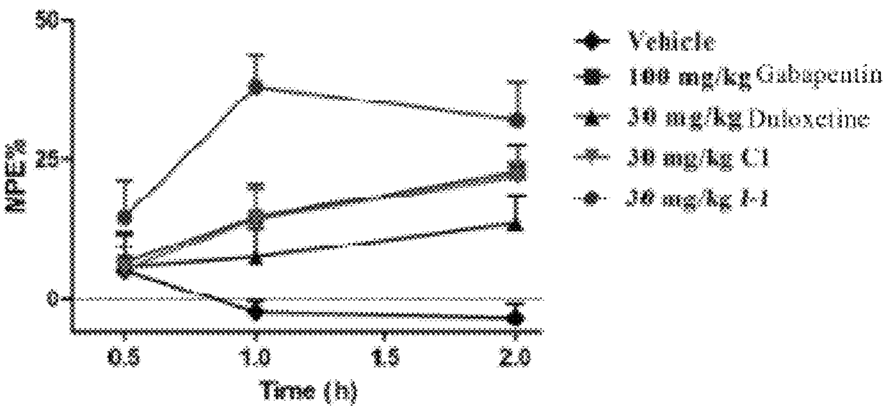
FIG. 4 shows the statistical graph of MPE % of compound I-1 of the present invention, S-duloxetine, comparative compound C1 and gabapentin in the hot plate induced pain model in rat at different times.

The results of analgesic activity of compounds in hot plate induced pain model in rat are shown in Table 4 and FIG. 4. It can be seen from the results in Table 4 and FIG. 4, compound I-1 of the present invention exhibits a very potent analgesic effect at an administered dose of 30 mg/kg compared with the normal saline control group, with significant differences. Compared with the positive control, the analgesic activity within 2 hours of compound I-1 of the present invention is significantly superior to that of gabapentin at 100 mg/kg, and superior to that of S-duloxetine and comparison compound $C_1$ at 30 mg/kg. The hot plate induced pain model is a classic model for evaluating the efficacy of drugs for acute pain, and therefore the compound I-1 of the present invention has excellent therapeutic effect on acute pain.

TABLE 4

MPE % statistics at different times for compound I-1 of the present invention, S-duloxetine, comparison compound C1 and gabapentin in the hot plate induced pain model in rat

| | | MPE % | | |
|---|---|---|---|---|
| Compound | Dose | 0.5 h | 1 h | 2 h |
| normal saline group | | 5.15 ± 4.31 | −2.31 ± 1.95 | −3.39 ± 2.47 |
| Compound I-1 | 30 mg/kg | 14.51 ± 6.87 | 38.03 ± 5.66 | 31.92 ± 6.79 |
| S-duloxetine | 30 mg/kg | 5.75 ± 5.74 | 7.44 ± 5.12 | 13.53 ± 4.99 |
| Compound C1 | 30 mg/kg | 5.29 ± 1.56 | 14.20 ± 5.71 | 21.83 ± 2.45 |
| Gabapentin | 100 mg/kg | 6.47 ± 5.49 | 14.56 ± 6.18 | 22.66 ± 4.93 |

Example 18

The therapeutic effect of compound I-1 on visceral pain and inflammatory pain was investigated through acetic acid writhing pain model in mice Experimental Method ICR mice, male, 22-25 g, were fasted for food 2 h before administration, but can have water. All ICR mice were weighed and randomly grouped with the number of animals>10 per group. The negative control group was a normal saline group (Vehicle, blank control), and the positive control groups were set to a dose of 10 mg/kg indomethacin (a non-steroidal anti-inflammatory drug), a dose of 10 mg/kg Anisodamine (an antispasmodic drug with clinically analgesic activity), a dose of 10 mg/kg S-duloxetine (its hydrochloride was used in the experiment) and a dose of 20 mg/kg S-duloxetine (its hydrochloride was used in the experiment). Test compound I-1 (compound I-1 prepared in Example 2, its hydrochloride was used in the experiment, in a dose of 5 mg/kg and 10 mg/kg). The mice were administered via intragastric administration according to the weight of mice. 1.5% acetic acid solution (0.1 ml/10 g) was intraperitoneally injected at 1 hour after administration, and the number of times of visceral pain in each group within 30 minutes was observed, the mice were counted once when the abdomen was concave, the trunk and hind legs were extended and the hips were elevated, and the number of times of these phenomena occurred within 30 min was finally counted. The less visceral pain occurred in mice after administration, which indicated that the analgesic effect of the compound was stronger.

Results

Figure 5:
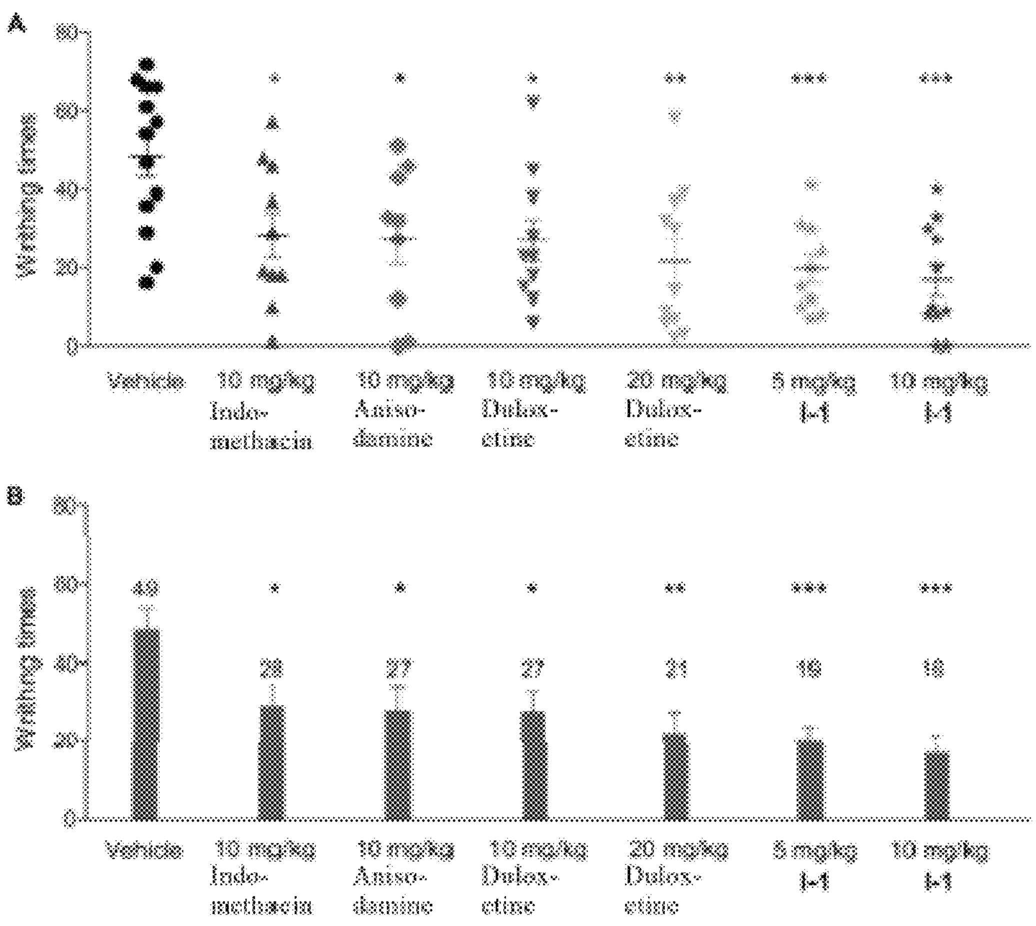
FIG. 5 shows the results of analgesic activity of compound I-1 of the present invention, S-duloxetine, indomethacin and anisodamine in the acetic acid writhing pain model in mice.

The acetic acid writhing pain model in mice was tested as shown in FIG. 5, from which it can be seen that by single intragastric administration of compound I-1 (5 mg/kg and 10 mg/kg) of the present invention significantly reduced the number of acetic acid-induced writhing reactions in mice, with a significant difference compared with the normal saline group (vehicle, blank control) (49 times). The number of visceral pains in mice at a dose of 5 mg/kg administered with compound I-1 was 19, which was 50% lower than the 49 in the normal saline control group, suggesting that the half effective dose ($ED_{50}$) of compound I-1 in this model is less than 5 mg/kg. The analgesic effect of compound I-1 at a dose of 10 mg/kg (16 times) is superior to that of the positive drugs indomethacin (28 times), anisodamine (27 times) and S-duloxetine (27 times) at the same dose, and the analgesic effect of compound I-1 at a dose of 5 mg/kg (19 times) is comparable to that of S-duloxetine at 20 mg/kg (21 times). This experiment showed that the analgesic activity of compound I-1 of the present invention was significantly better than that of the positive control drug in acetic acid writhing pain model in mice. The acetic acid writhing pain model in mice is a classic model for evaluating the efficacy of drugs in the treatment of visceral pain and inflammatory pain, and therefore the compound I-1 of the present invention has excellent therapeutic effect on visceral pain and inflammatory pain.

Example 19

The therapeutic effect of compound I-1 on nerve pain was investigated through rat SNL model.

Experimental Method

1. Surgery

SD rats were taken for surgery, male, SPF grade, mass 150 g-180 g. The surgical procedure was performed aseptically. The animals were anesthetized with sodium pentobarbital (50 mg/kg, intraperitoneal injection). The surgical area of the waist of animals was shaved, and the skin was disinfected three times with iodophor and 70% ethanol. Start the operation after the skin was dry. A longitudinal incision was made in the posterior part of the sacral bone of the animal's waist with a scalpel to expose the left paravertebral muscles, and the muscle tissue was separated with a distractor to expose the vertebra. The left spinal nerves L5 and L6 were separated, ligated with 6-0 silk thread, and the wounds were sutured. After the surgery, the animals were placed on an electric blanket and injected subcutaneously with 5 mL normal saline to prevent dehydration. When the animal was completely awake (free to move), put the animal back into the cage.

2. Grouping and Mechanical Hyperalgesia Test

After the surgery, the animals were adapted in the experimental environment for 15 minutes/day for 3 days. On the day before the administration, the baseline test of mechanical hyperalgesia was carried out on rats, and the animals without mechanical hyperalgesia (paw withdrawal threshold greater than 5 g) were abandoned, then the animals were randomly divided into one control group and three experimental groups.

Administration:

The animal were weighed, in terms of administered dose, the three experimental groups were given 100 mg/kg gabapentin, 10 mg/kg S-duloxetine (its hydrochloride was used in the experiment) and 10 mg/kg Compound I-1 (compound I-1 prepared in Example 2, and its hydrochloride was used in the experiment) via intragastric administration, respectively, and the control group was given an equal volume of normal saline via intragastric administration. After administration, mechanical hyperalgesia test was performed. The rats were placed individually in a plexiglas box with a grid at the bottom of the box to ensure that the feet of the rats can be tested. Rats would adapt for 15 minutes before the test. After the adaptation was completed, the test fiber was used to test rat at the center of the sole of the left hind foot. The test fibers included 8 test strengths: 3.61 (0.4 g), 3.84 (0.6 g), 4.08 (1 g), 4.31 (2 g), 4.56 (4 g), 4.74 (6 g), 4.93 (8 g) and 5.18 (15 g). For the test, the test fiber were pressed vertically against the skin and force was applied to bend the fiber for 6-8 seconds, with a 5 seconds interval between each test. The rapid paw withdrawal of the animal during the test was recorded as a pain response. The paw withdrawal of the animal when the test fiber left the animal's skin was also recorded as a pain response. If the animal moved or walked, it will not be recorded as a pain response, the test should be repeated. The test was firstly performed with 4.31 (2 g), and if the animal had a pain response, the next test was performed with a test fiber of a lower strength; if the animal did not have a pain response, the next test was performed with a test fiber of a higher strength. The maximum strength of the tested fiber was 5.18 (15 g).

Mechanical hyperalgesia was expressed as the paw withdrawal threshold (PWT) in the behavioral test of rats, which was calculated according to the following equation:

$$50\%\ \text{response threshold (g)}=(10(^{Xf+k\delta}))/10{,}000$$

Xf=the final test fiber value used in the test

K=table value

δ=Average difference

Data were collected using Excel software and analyzed using Prism 6.01 (Graph pad software, Inc.) software. Higher values of the paw withdrawal threshold (PWT) indicate that the compound is more potent in analgesia.

Results

Figure 6:
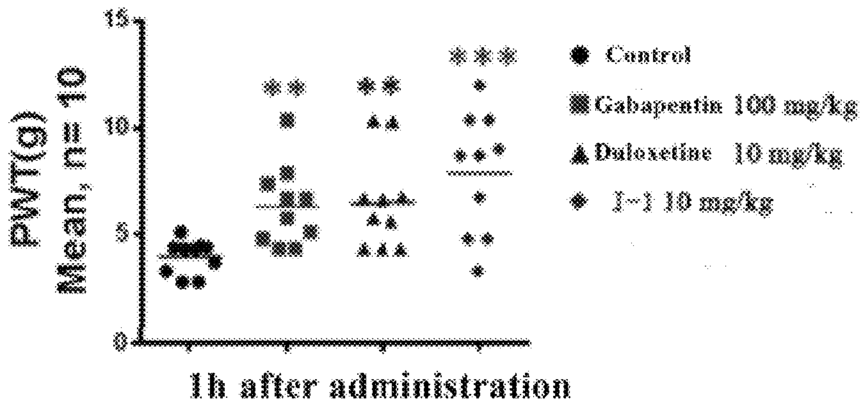
FIG. 6 shows the results of analgesic activity of compound I-1 of the present invention, S-duloxetine and gabapentin in the SNL model in rat.

The results of analgesic activity in the SNL model in rat are shown in Table 5 and FIG. 6. It can be seen from the results of Table 5 and FIG. 6, the compound I-1 of the present invention exhibits a very potent analgesic effect at an administration dose of 10 mg/kg, with a significant difference compared with the normal saline control group. Compared with the positive control group, the analgesic activity of the compound I-1 of the present invention is superior to that of 100 mg/kg gabapentin and 10 mg/kg S-duloxetine at 1 hour after administration. The SNL model in rat is a classic model for evaluating the efficacy of drugs in the treatment of nerve pain, and therefore the compound I-1 of the present invention has excellent therapeutic effect on nerve pain.

TABLE 5

Paw withdrawal threshold (PWT) statistics data of compound I-1 of the present invention, S-duloxetine and gabapentin in the SNL model in rat, 1 hour after administration

| Compound | Dose | PWT (g), |
|---|---|---|
| Control group | | 3.967 ± 0.775 |
| Compound I-1 | 10 mg/kg | 7.869 ± 2.846 |
| S-duloxetine | 10 mg/kg | 6.519 ± 2.226 |
| Gabapentin | 100 mg/kg | 6.352 ± 1.897 |

Example 20

Preparation and characterization of the hydrochloride A of the compound of Formula I-1 of the present invention.

XRPD: X-ray powder diffraction; DSC: Differential scanning calorimetry; TGA: Thermogravimetric analysis; DVS: Dynamic water adsorption;

X-ray powder diffraction analysis method: PANalytical X-ray powder diffraction analyzer, working voltage: 40 kV, working current: 40 mA, using Cu target to obtain X-ray powder diffraction pattern.

Differential scanning calorimetry (DSC): The instrument was DSC Q2000; Scanning speed: 10° C./min; Protective gas, nitrogen.

Thermogravimetric analysis (TGA): TGA Q500; Scanning speed: 10° C./min; Protective gas: nitrogen.

Preparation method of the crystal form A of the hydrochloride of the compound of Formula I-1:

0.73 kg of the free base of the compound of formula I-1 prepared in Example 2 was weighed and added into 11 L of ethyl acetate, stired, and cooled to 5~15° C. with an ice water bath, slowly added 37% concentrated hydrochloric acid dropwise to adjust the pH of the system to 7, and the reaction was stirred for 5 minutes. A solid precipitated out, filtered, the filter cake was washed with ethyl acetate and then placed in an oven (40~45° C.) and dried to a constant weight to obtain 0.45 kg the crystal form A of the hydrochloride of the compound of formula I-1, with a yield of 54.70%.

Identification of the crystal form A of the hydrochloride of the compound of Formula I-1

The X-ray powder diffraction data of the crystal form A of the hydrochloride of the compound of Formula I-1 are shown in Table 6, and the XRPD pattern is shown in FIG. 7, having the following characteristic peaks expressed with 2 theta: 10.003, 11.171, 15.987, 16.734, 17.092, 18.173, 18.849, 20.681, 21.156, 21.649, 22.084, 22.794, 23.761, 25.298, 25.967, 26.640, 27.273, 28.099, 28.615, 28.813, 29.501, 30.118, 30.513, 32.522, 33.274, 34.081, 35.815, 37.553, 40.018, 42.927, 44.129.

TABLE 6

| 2 theta value | d value | Relative Intensity % |
|---|---|---|
| 10.003 | 8.8355 | 28.3 |
| 11.171 | 7.9137 | 12.8 |
| 15.987 | 5.5392 | 15.2 |
| 16.734 | 5.2936 | 51.9 |
| 17.092 | 5.1836 | 35.7 |
| 18.173 | 4.8774 | 100.0 |
| 18.849 | 4.7041 | 12.7 |
| 20.681 | 4.2913 | 13.6 |
| 21.156 | 4.1961 | 65.2 |
| 21.649 | 4.1017 | 35.3 |
| 22.084 | 4.0217 | 71.9 |
| 22.794 | 3.8981 | 91.8 |
| 23.761 | 3.7416 | 65.0 |
| 25.298 | 3.5177 | 46.3 |
| 25.967 | 3.4285 | 11.5 |
| 26.640 | 3.3433 | 29.2 |
| 27.273 | 3.2672 | 16.9 |
| 28.099 | 3.1730 | 35.7 |
| 28.615 | 3.1170 | 33.1 |
| 28.813 | 3.0959 | 25.2 |
| 29.501 | 3.0253 | 10.4 |
| 30.118 | 2.9647 | 12.1 |
| 30.513 | 2.9272 | 13.2 |
| 32.522 | 2.7508 | 18.4 |
| 33.274 | 2.6904 | 12.4 |
| 34.081 | 2.6285 | 13.2 |
| 35.815 | 2.5051 | 13.4 |
| 37.553 | 2.3931 | 9.6 |
| 40.018 | 2.2512 | 8.2 |
| 42.927 | 2.1051 | 10.6 |
| 44.129 | 2.0505 | 9.0 |

The differential scanning calorimetry (DSC) pattern of the crystal form A of the hydrochloride is substantially as shown in FIG. 8, and the endothermic peak begins to appear upon being heated to 142.30° C.

The thermogravimetric analysis (TGA) pattern of the crystal form A of the hydrochloride is substantially as shown in FIG. 9, with a weight loss of about 0.9827% upon being heated to 168.01° C.

Investigation on the characteristics of the crystal form A of the hydrochloride of the compound of formula I-1

(1) The hygroscopicity experiment of the crystal form A of the hydrochloride of the compound of formula I-1:

Hygroscopicity was tested by dynamic moisture absorption (DVS) instrument. The crystal form A of the hydrochloride of the compound of formula I-1 has a weight change of less than 0.2% under 25° C./80RH conditions, indicating that it has no hygroscopicity and has excellent high humidity stability, which eliminates the need for storage and transportation under harsh dry conditions, thereby reducing storage and transportation costs. (Refer to the 2015 edition of the Chinese Pharmacopoeia (Guiding Principles for Drug Hygroscopicity Test)).

(2) Stability study of the crystal form A of the hydrochloride of the compound of formula I-1:

About 10 mg of the crystal form A of the hydrochloride of the compound of formula I-1 was weighed and added into an HPLC vial, the bottle was sealed with a parafilm, 10 small holes were pierced in the film, and the vial was placed at 25° C./60% RH or 40° C./75% RH environment for 4 weeks, sampled in the first and fourth weeks respectively. Purity (using HPLC analysis) and crystal form (using X-ray powder diffraction analysis) of the samples were investigated. The results are shown in Table 7. It can be seen from Table 7 that after the crystal form A of the hydrochloride of the compound of formula I-1 was placed for 1 week and 4 weeks, the HPLC (high performance liquid chromatography) purity does not decrease significantly and no change in crystal form is observed, indicating the crystal form A of the hydrochloride of the compound of formula I-1 has a good thermal and other stability in physical and chemical.

TABLE 7

| | | | 25° C./60% RH | | 40° C./75% RH | |
|---|---|---|---|---|---|---|
| Crystal form | Initial purity (area %) | Experimental duration | Purity (area %) | Change of crystal form | Purity (area %) | Crystal form change |
| Crystal form A of the hydrochloride | 100 | 1 week<br>4 weeks | 100<br>100 | NO | 100<br>100 | NO |

Example 21

The therapeutic effect of compound I-1 on postoperative pain was investigated through postoperative pain model in rat Experimental Method 1. Drug Preparation Injection of compound I-1: 36.13 mg of compound I-1 prepared in Example 2 was weighed and added into 3.140 mL of normal saline, and well mixed by vortex;

Injection of Bupivacaine: purchased from Shanghai Zhaohui Pharmaceutical Co., Ltd.

The solvent of the test compound I-1 was normal saline, the administration dose was 10 mg/kg, and the administration method was intramuscular injection. 36.13 mg of the compound I-1 was weighed and added into 3.140 mL normal saline, and well mixed by vortex. The reference compound used in the experiment was bupivacaine injection, purchased from Shanghai Zhaohui Pharmaceutical Co., Ltd., in a dose of 10 mg/kg via intramuscular injection.

2. Surgery

Aseptic operation was performed during surgery, surgical instruments (scissors, forceps, scalpel, surgical cotton, suture thread) were disinfected before the operation. The rats were anesthetized with sodium pentobarbital (50 mg/kg, intraperitoneal injection), and the toes of the rats were squeezed to confirm that the animals were completely anesthetized before the surgery. Ophthalmic ointment was applied to the animal's eyes to prevent the animal's cornea from drying out. Iodophor and 70% ethanol were used to disinfect the skin of the surgery area on the sole of the left hind foot three times, and the surgery was started after the skin was dried. Starting at 0.5 cm from the heel, a 1 cm long incision was made longitudinally toward the toe. After cutting the skin, the flexor digitorum brevis was lifted to make longitudinal blunt injury. After pressing to stop the bleeding, the wound was sutured. The surgical instruments were cleaned and sterilized with hot bead sterilizer. After the surgery, the animals were placed on an electric blanket and injected subcutaneously with 5 mL normal saline to prevent dehydration. When the animal was completely awake (free to move), put the animal back into the cage.

3. Grouping and Administration

At 24 hours after the surgery, the baseline test of mechanical hyperalgesia was performed on rats. The animals that did not exhibit mechanical hyperalgesia (PWT>5 g) were abandoned, then the animals were randomly divided into groups according to PWT. The experiment was divided into three groups: model control group (normal saline group, intragastric administration of normal saline), bupivacaine group (intramuscular injection of bupivacaine at a dose of 10 mg/kg) and compound I-1 group (intramuscular injection of compound I-1 at a dose of 10 mg/kg). The rats in each group were tested for mechanical hyperalgesia at 1 hour and 2 hours after the administration.

4. Mechanical Hyperalgesia Test

Figure 10:
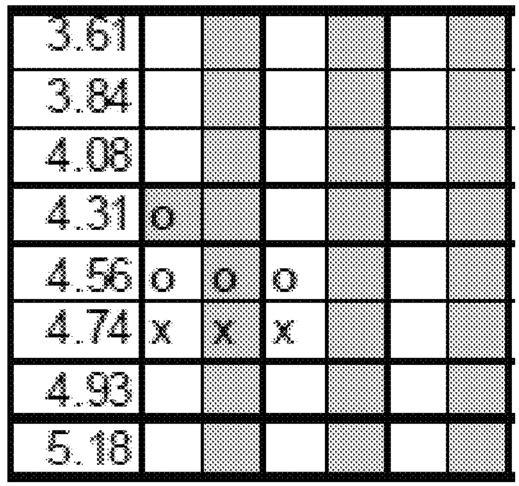
FIG. 10 is a table showing the results of the mechanical hyperalgesia test, as measured by pain response, performed on rats.

The rat was placed alone in a plexiglass box with a grid on the bottom of the box to ensure that the rat's feet can be tested. Rats would adapt for 15 minutes before the test. After the adaptation was completed, the test fiber was used to test in the center of the left hind foot of the rat. The test fibers included 8 test strengths: 3.61 (0.4 g), 3.84 (0.6 g), 4.08 (1 g), 4.31 (2 g), 4.56 (4 g), 4.74 (6 g), 4.93 (8 g) and 5.18 (15 g). During the test, the test fiber was pressed vertically to the skin and force was applied to bend the fiber for 6-8 seconds, with a test interval of 5 seconds. During the test, the animal's rapid foot shrinkage was recorded as a pain response. The animal's foot shrinkage when the test fiber left the animal's skin was also recorded as a pain response. If the animal moved or walked, it would not be recorded as the pain response, the test should be repeated. For the test, fiber 4.31 (2 g) was used at first. If the animal had a pain response, the test fiber with a lower strength was used in the next test; if the animal had no pain response, the test fiber with a higher strength was used in the next test. The maximum strength of the tested fiber was 5.18 (15 g). The mechanical hyperalgesia test results are recorded in the table of FIG. 10, in which pain response is indicated with an "x" and no pain response is indicated with an "o."

Mechanical hyperalgesia was expressed as the paw withdrawal threshold (PWT) in the behavioral test of rats, which was calculated according to the following equation:

$$50\% \text{ response threshold (g)}=(10(Xf+k))/10{,}000$$

Xf=the final test fiber value used in the test

K=table value (Chaplan et al. 1994, page 62)

□=Average difference

5. Data Collection and Analysis

Excel software was used to collect data. Prism 6.01 (Graph pad software, Inc.) software was used to analyze the data (two-way ANOVA plus Bonferroni multiple comparison test).

Results

Figure 11:
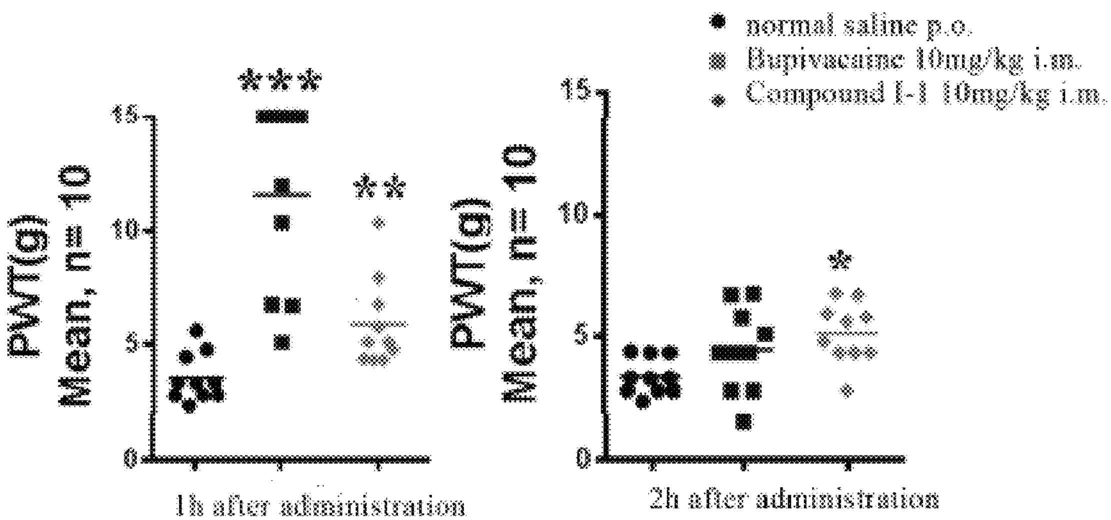
FIG. 11 shows the results of analgesic activity of compound I-1 of the present invention in a postoperative pain model in rat.

The results of the analgesic activity of compound I-1 in the postoperative pain model in rats are shown in Table 8 and FIG. 11. As can be seen from the results in Table 8 and FIG. 11, compound I-1 of the present invention exhibits a very potent analgesic effect at a dose of 10 mg/kg at 1 h and 2 h after administration, with significant differences compared with the normal saline control group. Compared with the positive drug bupivacaine, bupivacaine shows a stronger analgesic activity at 1 hour after administration, but no significant analgesic effect at 2 hours after administration, suggesting that compound I-1 has a longer analgesic effect in the postoperative pain model. The postoperative pain model in rat is a classic model for evaluating the efficacy of drugs in the treatment of postoperative pain, and therefore the compound I-1 of the present invention has excellent therapeutic effect on postoperative pain.

TABLE 8 paw withdrawal threshold (PWT) statistical data of Compound I-1 of the present invention and bupivacaine in the postoperative pain model in rat, 1 hour and 2 hours after administration

| | PWT (g) | |
|---|---|---|
| Compound | 1 hour | 2 hour |
| Normal Saline | 3.561 | 3.382 |
| Bupivacaine | 11.587 | 4.448 |
| Compound I-1 | 5.885 | 5.135. |

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A crystal form A of the hydrochloride salt of the compound of formula I-1,

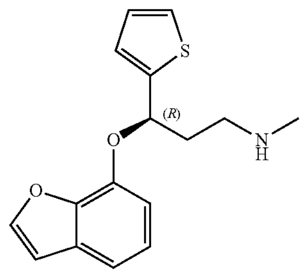

I-1 wherein the X-ray powder diffraction pattern of the crystal form A has characteristic peaks at 2θ angles of 18.173±0.2°, 22.084±0.2°, and 22.794±0.2°.

2. The crystal form A of the hydrochloride salt of the compound of formula I-1, according to claim 1, wherein the X-ray powder diffraction pattern of the crystal form A further includes characteristic peaks at one or more of 20 value selected from the group consisting of: 10.003±0.2°, 11.171±0.2°, 15.987±0.2°, 16.734±0.2°, 17.092±0.2°, 18.849±0.2°, 20.681±0.2°, 21.156±0.2°, 21.649±0.2°, 23.761±0.2°, 25.298±0.2°, 25.967±0.2°, 26.640±0.2°, 27.273±0.2°, 28.099±0.2°, 28.615±0.2°, 28.813±0.2°, 29.501±0.2°, 30.118±0.2°, 30.513±0.2°, 32.522±0.2°, 33.274±0.2°, 34.081±0.2°, 35.815±0.2°, 37.553±0.2°, 40.018±0.2°, 42.927±0.2°, and 44.129±0.2.

3. The crystal form A of the hydrochloride salt of the compound of formula I-1, according to claim 1, wherein the X-ray powder diffraction pattern of the crystal form A has characteristic peaks and peak intensity as follows:

| 2θ value | d value | relative intensity % |
|---|---|---|
| 10.003 | 8.8355 | 28.3 |
| 11.171 | 7.9137 | 12.8 |
| 15.987 | 5.5392 | 15.2 |
| 16.734 | 5.2936 | 51.9 |
| 17.092 | 5.1836 | 35.7 |
| 18.173 | 4.8774 | 100.0 |
| 18.849 | 4.7041 | 12.7 |
| 20.681 | 4.2913 | 13.6 |
| 21.156 | 4.1961 | 65.2 |
| 21.649 | 4.1017 | 35.3 |
| 22.084 | 4.0217 | 71.9 |
| 22.794 | 3.8981 | 91.8 |
| 23.761 | 3.7416 | 65.0 |
| 25.298 | 3.5177 | 46.3 |
| 25.967 | 3.4285 | 11.5 |
| 26.640 | 3.3433 | 29.2 |
| 27.273 | 3.2672 | 16.9 |
| 28.099 | 3.1730 | 35.7 |
| 28.615 | 3.1170 | 33.1 |
| 28.813 | 3.0959 | 25.2 |
| 29.501 | 3.0253 | 10.4 |
| 30.118 | 2.9647 | 12.1 |
| 30.513 | 2.9272 | 13.2 |
| 32.522 | 2.7508 | 18.4 |
| 33.274 | 2.6904 | 12.4 |

-continued

| 2θ value | d value | relative intensity % |
|---|---|---|
| 34.081 | 2.6285 | 13.2 |
| 35.815 | 2.5051 | 13.4 |
| 37.553 | 2.3931 | 9.6 |
| 40.018 | 2.2512 | 8.2 |
| 42.927 | 2.1051 | 10.6 |
| 44.129 | 2.0505 | 9.0. |

4. The crystal form A of the hydrochloride salt of the compound of formula I-1 according to claim 1, wherein:

(i) upon being heated to 142.30° C., endothermic peaks appear in a differential scanning calorimetry (DSC) pattern of the crystal form A of the hydrochloride salt of the compound of formula I-1; and/or (ii) upon being heated to 168.01° C., a weight loss of about 0.9827%±0.5% is observed in a thermogravimetric analysis (TGA) pattern of the crystal form A of the hydrochloride salt of the compound of formula I-1.

5. A pharmaceutical composition comprising, the crystal form A of the hydrochloride salt of the compound of formula I-1 according to claim 1; and a pharmaceutically acceptable carrier.

6. A method for inhibiting transient receptor potential channel protein TRPA1 in a subject in need thereof, comprising administering to the subject a therapeutically effective amount of the crystal form A of the hydrochloride salt of the compound of formula I-1 according to claim 5.

7. A method for treating pain in a subject in need thereof, comprising administering to the subject a therapeutically effective amount of the crystal form A of the hydrochloride salt of the compound of formula I-1 according to claim 1.

8. The method according to claim 7, wherein the pain is selected from the group consisting of acute pain, inflammatory pain, visceral pain, neurogenic pain, fibromyalgia, headache, nerve pain, mixed pain, cancer-induced pain, and combinations thereof.

9. The method according to claim 8, wherein the acute pain is injury pain or postoperative pain; and/or the inflammatory pain is osteoarthritis pain or rheumatoid arthritis pain.

10. The crystal form A of the hydrochloride salt of the compound of formula I-1 according to claim 1, wherein the crystal form A comprises one or more features selected from the group consisting of:

(i) the crystal form A of the hydrochloride salt of the compound of formula I-1 has X-ray powder diffraction characteristic peaks substantially as shown in FIG. 7;

(ii) the differential scanning calorimetry (DSC) pattern of the crystal form A of the hydrochloride salt of the compound of formula I-1 is substantially as shown in FIG. 8; and (iii) the thermogravimetric analysis (TGA) pattern of the crystal form A of the hydrochloride salt of the compound of formula I-1 is substantially as shown in FIG. 9.

* * * * *